(12) United States Patent
Yang et al.

(10) Patent No.: US 9,902,701 B2
(45) Date of Patent: Feb. 27, 2018

(54) PYRIDAZONES AND TRIAZINONES FOR TREATMENT AND PROPHYLAXIS OF HEPATITIS B VIRUS INFECTION

(71) Applicant: Hoffmann-La Roche Inc., Little Falls, NJ (US)

(72) Inventors: Song Yang, Shanghai (CN); Chungen Liang, Shanghai (CN); Jianping Wang, Shanghai (CN); Song Pan, Shanghai (CN)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/432,706

(22) Filed: Feb. 14, 2017

(65) Prior Publication Data
US 2017/0157133 A1    Jun. 8, 2017

Related U.S. Application Data

(63) Continuation of application No. PCT/EP2015/068406, filed on Aug. 11, 2015.

(30) Foreign Application Priority Data

Aug. 14, 2014 (WO) ............... PCT/CN2014/084356

(51) Int. Cl.
| | | |
|---|---|---|
| C07D 237/04 | (2006.01) |
| A61K 31/50 | (2006.01) |
| C07D 237/14 | (2006.01) |
| C07D 253/06 | (2006.01) |
| C07D 253/07 | (2006.01) |

(52) U.S. Cl.
CPC ............ *C07D 237/04* (2013.01); *A61K 31/50* (2013.01); *C07D 237/14* (2013.01); *C07D 253/06* (2013.01); *C07D 253/07* (2013.01)

(58) Field of Classification Search
CPC ............................... C07D 237/04; A61K 31/50
USPC ......................................... 544/239; 514/247
See application file for complete search history.

(56) References Cited

U.S. PATENT DOCUMENTS

| 2009/0088397 A1 | 4/2009 | Cuconati et al. |
| 2009/0291959 A1 | 11/2009 | Chang et al. |
| 2013/0303552 A1 | 11/2013 | Xu et al. |
| 2014/0274933 A1 | 9/2014 | Cole et al. |

FOREIGN PATENT DOCUMENTS

| CN | 102964340 A | 3/2013 |
| DE | 286 354 A5 | 1/1991 |
| WO | 99/47505 | 9/1999 |
| WO | 2003/097062 A1 | 11/2003 |
| WO | 2006/108640 A1 | 10/2006 |
| WO | 2008/016239 A1 | 2/2008 |
| WO | 2008/103277 | 8/2008 |
| WO | 2009/127544 | 10/2009 |
| WO | 2011/017261 A1 | 2/2011 |

OTHER PUBLICATIONS

Tang et al. Expert Opinion on Drug Discovery, 2017 vol. 12, No. 1, 5-15.*
Freshney et al.,Culture of Animal Cells, A Manual of Basic Technique, Alan R. Liss, Inc., 1983, New York, p. 4.*
Dermeret al., Bio/Technology, 1994, 12:320.*
Debarry et al. Liver International 2017; 37 (Suppl. 1): 67-72.*
PubChem Compound CID 6624415, Create Date Jun. 5, 2006.*
PubChem Search, Jan. 11, 2018.*
PubChem-Bioactivty-CID6624415, downloaded on Jan. 11, 2018.*
Acs et al., "Hepatitis B virus produced by transfected Hep G2 cells causes hepatitis in chimpanzees" Proc Natl Acad Sci USA 84:4641-4644 ( 1987).
Agostino Cilibrizzi et al., "Synthesis, HPLC Enantioresolution, and X-ray Analysis of a New Series of C5-methyl Pyridazines as N-Formyl Peptide Receptor (FPR) Agonists" Chirality 25:400-408 ( 2013).
Ansel et al. Pharmaceutical Dosage Forms and Drug Delivery Systems, ( 2004).
Ansel et al., "Pharmaceutical Dosage Forms and Drug Delivery Systems" 6th Ed.:456-457 ( 1995).
Bastin et al., "Salt Selection and Optimisation Procedures for Pharmaceutical New Chemical Entities" Organic Process Research & Development 4:427-435 ( 2000).
Belloni et al., "IFN-α inhibits HBV transcription and replication in cell culture and in humanized mice by targeting the epigenetic regulation of the nuclear cccDNa minichromosome" J Clin Invest 122(2):529-537 (Feb. 2012).
Buster et al., "Peginterferon alpha-2b is safe and effective in HBeAg-Positive chronic hepatitis B patients with advanced fibrosis" Hepatology 46:388-394 ( 2007).

(Continued)

*Primary Examiner* — Venkataraman Balasubramanian
(74) *Attorney, Agent, or Firm* — Brian L. Buckwalter

(57) ABSTRACT

The invention provides novel compounds having the general formula:

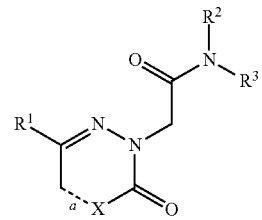

wherein $R^1$, $R^2$, $R^3$, X and a are as described in the description and in the claims, as well as or pharmaceutically acceptable salts thereof. The invention also contains compositions including the compounds and methods of using the compounds.

14 Claims, No Drawings

(56) References Cited

OTHER PUBLICATIONS

Chemical Abstracts Service Columbus Ohio US, CAS Registry Database, Database accession No. 1311923-37-1, CAS-RN 1311923-37-1. (XP002745283,) Jul. 7, 2011.
Chemical Abstracts Service, Columbus, Ohio, US;, CAS Registry Database, CAS-RN 1211102-07-6., Database accession No. 1211102-07-6 (XP002745295,) Mar. 17, 2010.
Chemical Abstracts Service, Columbus, Ohio, US;, CAS Registry Database, CAS-RNs 1252930-66-7, 1252922-95-4, 1252906-63-0, 1252903-52-8, 1252900-27-8, 1252898-61-5, 1252876-, Database accession No. 1252930-66-7 (XP002745289) Nov. 12, 2010.
Chemical Abstracts Service, Columbus, Ohio, US;, CAS Registry Database, CAS-RN 1294471-75-2., Database accession No. 1294471-75-2 May 13, 2011.
Chemical Abstracts Service, Columbus, Ohio, US;, CAS Registry Database, CAS-RN 1252314-15-0., Database accession No. 1252314-15-0 (XP002745290) Nov. 10, 2010.
Chemical Abstracts Service, Columbus, Ohio, US;, CAS Registry Database, CAS-RNs 1242011-18-2, 1242006-18-3, 1241997-52-3, 1241974-74-2., Database accession No. 1242011-18-2 (XP002745291) Sep. 17, 2010.
Chemical Abstracts Service, Columbus, Ohio, US;, Cas Registry Database, CAS-RN 1311923-37-1., Database accession No. 1311923-37-1 (XP002745284) May 20, 2011.
Chemical Abstracts Service, Columbus, Ohio, US;, CAS Registry Database, CAS-RN 12411156-12-6., Database accession No. 12411156-12-6 (XP002745282) Sep. 15, 2010.
Chemical Abstracts Service, Columbus, Ohio, US;, CAS Registry Database, CAS-RN 1289394-80-4., Database accession No. 1289394-80-4 (XP002745288) May 3, 2011.
Chemical Abstracts Service, Columbus, Ohio, US;, CAS Registry Database, CAS-RNs 1291859-50-1, 1291838-87-3., Database accession No. 1291859-50-1, 1291838-87-3 (XP002745287,) May 9, 2011.
Chemical Abstracts Service, Columbus, Ohio, US;, CAS Registry Database, CAS-RN 1211176-83-8., Database accession No. 1211176-83-8 (XP002745294) Mar. 18, 2010.
Chemical Abstracts Service, Columbus, Ohio, US;, CAS Registry Database, CAS-RN 1291866-61-9., Database accession No. 1291866-61-9 (XP002745286) May 9, 2011.
Chemical Abstracts Service, Columbus, Ohio, US;, CAS Registry Database, CAS-RN 1210247-97-4., Database accession No. 1210247-97-4 (XP002745296) Mar. 16, 2010.
Chemical Abstracts Service, Columbus, Ohio, US;, CAS Registry Database, CAS-RN 1240928-11-3., Database accession No. 1240928-11-3 (XP002745293) Sep. 14, 2010.
Fisicaro et al., "Antiviral intrahepatic T-cell responses can be restored by blocking programmed death-1 pathway in chronic hepatits B" Gastroenterology 138:682-693 ( 2010).
Geng et al., "Small-molecule inhibitors for the treatment of hepatitis B virus documented in patents" Mini Reviews in Medicinal Chemistry 13(5):749-776 (Apr. 1, 2013).
Gennaro et al. Remington: The Science and Practice of Pharmacy (Press), Philadelphia:Lippincott, Williams & Wilkins, ( 2000).
Hany S. Ibrahim et al., "Improvement of antibacterial activity of some sulfa drugs through linkage to certain phthalazin-1(2H)-one scaffolds" Eur J Med Chem 85:480-486 ( 2014).
Janssen et al., "Pegylated interferon alfa-2b alone or in combination with lamivudine for HBeAg-positive chronic hepatitis B: a randomised trial" LANCET 365:123-129 (Jan. 8, 2005).

Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring muti-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).
Mao et al., "Indoleamine 2,3-dioxygenase mediates the antiviral effect of gagamma interferon against hepatitis B virus in human hepatocyte-derived cells" J Virol 85(2):1048-1057 (Jan. 2011).
Mao et al., "Inhibition of hepatitis B virus replication by the host zinc finger antiviral protein" PLoS Pathogens 9(7 Suppl 1-18):e1003494 (Jul. 2013).
Marcellin et al., "Peginterferon alfa-2a alone, lamivudine alone, and the two in combination in patients with HBeAg-negative chronic hepatitis B" New E J Med 351(12):1206-1217 (Sep. 16, 2004).
Nayersina et al., "HLA A2 restricted cytotoxic T lymphocyte responses to multiple hepatitis B surface antigen epitopes during hepatitis B virus infection" J Immunol 150:4659-4671 (May 15, 1993).
Op den Brouw et al., "Hepatitis B virus surface antigen impairs myeloid dendritic cell function: a possible immune escape mechanism of hepatitis B virus" Immunol 126:280-290 ( 2008).
Quasdorff et al., "Control of hepatitis B virus at the level of transcription" J Viral Hepatitis 17:527-536 ( 2010).
Rowe, R. Handbook of Pharmaceutical Excipients Chicago:Pharmaceutical Press, ( 2005).
Schulze et al., "Hepatitis B virus infection initiates with a large surface protein-dependent binding heparan sulfate proteoglycans" Hepatology 46:1759-1768 ( 2007).
Shi et al., "Hepatitis B virus suppresses the functional interaction between natural killer cells and plasmacytoid dendritic cells" J Viral Hepatitis 19:e26-e33 ( 2012).
Wagdy M. Eldehna et al., "Design, synthesis and in vitro antitumor activity of novel N-substituted-4-phenyl/benzylphthalazin-1-ones" Eur J Med Chem 89:549-560 ( 2015).
Wieland et al., "Stealth and cunning: hepatitis B and hepatitis C viruses" J Virol 79(15):9369-9380 (Aug. 2005).
Woltman et al., "Hepatitis B virus lacks immune activating capacity, but actively inhibits plasmacytoid dendritic cell function" PLoS One 6(1 Suppl 1-14):e15324 (Jan. 2011).
Yan et al., "Molecular determinants of hepatitis B and D virus entry restriction in mouse sodium taurocholate cotransporting polypeptide" J Virol 87(14):7977-7991 (Jul. 2013).
Yu et al., "Design, Synthesis, and Biological Evaluation of Triazolopyrimidine Derivatives as Novel Inhibitors of Hepatitis B Virus Surface Antigen (H8sAg) Secretion" Journal of Medicinal Chemistry 54(16):5660-5670 (Aug. 25, 2011).
Chemical Abstracts, CAS Registry Database, CAS-RN: 1209785-65-8, (XP002745297) Mar. 15, 2010.
Other Database, (Database Registry, 2006, RN 898197-72-3, Retrieved from STN International) 2006.

* cited by examiner

PYRIDAZONES AND TRIAZINONES FOR TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors useful for treating HBV infection.

FIELD OF THE INVENTION

The present invention relates to novel pyridazones and triazinones having pharmaceutical activity, their manufacture, pharmaceutical compositions containing them and their potential use as medicaments.

The present invention relates to compounds of formula (I)

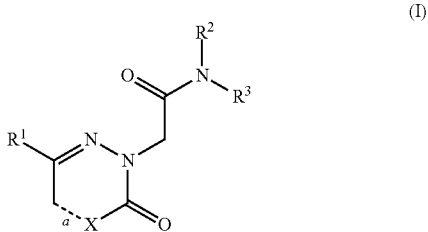

(I)

wherein $R^1$ to $R^3$, X and a are as described below, or to pharmaceutically acceptable salts thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat*. (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to novel compounds of formula (I)

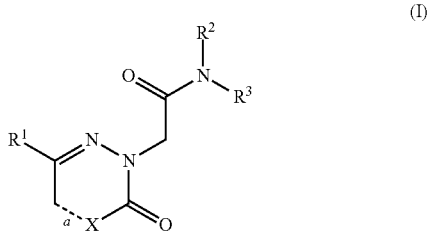

(I)

wherein
$R^1$ is phenyl; or phenyl substituted once or twice by $C_{1-6}$alkyl, halogen, trifluoromethyl or cyano;
$R^2$ is $C_{1-6}$alkyl;
$R^3$ is phenyl; or phenyl substituted once or twice by $C_{1-6}$alkyl, halogen, trifluoromethyl, cyano, $C_{1-6}$alkoxy, trifluoromethoxy, —C(O)—$C_{1-6}$alkoxy, or —C(O)—$NR^4R^5$ wherein one of $R^4$ and $R^5$ is hydrogen or $C_{1-6}$alkyl, and the other one is $C_{1-6}$alkyl or $C_{3-7}$cycloalkyl;
a is single bond when X is $CH_2$ or NH; or
a is double bond when X is CH or N;
or pharmaceutically acceptable salts thereof.

The invention also relates to their manufacture, medicaments based on a compound in accordance with the invention and their production as well as the use of compounds of formula I as HBsAg inhibitors. Accordingly, the compounds of formula I are useful for the treatment or prophylaxis of HBV infection.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" alone or in combination signifies a saturated, linear or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "trifluoromethyl" alone or in combination refers to the group —$CF_3$.

The term "trifluoromethoxy" alone or in combination refers to the group —O—$CF_3$.

The term "cyano" alone or in combination refers to the group —CN.

The term "halogen" means fluorine, chlorine, bromine or iodine. Halogen is particularly fluorine, chlorine or bromine.

The term "compound(s) of this invention" and "compound(s) of the present invention" refers to compounds of formula (I) and stereoisomers, solvates or salts thereof (e.g., pharmaceutically acceptable salts).

The term "substituent" denotes an atom or a group of atoms replacing a hydrogen atom on the parent molecule.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula (I).

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg
The present invention relates to (i) a compound of formula (I):
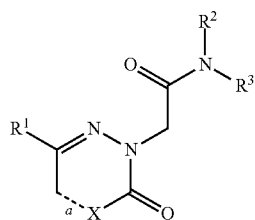

(I)

wherein $R^1$ is phenyl; or phenyl substituted once or twice by $C_{1-6}$alkyl, halogen, trifluoromethyl or cyano;

$R^2$ is $C_{1-6}$alkyl;

$R^3$ is phenyl; or phenyl substituted once or twice by $C_{1-6}$alkyl, halogen, trifluoromethyl, cyano, $C_{1-6}$alkoxy, trifluoromethoxy, —C(O)—$C_{1-6}$alkoxy, or —C(O)—$NR^4R^5$ wherein one of $R^4$ and $R^5$ is hydrogen or $C_{1-6}$alkyl, and the other one is $C_{1-6}$alkyl or $C_{3-7}$cycloalkyl;

a is single bond when X is $CH_2$ or NH; or a is double bond when X is CH or N;

or pharmaceutically acceptable salts thereof.

Another embodiment of present invention is (ii) a compound of formula (I) wherein $R^1$ is phenyl; or phenyl substituted once or twice by methyl, fluoro, chloro, bromo, trifluoromethyl or cyano;

$R^2$ is methyl;

$R^3$ is phenyl; or phenyl substituted once or twice by methyl, fluoro, chloro, trifluoromethyl, cyano, methoxy, trifluoromethoxy, methoxycarbonyl or —C(O)—$NR^4R^5$, wherein one of $R^4$ and $R^5$ is hydrogen, methyl or isopropyl, and the other one is isopropyl, pentanyl or cyclohexyl;

a is single bond when X is $CH_2$ or NH; or a is double bond when X is CH or N;

or pharmaceutically acceptable salts thereof.

Another embodiment of present invention is (iii) a compound of formula (I), wherein $R^1$ is phenyl substituted once or twice by halogen or trifluoromethyl.

A further embodiment of the present invention is (iv) a compound of formula (I) wherein $R^1$ is phenyl substituted once or twice by fluoro, chloro or trifluoromethyl.

Another embodiment of present invention is (v) a compound of formula (I) wherein $R^3$ is phenyl, or phenyl substituted once or twice by halogen or trifluoromethyl.

A further embodiment of present invention is (vi) a compound of formula (I) wherein $R^3$ is phenyl, or phenyl substituted once or twice by fluoro, chloro or trifluoromethyl.

Another embodiment of present invention is (vii) a compound of formula (I), wherein X is $CH_2$ or CH.

Another embodiment of present invention is (viii) a compound of formula (I), wherein $R^1$ is phenyl substituted once or twice by halogen or trifluoromethyl;

$R^2$ is $C_{1-6}$alkyl;

$R^3$ is phenyl, or phenyl substituted once or twice by halogen or trifluoromethyl;

a is single bond when X is $CH_2$; or a is double bond when X is CH;

or pharmaceutically acceptable salts thereof.

A further embodiment of present invention is (ix) a compound of formula (I), wherein $R^1$ is phenyl substituted once or twice by fluoro, chloro or trifluoromethyl;

$R^2$ is methyl;

$R^3$ is phenyl, or phenyl substituted once or twice by fluoro, chloro or trifluoromethyl;

a is single bond when X is $CH_2$; or a is double bond when X is CH;

or pharmaceutically acceptable salts thereof.

Particular compounds of formula (I) according to the invention are the following:

N-(4-Chlorophenyl)-2-[3-(4-chlorophenyl)-6-oxo-4,5-dihydropyridazin-1-yl]-N-methyl-acetamide;

2-[3-(4-Chlorophenyl)-6-oxo-4,5-dihydropyridazin-1-yl]-N-[4-fluoro-3-(trifluoromethyl)phenyl]-N-methyl-acetamide;

2-[3-(4-Chlorophenyl)-6-oxo-4,5-dihydropyridazin-1-yl]-N-[3-fluoro-4-(trifluoromethyl)phenyl]-N-methyl-acetamide;

N-(4-Chloro-3-fluoro-phenyl)-2-[3-(4-chlorophenyl)-6-oxo-4,5-dihydropyridazin-1-yl]-N-methyl-acetamide;

2-[3-(4-Chlorophenyl)-6-oxo-4,5-dihydropyridazin-1-yl]-N-(3-methoxyphenyl)-N-methyl-acetamide;

2-[3-(4-Chlorophenyl)-6-oxo-4, 5-dihydropyridazin-1-yl]-N-(4-fluorophenyl)-N-methyl-acetamide;

2-[3-(4-Chlorophenyl)-6-oxo-4,5-dihydropyridazin-1-yl]-N-methyl-N-(p-tolyl)acetamide;

2-[3-(4-Chlorophenyl)-6-oxo-4,5-dihydropyridazin-1-yl]-N-(3,4-dichlorophenyl)-N-methyl-acetamide;

2-[3-(4-Chlorophenyl)-6-oxo-4,5-dihydropyridazin-1-yl]-N-methyl-N-[4-(trifluoromethyl)phenyl]acetamide;

2-[3-(4-Chlorophenyl)-6-oxo-4,5-dihydropyridazin-1-yl]-N-(4-cyanophenyl)-N-methyl-acetamide;

Methyl 4-[[2-[3-(4-chlorophenyl)-6-oxo-4,5-dihydropyridazin-1-yl]acetyl]-methyl-amino]benzoate;

4-[[2-[3-(4-Chlorophenyl)-6-oxo-4,5-dihydropyridazin-1-yl]acetyl]-methyl-amino]-N,N-diisopropyl-benzamide;

2-[3-(4-Chlorophenyl)-6-oxo-4,5-dihydropyridazin-1-yl]-N-(2,4-difluorophenyl)-N-methyl-acetamide;

4-[[2-[3-(4-Chlorophenyl)-6-oxo-4,5-dihydropyridazin-1-yl]acetyl]-methyl-amino]-N-methyl-N-pentyl-benzamide;

4-[[2-[3-(4-Chlorophenyl)-6-oxo-4,5-dihydropyridazin-1-yl]acetyl]-methyl-amino]-N-cyclohexyl-benzamide;

2-[3-(4-Chlorophenyl)-6-oxo-4,5-dihydropyridazin-1-yl]-N-methyl-N-[4-(trifluoromethoxy)phenyl]acetamide;

2-[3-(4-Chlorophenyl)-6-oxo-4,5-dihydropyridazin-1-yl]-N-(3-fluorophenyl)-N-methyl-acetamide;

N-(3-Chlorophenyl)-2-[3-(4-chlorophenyl)-6-oxo-4,5-dihydropyridazin-1-yl]-N-methyl-acetamide;

2-[3-(4-Chlorophenyl)-6-oxo-4,5-dihydropyridazin-1-yl]-N-methyl-N-[3-(trifluoromethyl)phenyl]acetamide;

2-[3-(4-Chlorophenyl)-6-oxo-4,5-dihydropyridazin-1-yl]-N-(4-methoxyphenyl)-N-methyl-acetamide;

2-[3-(4-Chlorophenyl)-6-oxo-4,5-dihydropyridazin-1-yl]-N-methyl-N-(m-tolyl)acetamide;

2-[3-(4-Chloro-3-fluoro-phenyl)-6-oxo-4,5-dihydropyridazin-1-yl]-N-(4-fluorophenyl)-N-methyl-acetamide;

2-[3-(4-Chloro-3-fluoro-phenyl)-6-oxo-4,5-dihydropyridazin-1-yl]-N-(3-fluorophenyl)-N-methyl-acetamide;

2-[3-(4-Chloro-3-fluoro-phenyl)-6-oxo-4,5-dihydropyridazin-1-yl]-N-(3-chlorophenyl)-N-methyl-acetamide;

2-[3-(4-Chloro-3-fluoro-phenyl)-6-oxo-4,5-dihydropyridazin-1-yl]-N-methyl-N-[4-(trifluoromethyl)phenyl]acetamide;

2-[3-(4-Chloro-2-methyl-phenyl)-6-oxo-4,5-dihydro-pyridazin-1-yl]-N-(4-chlorophenyl)-N-methyl-acetamide;

2-[3-(4-Chloro-2-methyl-phenyl)-6-oxo-4,5-dihydro-pyridazin-1-yl]-N-(3-chlorophenyl)-N-methyl-acetamide;

2-[3-(4-Chloro-2-methyl-phenyl)-6-oxo-4,5-dihydro-pyridazin-1-yl]-N-(3-fluorophenyl)-N-methyl-acetamide;

2-[3-(4-Chloro-2-methyl-phenyl)-6-oxo-4,5-dihydro-pyridazin-1-yl]-N-methyl-N-[3-(trifluoromethyl)phenyl]acetamide;

2-[3-(2,4-Difluorophenyl)-6-oxo-4,5-dihydropyridazin-1-yl]-N-methyl-N-[4-(trifluoromethyl)phenyl]acetamide;

2-[3-(2, 4-Difluorophenyl)-6-oxo-4, 5-dihydropyridazin-1-yl]-N-methyl-N-[3-(trifluoromethyl)phenyl]acetamide;

2-[3-(2,4-Difluorophenyl)-6-oxo-4,5-dihydropyridazin-1-yl]-N-[4-fluoro-3-(trifluoromethyl)phenyl]-N-methyl-acetamide;

N-(4-Chlorophenyl)-2-[3-(2,4-difluorophenyl)-6-oxo-4,5-dihydropyridazin-1-yl]-N-methyl-acetamide;

2-[3-(2,4-Difluorophenyl)-6-oxo-4,5-dihydropyridazin-1-yl]-N-(3-fluorophenyl)-N-methyl-acetamide;

2-[3-(4-Fluoro-3-methyl-phenyl)-6-oxo-4,5-dihydro-pyridazin-1-yl]-N-methyl-N-[3-(trifluoromethyl)phenyl]acetamide;

2-[3-(4-Fluoro-3-methyl-phenyl)-6-oxo-4,5-dihydro-pyridazin-1-yl]-N-methyl-N-[4-(trifluoromethyl)phenyl]acetamide;

2-[3-(4-Fluoro-3-methyl-phenyl)-6-oxo-4,5-dihydro-pyridazin-1-yl]-N-[4-fluoro-3-(trifluoromethyl)phenyl]-N-methyl-acetamide;

2-[3-(4-Fluoro-3-methyl-phenyl)-6-oxo-4,5-dihydro-pyridazin-1-yl]-N-[3-fluoro-4-(trifluoromethyl)phenyl]-N-methyl-acetamide;

N-(3-Chlorophenyl)-N-methyl-2-[6-oxo-3-[4-(trifluoromethyl)phenyl]-4,5-dihydropyridazin-1-yl]acetamide;

N-Methyl-2-[6-oxo-3-[4-(trifluoromethyl)phenyl]-4,5-dihydropyridazin-1-yl]-N-[4-(trifluoromethyl)phenyl]acetamide;

N-Methyl-2-[6-oxo-3-[4-(trifluoromethyl)phenyl]-4,5-dihydropyridazin-1-yl]-N-[3-(trifluoromethyl)phenyl]acetamide;

N-(3-Fluorophenyl)-N-methyl-2-[6-oxo-3-[4-(trifluoromethyl)phenyl]-4,5-dihydropyridazin-1-yl]acetamide;

N-(4-Fluorophenyl)-N-methyl-2-[6-oxo-3-[4-(trifluoromethyl)phenyl]-4,5-dihydropyridazin-1-yl]acetamide;

N-(4-Chlorophenyl)-N-methyl-2-[6-oxo-3-[4-(trifluoromethyl)phenyl]-4,5-dihydropyridazin-1-yl]acetamide;

2-[3-(3,4-Di chlorophenyl)-6-oxo-4,5-dihydropyridazin-1-yl]-N-methyl-N-[4-(trifluoromethyl)phenyl]acetamide;

N-(4-Chlorophenyl)-2-[3-(3,4-di chlorophenyl)-6-oxo-4,5-dihydropyridazin-1-yl]-N-methyl-acetamide;

2-[3-(4-Fluorophenyl)-6-oxo-4,5-dihydropyridazin-1-yl]-N-methyl-N-phenyl-acetamide;

N-(4-Chlorophenyl)-2-[3-(4-fluorophenyl)-6-oxo-4,5-dihydropyridazin-1-yl]-N-methyl-acetamide;

2-[3-(4-Bromophenyl)-6-oxo-4,5-dihydropyridazin-1-yl]-N-methyl-N-phenyl-acetamide;

2-[3-(4-Bromophenyl)-6-oxo-4,5-dihydropyridazin-1-yl]-N-(4-chlorophenyl)-N-methyl-acetamide;

2-[3-(4-Bromophenyl)-6-oxo-4,5-dihydropyridazin-1-yl]-N-methyl-N-[4-(trifluoromethyl)phenyl]acetamide;

2-[3-(3, 4-Difluorophenyl)-6-oxo-4,5-dihydropyridazin-1-yl]-N-methyl-N-[3-(trifluoromethyl)phenyl]acetamide;

2-[3-(3,4-Difluorophenyl)-6-oxo-4,5-dihydropyridazin-1-yl]-N-methyl-N-[4-(trifluoromethyl)phenyl]acetamide;

N-(4-Chlorophenyl)-2-[3-(2,4-di chlorophenyl)-6-oxo-4,5-dihydropyridazin-1-yl]-N-methyl-acetamide;

N-(4-Chlorophenyl)-2-[3-(4-cyanophenyl)-6-oxo-4,5-dihydropyridazin-1-yl]-N-methyl-acetamide;

N-(4-Chlorophenyl)-N-methyl-2-[6-oxo-3-(p-tolyl)-4,5-dihydropyridazin-1-yl]acetamide;

N-(4-Chlorophenyl)-2-[3-(3-chlorophenyl)-6-oxo-4,5-dihydropyridazin-1-yl]-N-methyl-acetamide;

2-[3-(4-Chlorophenyl)-6-oxo-pyridazin-1-yl]-N-methyl-N-[4-(trifluoromethyl)phenyl]acetamide;

2-[3-(4-Chloro-3-fluoro-phenyl)-6-oxo-pyridazin-1-yl]-N-methyl-N-[4-(trifluoromethyl)phenyl]acetamide;

2-[3-(4-Chloro-2-fluoro-phenyl)-6-oxo-pyridazin-1-yl]-N-methyl-N-[4-(trifluoromethyl)phenyl]acetamide;

2-[3-(2-Chloro-6-fluoro-phenyl)-6-oxo-pyridazin-1-yl]-N-methyl-N-[4-(trifluoromethyl)phenyl]acetamide;

N-(4-Chlorophenyl)-2-[3-(4-chlorophenyl)-6-oxo-pyridazin-1-yl]-N-methyl-acetamide;

2-[6-(4-Chlorophenyl)-3-oxo-4,5-dihydro-1,2,4-triazin-2-yl]-N-methyl-N-[4-(trifluoromethyl)phenyl]acetamide;

N-(4-Chlorophenyl)-2-[6-(4-chlorophenyl)-3-oxo-1,2,4-triazin-2-yl]-N-methyl-acetamide;

or pharmaceutically acceptable salts thereof.

More particularly, the invention relates to the following compounds of formula (I):

2-[3-(4-Chlorophenyl)-6-oxo-4,5-dihydropyridazin-1-yl]-N-[3-fluoro-4-(trifluoromethyl)phenyl]-N-methyl-acetamide;

2-[3-(4-Chlorophenyl)-6-oxo-4,5-dihydropyridazin-1-yl]-N-(3,4-dichlorophenyl)-N-methyl-acetamide;

2-[3-(4-Chlorophenyl)-6-oxo-4,5-dihydropyridazin-1-yl]-N-methyl-N-[4-(trifluoromethyl)phenyl]acetamide;

2-[3-(4-Chloro-3-fluoro-phenyl)-6-oxo-4,5-dihydro-pyridazin-1-yl]-N-(3-fluorophenyl)-N-methyl-acetamide;

2-[3-(4-Chloro-3-fluoro-phenyl)-6-oxo-4,5-dihydro-pyridazin-1-yl]-N-(3-chlorophenyl)-N-methyl-acetamide;

2-[3-(4-Chloro-3-fluoro-phenyl)-6-oxo-4,5-dihydro-pyridazin-1-yl]-N-methyl-N-[4-(trifluoromethyl)phenyl]acetamide;

2-[3-(2,4-Difluorophenyl)-6-oxo-4,5-dihydropyridazin-1-yl]-N-methyl-N-[4-(trifluoromethyl)phenyl]acetamide;

N-(3-Chlorophenyl)-N-methyl-2-[6-oxo-3-[4-(trifluoromethyl)phenyl]-4,5-dihydropyridazin-1-yl]acetamide;

N-Methyl-2-[6-oxo-3-[4-(trifluoromethyl)phenyl]-4,5-dihydropyridazin-1-yl]-N-[3-(trifluoromethyl)phenyl]acetamide;

N-(3-Fluorophenyl)-N-methyl-2-[6-oxo-3-[4-(trifluoromethyl)phenyl]-4,5-dihydropyridazin-1-yl]acetamide;

2-[3-(3,4-Dichlorophenyl)-6-oxo-4,5-dihydropyridazin-1-yl]-N-methyl-N-[4-(trifluoromethyl)phenyl]acetamide;

N-(4-Chlorophenyl)-2-[3-(3,4-dichlorophenyl)-6-oxo-4,5-dihydropyridazin-1-yl]-N-methyl-acetamide;

2-[3-(3,4-Difluorophenyl)-6-oxo-4,5-dihydropyridazin-1-yl]-N-methyl-N-[3-(trifluoromethyl)phenyl]acetamide;

2-[3-(4-Chloro-3-fluoro-phenyl)-6-oxo-pyridazin-1-yl]-N-methyl-N-[4-(trifluoromethyl)phenyl]acetamide;

or pharmaceutically acceptable salts thereof.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula (I) in vivo are also within the scope of this invention.

Synthesis

The compounds of the present invention can be prepared by any conventional means. Suitable processes for synthesizing these compounds as well as their starting materials are provided in the schemes below and in the examples. All substituents, in particular, $R^1$ to $R^3$, X and a are as defined above unless otherwise indicated. Furthermore, and unless explicitly otherwise stated, all reactions, reaction conditions, abbreviations and symbols have the meanings well known to a person of ordinary skill in organic chemistry.

The compounds of the present invention can be prepared by any conventional means. Suitable processes for synthesizing these compounds as well as their starting materials are provided in the schemes below and in the examples. All substituents are as defined above unless otherwise indicated. Furthermore, and unless explicitly otherwise stated, all reactions, reaction conditions, abbreviations and symbols have the meanings well known to a person of ordinary skill in organic chemistry.

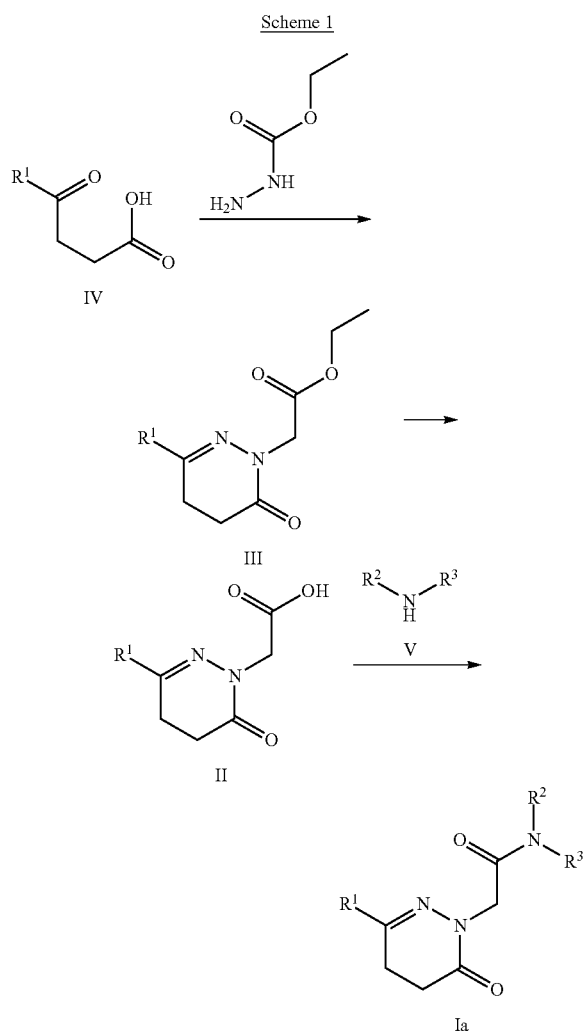

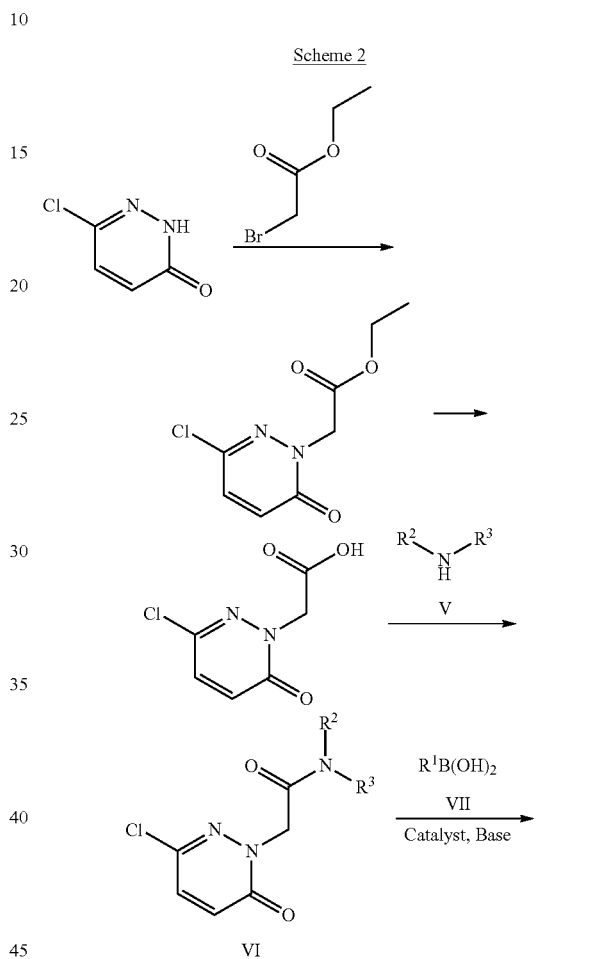

The compound of formula Ia can be prepared according to Scheme 1. Cyclocondensation reaction of benzoylpropionic acid derivatives IV with ethyl hydrazinoacetate hydrochloride in a solvent such as ethanol or 2-propanol gives dihydropyridazinone intermediate III. Sequential hydrolysis of III gives acid II. This reaction can be carried out in the presence of strong alkali base, such as sodium hydroxide, lithium hydroxide or potassium hydroxide in a mixed solvent of tetrahydrofuran/water or methanol/water. II can be converted into the amide derivatives Ia by a reaction with appropriate amine in an organic solvent such as methylene chloride or tetrahydrofuran with a dehydrating reagent, for example, HATU, PyBrOP or $T_3P$ in the presence of trialkylamine for example triethylamine.

The compound of formula Ib can be prepared according to Scheme 2. Alkylation of 3-chloro-1H-pyridazin-6-one with ethyl 2-bromoacetate gives ethyl 2-(3-chloro-6-oxo-pyridazin-1-yl)acetate using a base, for example potassium carbonate, cesium carbonate, or sodium hydride in an inert solvent such as dimethylformamide or acetonitrile. Hydrolysis of ethyl 2-(3-chloro-6-oxo-pyridazin-1-yl) acetate gives 2-(3-chloro-6-oxo-pyridazin-1-yl) acetic acid. This reaction can be carried out in the presence of a strong alkali base, such as sodium hydroxide, lithium hydroxide, or potassium hydroxide in a mixed solvent of tetrahydrofuran/ water or methanol/water. 2-(3-Chloro-6-oxo-pyridazin-1-yl) acetic acid can be converted into the amide derivatives VI by a reaction with appropriate amine V in an organic solvent, such as methylene chloride, with a dehydrating reagent, for example, HATU or $T_3P$ in the presence of trialkylamine, for example triethylamine. Palladium catalyzed Suzuki crossing coupling reaction of VI with arylboronic VII gives compounds Ib. Suitably the reaction is catalyzed by use of a transition state metal catalyst, such as palladium, for example $Pd(PPh_3)_4$.

Scheme 3

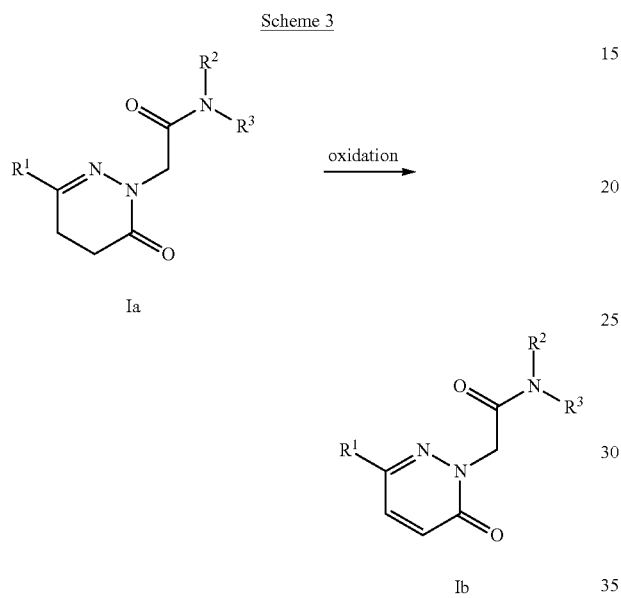

Alternatively, Ia may be oxidized to pyridazinone Ib by using an oxidizing agent for example $MnO_2$, $CuCl_2$, DDQ or selenium oxide.

Scheme 4

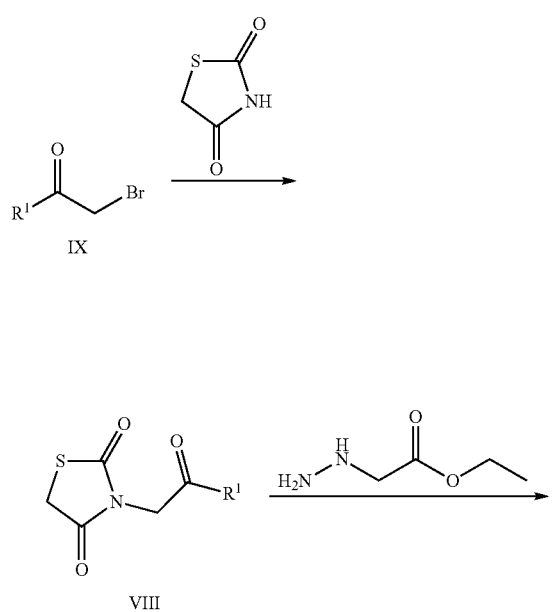

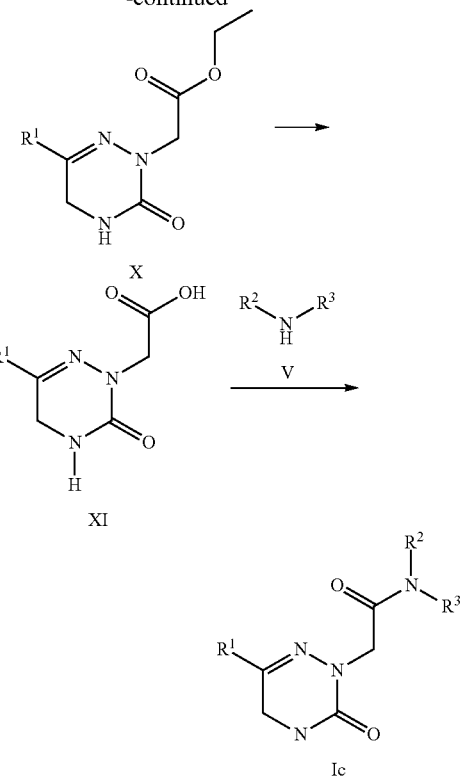

The compound of formula Ic can be prepared according to Scheme 4. Alkylation of 2,4-thiazolidinedione with $R^1COCH_2Br$ (IX) affords VIII by using a base, for example potassium carbonate, cesium carbonate, or sodium hydride in an inert solvent such as dimethylformamide or acetonitrile.

Reaction of VIII with ethyl hydrazinoacetate hydrochloride gives compounds X in a solvent such as ethanol or 2-propanol. Hydrolysis of X leads to compound XI. This reaction was carried out in a mixed solvent of methanol/water or tetrahydrofuran/water using a strong alkali base such as lithium hydroxide, sodium hydroxide, or potassium hydroxide. XI can be converted into the amide derivatives Ic by a reaction with appropriate amine V in an organic solvent such as methylene chloride with a dehydrating reagent, for example, HATU, PyBrOP or $T_3P$ in the presence of trialkylamine for example triethylamine.

Scheme 5

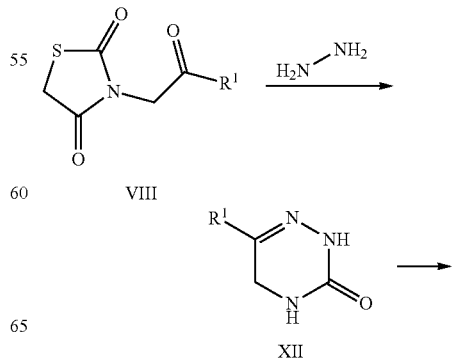

-continued

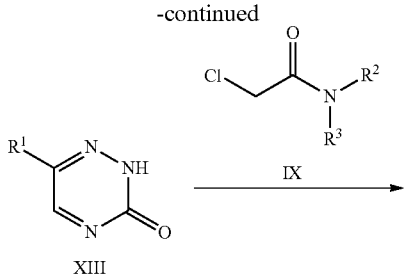

XIII

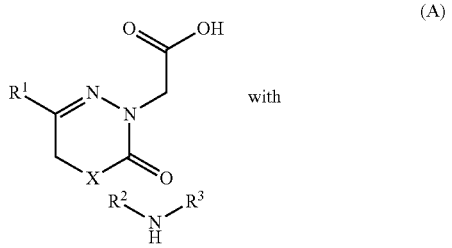

Id

The compound of formula Id can be prepared according to Scheme 5. Reaction of VIII with hydrazine hydrate gives compound XII. This reaction can be carried out in a solvent such as ethanol or 2-propanol under reflux. Oxidation of XII using 3-nitrobenzene sulfonic acid sodium salt affords compound XIII. Alkylation of XIII with IX affords Id by using a base, for example potassium carbonate, cesium carbonate, or sodium hydride in an inert solvent such as dimethylformamide or acetonitrile.

This invention also relates to a process for the preparation of a compound of formula (I) comprising one of the following steps:

(a) the reaction of a compound of formula (A)

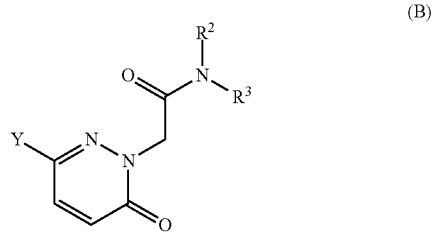

(A)

in the presence of a dehydrating reagent and a trialkylamine, wherein X is $CH_2$ or NH;

(b) the reaction of a compound of formula (B)

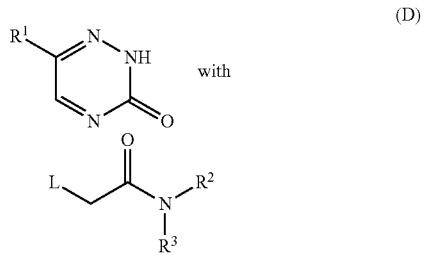

(B)

with $R^1B(OH)_2$ in the presence of a transition state metal catalyst, wherein Y is halogen;

(c) the reaction of a compound of formula (C)

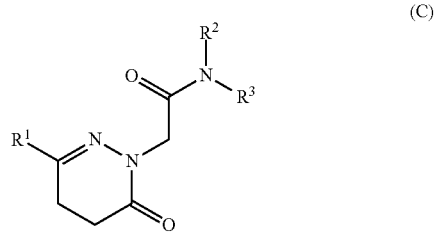

(C)

with an oxidizing reagent; or (d) the reaction of a compound of formula (D)

(D)

in the presence of a base in an inert solvent;
wherein $R^1$ to $R^3$ are defined above unless otherwise indicated.

In step (a), a dehydrating reagent can be for example HATU, PyBrOP or $T_3P$. A trialkylamine can be for example triethylamine.

In step (b), a transition state metal catalyst can be for example a palladium catalyst, in particular, $Pd(PPh_3)_4$.

In step (c), an oxidizing agent can be for example $MnO_2$, $CuCl_2$, DDQ or selenium oxide.

In step (d), a base can be for example potassium carbonate, cesium carbonate or sodium hydride. An inert solvent can be for example dimethylformamide or acetonitrile.

A compound of formula (I) when manufactured according to the above process is also an object of the invention.

Pharmaceutical Compositions and Administration

The invention also relates to a compound of formula (I) for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a stereoisomer or pharmaceutically acceptable salt thereof. In a further embodiment includes a pharmaceutical composition comprising a compound of Formula (I), or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula (I) for the inhibition of HBsAg production or secretion.

The invention relates to the use of a compound of formula (I) for the inhibition of HBV gene expression.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection, which method comprises administering an effective amount of a compound of Formula (I), a stereoisomer, tautomer, prodrug, conjugates or pharmaceutically acceptable salt thereof.

Combination Therapy

The compounds of the invention can be combined with other anti HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti HBV agents such as HBV RNA replication inhibitor, HBsAg secretion inhibitors, HBV capsid inhibitors, antisense oligomer, siRNA, HBV therapeutic vaccine, HBV prophylactic vaccine, HBV antibody therapy (monoclonal or polyclonal) and TLR 2, 3, 7, 8 and 9 agonists for the treatment or prophylaxis of HBV.

EXAMPLES

The invention will be more fully understood by reference to the following examples. They should not, however, be construed as limiting the scope of the invention.

Abbreviations used herein are as follows:

μL: microliter
μm: micrometer
μM; micromoles per liter
AcOK: potassium acetate
AcOH: acetic acid
Ar: argon
BSA: bovine serum albumin
BnBr: bromomethylbenzene
CDI: di(imidazol-1-yl)methanone
DCM: dichloromethane
DIPEA: N,N-diisopropylethylamine
DME: 1,2-dimethoxyethane
DMF: dimethylformamide
DMSO-d6: deuterated dimethylsulfoxide
EtOAc: ethyl acetate
g: gram
hrs: hours
HATU: 2-(7-aza-1H-benzotriazole-1-yl)-1,1,3,3-tetramethyluronium hexafluorophosphate
IC50: the half maximal inhibitory concentration
LC/MS: Liquid chromatography/mass spectrometry
m-CPBA: m-chloroperoxybenzoic acid
MeOH: methanol
METHANOL-$d_4$: perdeuteromethanol
M: molarity
mg: milligram
MHz: megahertz
min: minute
mins: minutes
mL: milliliter
mM: millimoles per liter
mm: millimeter
mmol: millimole
MS (ESI): mass spectroscopy (electron spray ionization)
nM: nanomoles per liter
nm: nanometer
NMR: nuclear magnetic resonance
$N_2$: nitrogen
rt: room temperature
PCC pyridinium chlorochromate
Pd/C: palladium on activated carbon
Pd(PPh$_3$)$_4$: tetrakis(triphenylphosphine)palladium
Pd(PPh$_3$)$_2$Cl$_2$: bis(triphenylphosphine)palladium(II) chloride
Pd(dppf)Cl$_2$: [1,1'-bis(diphenylphosphino)ferrocene]dichloropalladium(II)
PE or Pet: petroleum ether
prep-HPLC: preparative high performance liquid chromatography
PyBrOP: benzotriazol-1-yl-oxytripyrrolidinophosphonium hexafluorophosphate
Ruphos: Phosphine, [2',6'-bis(1-methylethoxy)[1,1'-biphenyl]-2-yl]dicyclohexyl-
SFC: supercritical fluid chromatography
T$_3$P: 1-Propylphosphonic acid cyclic anhydride
TEA: triethylamine
TFA: trifluoroacetic acid
THF: tetrahydrofuran
TLC: thin layer chromatography
δ: chemical shift
Xantphos: 9,9-dimethyl-4,5-bis(diphenylphosphino)xanthene General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;

Basic condition: A: 0.05% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Synthesis of Intermediates

Intermediate 1: N-Methyl-4-(trifluoromethyl) aniline

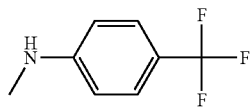

To a mixture of 4-trifluoromethylaniline (196 mg, 1.2 mmol), copper acetate (550 mg, 3.0 mmol) and pyridine (0.34 mL, 4.2 mmol) in dioxane (6 mL) was added methylboronic acid (181 mg, 3.0 mmol, Aldrich, Catalog number: 165335). The mixture was heated with stirring under reflux for 6 hours. The resulting mixture was filtered. The filtrate was concentrated under vacuum and purified by column chromatography to afford N-methyl-4-(trifluoromethyl)-aniline (150 mg, 70%). MS obsd. (ESI$^+$)[(M+H)$^+$]: 176

Intermediate 2: 3-Fluoro-N-methyl-4-(trifluoromethyl) aniline

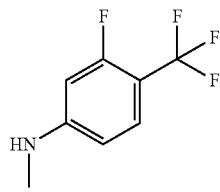

To a mixture of 3-fluoro-4-(trifluoromethyl)aniline (3.0 g, 16.7 mmol), copper acetate (7.6 g, 42 mmol) and pyridine (4.7 mL, 65 mmol) in dioxane (30 mL) was added methylboronic acid (2.5 g, 42 mmol, Aldrich, Catalog number: 165335). The mixture was heated with stirring under reflux for 6 hours. The resulting mixture was filtered and the filtrate was concentrated under vacuum and purified by column chromatography to afford 3-fluoro-N-methyl-4-(trifluoromethyl) aniline (900 mg, 28%). MS obsd. (ESI$^+$) [(M+H)$^+$]: 194.

Intermediate 3: 4-Chloro-3-fluoro-N-methyl-aniline

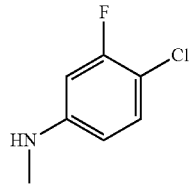

The title compound was prepared in analogy to Intermediate 1 by using 4-chloro-3-fluoro-aniline and methylboronic acid (Aldrich, Catalog number: 165335) instead of 4-trifluoromethylaniline and methylboronic acid. MS obsd. (ESI$^+$) [(M+H)$^+$]: 160.

Intermediate 4: 3-Methoxy-N-methyl-aniline

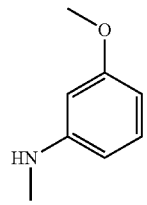

The title compound was prepared in analogy to Intermediate 1 by using 3-methoxyaniline and methylboronic acid (Aldrich, Catalog number: 165335) instead of 4-trifluoromethylaniline and methylboronic acid. MS obsd. (ESI$^+$)[(M+H)$^+$]: 138.

Intermediate 5: N-Methyl-3-(trifluoromethyl)aniline

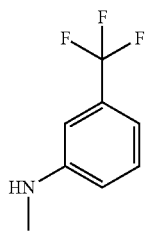

The title compound was prepared in analogy to Intermediate 1 by using 3-trifluoromethylaniline and methylboronic acid (Aldrich, Catalog number: 165335) instead of 4-trifluoromethylaniline and methylboronic acid. MS obsd. (ESI$^+$) [(M+H)$^+$]: 176.

Intermediate 6: 4-Fluoro-N-methyl-3-(trifluoromethyl)aniline

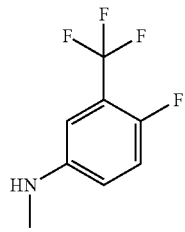

The title compound was prepared in analogy to Intermediate 1 by using 4-fluoro-3-(trifluoromethyl)aniline and methylboronic acid (Aldrich, Catalog number: 165335) instead of 4-trifluoromethylaniline and methylboronic acid. MS obsd. (ESI$^+$) [(M+H)$^+$]: 194.

Intermediate 7:
4-(4-Chloro-3-fluoro-phenyl)-4-oxo-butanoic acid

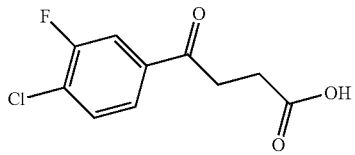 [SMILES: O=C(O)CCC(=O)c1ccc(Cl)c(F)c1]

To a mixture of magnesium ribbon (1.5 g, 61.7 mmol) and iodine (800 mg, 3.15 mmol) in anhydrous THF (10 mL), 4-bromo-1-chloro-2-fluorobenzene (627 mg, 2.7 mmol) was added. The mixture was heated to 60° C. until the reaction was initiated. Then 4-bromo-1-chloro-2-fluorobenzene (5.64 g, 27 mmol) was added slowly. After the addition was completed, the suspension was cooled to room temperature and stirred for 30 minutes to give the Grignard reagent.

To a solution of succinic anhydride (3.15 g, 31.5 mmol) in anhydrous THF (30 mL) was added dropwise the freshly prepared Grignard reagent. When the addition was completed, the resultant suspension was stirred at room temperature for 30 minutes. Afterwards, the reaction was quenched by cold water, then acidified with concentrated hydrochloric acid to pH=2. The ether layer was separated and extracted with 5% aqueous sodium hydroxide (50 mL) three times. The combined aqueous layers were washed with ether (100 mL). The aqueous layer was acidified with concentrated hydrochloric acid to pH=1 and extracted with ethyl acetate (100 mL) three times. Then the combined organic phases were washed with brine, dried over anhydrous magnesium sulfate and evaporated under vacuum to give the title compound as brown oil (4.87 g, 70%). MS obsd. (ESI$^+$) [(M+H)$^+$]: 231.

Intermediate 8:
4-(2,4-Dichlorophenyl)-4-oxo-butanoic acid

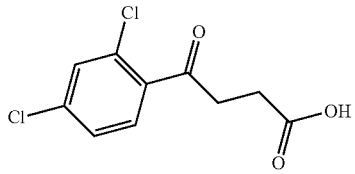 [SMILES: O=C(O)CCC(=O)c1ccc(Cl)cc1Cl]

A mixture of 1,3-dichlorobenzene (3.0 g, 20.4 mmol), succinic anhydride (2.45 g, 24.5 mmol, Aldrich, Catalog number: 239690) and aluminum chloride (5.97 g, 44.9 mmol) in 1, 2-dichloromethane (20 mL) was heated with stirring at 80° C. for 1 hour. The mixture was poured into aqueous hydrochloric acid (6 M, 100 mL). The resulting mixture was stirred for 15 minutes and then extracted with ethyl acetate. Then the organic phase was dried over sodium sulphate and concentrated under vacuum to afford 4-(2,4-dichlorophenyl)-4-oxo-butanoic acid (4.8 g, 96%). MS obsd. (ESI$^+$) [(M+H)$^+$]: 247.

Intermediate 9:
4-(2,4-Difluorophenyl)-4-oxo-butanoic acid

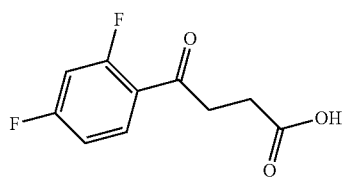 [SMILES: O=C(O)CCC(=O)c1ccc(F)cc1F]

The title compound was prepared in analogy to Intermediate 8 by using 1, 3-difluorobenzene (3.0 g, 26.3 mmol) and succinic anhydride (2.9 g, 29 mmol) instead of 1,3-dichlorobenzene (3.0 g, 20.4 mmol) and succinic anhydride (2.45 g, 24.5 mmol). The title compound was obtained as oil (4.5 g). MS obsd. (ESI$^+$) [(M+H)$^+$]: 215.

Intermediate 10:
4-(4-Chloro-2-methyl-phenyl)-4-oxo-butanoic acid

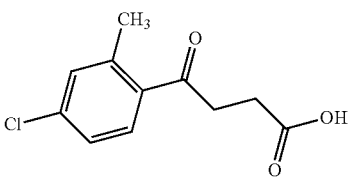

To a mixture of magnesium ribbon (525 mg, 22.0 mmol) and iodine (500 mg, 2.2 mmol) in anhydrous THF (100 mL), several drops of 1-bromo-4-chloro-2-methyl-benzene were added. The mixture was heated to 60° C. until the reaction was initiated, and then 1-bromo-4-chloro-2-methyl-benzene (3.0 g, 15 mmol) was added slowly. After the addition was completed, the suspension was cooled to room temperature and stirred at room temperature for 30 minutes to give the Grignard reagent.

To a solution of succinic anhydride (2.2 g, 22.0 mmol) in anhydrous tetrahydrofuran (30 mL) was added dropwise the freshly prepared Grignard reagent. After the addition was completed, the resulting suspension was stirred at room temperature for 30 minutes, then quenched by cold water and acidized to pH=2 with concentrated hydrochloric acid. The ether layers were extracted with 5% aqueous sodium hydroxide (50 mL) three times. The combined aqueous phase was washed with ether (100 mL). The aqueous layers were acidized with concentrated hydrochloric acidized to pH=1 and extracted with ethyl acetate (100 mL) three times. The organic extracts were combined, washed with brine, dried over anhydrous magnesium sulfate and evaporated under vacuum to give 4-(4-chloro-2-methyl-phenyl)-4-oxo-butanoic acid as crude oil (3.3 g), which was used for next step reaction without further purification. MS obsd. (ESI$^+$) [(M+H)$^+$]: 227.

Intermediate 11:
4-(3,4-Difluorophenyl)-4-oxo-butanoic acid

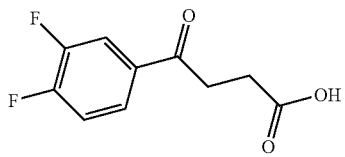 [SMILES: O=C(O)CCC(=O)c1ccc(F)c(F)c1]

To a mixture of magnesium ribbon (570 mg, 24 mmol), iodine (400 mg, 1.6 mmol) in anhydrous THF (100 mL), several drops of 4-bromo-1,2-difluoro-benzene were added. The mixture was heated to 60° C. until the reaction was initiated. Then 4-bromo-1,2-difluoro-benzene (3.0 g, 15.5 mmol) was added slowly to the mixture. After the addition was completed, the suspension was cooled from 60° C. to room temperature and stirred at room temperature for 30 minutes to give the Grignard reagent.

To a solution of succinic anhydride (1.55 g, 15.5 mmol) in anhydrous THF (30 mL) was added dropwise the freshly prepared Grignard reagent. After the addition was completed, the resulting suspension was stirred at room temperature for 30 minutes. The reaction was quenched by cold water, then acidified to pH=2 with hydrochloric acid (1M). Then the ether layers were extracted with 5% aqueous sodium hydroxide (50 mL) three times. The combined aqueous phase was washed with ether (100 mL). The aqueous layers were acidified with concentrated hydrochloric acid to pH=1 and extracted with ethyl acetate (100 mL) three times. The organic extracts were washed with brine, dried over anhydrous magnesium sulfate and evaporated under vacuum to give 4-(3,4-difluorophenyl)-4-oxo-butanoic acid as an oil (2.3 g), which was used for next step reaction without further purification. MS obsd. (ESI$^+$) [(M+H)$^+$]: 215.

Intermediate 12:
4-(4-Fluoro-3-methyl-phenyl)-4-oxo-butanoic acid

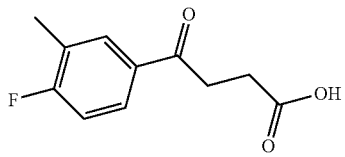

To a solution of magnesium ribbon (570 mg, 24 mmol) and iodine (400 mg, 1.57 mmol) in anhydrous THF (100 mL), several drops of 4-bromo-1-fluoro-2-methylbenzene were added. The mixture was heated to 60° C. until the reaction was initiated. Then 4-bromo-1-fluoro-2-methylbenzene (3.0 g, 15.9 mmol) was added slowly. After the addition was completed, the suspension was cooled to room temperature and stirred at room temperature for 30 minutes to give the Grignard reagent.

To a solution of succinic anhydride (1.55 g, 15.5 mmol) in anhydrous THF (30 mL) was added dropwise the freshly prepared Grignard reagent. After the addition is completed, the resulting suspension was stirred at room temperature for 30 minutes. Then the reaction was quenched with cold water and the resulting mixture was acidified to pH=2 with concentrated hydrochloric acid. The ether layers were extracted with 5% aqueous sodium hydroxide (50 mL) three times. The combined aqueous phases were washed with ether (100 mL), then acidized with concentrated hydrochloric acid to pH=1 and extracted with ethyl acetate (100 mL) three times. The organic extracts were washed with brine, dried over anhydrous magnesium sulfate and evaporated under vacuum to give 4-(4-fluoro-3-methyl-phenyl)-4-oxo-butanoic acid 4 as an oil (2.6 g), which was used for next step reaction without further purification. MS obsd. (ESI$^+$) [(M+H)$^+$]: 211.

Intermediate 13:
4-Oxo-4-[4-(trifluoromethyl)phenyl]butanoic acid

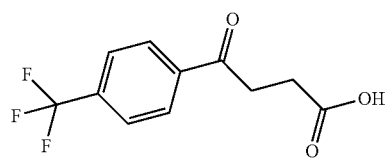 [SMILES: O=C(O)CCC(=O)c1ccc(C(F)(F)F)cc1]

To a mixture of magnesium ribbon (360 mg 15 mmol) and iodine (250 mg 1 mmol) in anhydrous THF (30 mL), several drops of 4-bromo-1-trifluroromethylbenzene were added, then the mixture was heated to 60° C. until the reaction was initiated, 4-bromo-1-trifluroromethylbenzene (2.25 g, 10 mmol) was added slowly. After the addition was completed, the suspension was cooled to room temperature and stirred at this temperature for another 30 minutes to give the Grignard reagent.

To a solution of succinic anhydride (1.2 g, 12 mmol) in anhydrous THF (30 mL) was added dropwise the freshly prepared Grignard reagent. When the addition was completed, the resulting suspension was stirred at room temperature for 30 minutes. Afterwards the reaction was quenched with cold water and the resulting mixture was acidified with concentrated hydrochloric acid to pH=2. The ether layer was extracted with 5% aqueous sodium hydroxide (50 mL) three times. The combined aqueous phases were washed with ether (100 mL), then acidized with concentrated hydrochloric acid to pH=1 and extracted with ethyl acetate (100 mL) three times. The combined organic extracts were washed with brine, dried over anhydrous magnesium sulfate and evaporated under vacuum to give 4-oxo-4-[4-(trifluoromethyl)phenyl]butanoic acid (1.1 g). MS obsd. (ESI$^+$) [(M+H)$^+$]: 247.

Intermediate 14:
4-(3,4-Dichlorophenyl)-4-oxo-butanoic acid

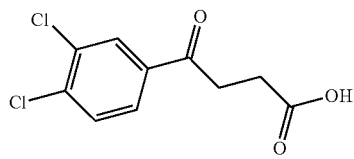 [SMILES: O=C(O)CCC(=O)c1ccc(Cl)c(Cl)c1]

To a mixture of 1,2-dichlorobenzene (22.0 g, 150 mmol) and tetrahydrofuran-2,5-dione (2.5 g, 25 mmol, Aldrich, Catalog number: 239690) was added aluminium chloride (1.0 g, 75 mmol) at room temperature. The mixture was heated with stirring at 60° C. for 5 hours. The mixture was Intermediate 15: 4-(3-Chlorophenyl)-4-oxo-butanoic acid

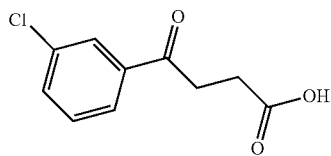 [SMILES: O=C(O)CCC(=O)c1cccc(Cl)c1]

To a solution of succinic anhydride (3.0 g, 30 mmol) in anhydrous tetrahydrofuran (30 mL) was added dropwise 3-chlorophenyl magnesium bromide in tetrahydrofuran (0.5 M, Aldrich, Catalog number: 563722). After the addition was completed, the resulting suspension was heated with stirring at 45° C. for 2 hours. Afterwards, the reaction was quenched by cold water, then acidified with concentrated hydrochloric acid to pH=2. The ether layer was separated and extracted with 5% aqueous sodium hydroxide (50 mL) three times. The combined aqueous phases were washed with ether (100 mL), then acidified with concentrated hydrochloric acid to pH=1 and extracted with ethyl acetate (100 mL) three times. The combined organic phases were washed with brine, dried over anhydrous magnesium sulfate and evaporated under vacuum to give the title compound as brown oil (4.0 g, 63%). MS obsd. (ESI$^+$) [(M+H)$^+$]: 213.

Preparative Examples

Example 1-1: N-(4-Chlorophenyl)-2-[3-(4-chlorophenyl)-6-oxo-4,5-dihydropyridazin-1-yl]-N-methylacetamide

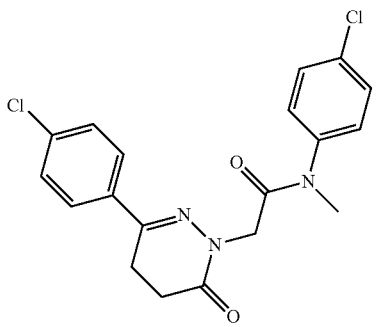 [SMILES: CN(C(=O)CN1N=C(c2ccc(Cl)cc2)CCC1=O)c1ccc(Cl)cc1]

Step 1: Preparation of ethyl 2-[3-(4-chlorophenyl)-6-oxo-4,5-dihydropyridazin-1-yl]acetate

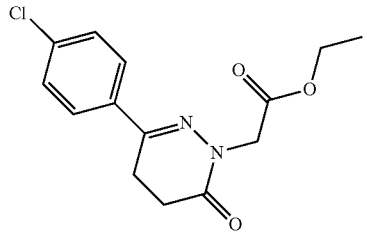 [SMILES: CCOC(=O)CN1N=C(c2ccc(Cl)cc2)CCC1=O]

To a mixture of 4-(4-dichlorophenyl)-4-oxo-butanoic acid (4.25 g, 20.0 mmol, Aldrich, catalog number: 439924-100G) and ethyl hydrazinoacetate hydrochloride (3.1 g, 20.0 mmol, Aldrich, Catalog number: 128279) in ethanol (28 mL) was added triethylamine (2.8 mL, 20.0 mmol). The mixture was heated with stirring under reflux for 6 hours. The resulting mixture was concentrated under vacuum and to the residue was added water (50 mL). The resulting mixture was extracted with ethyl acetate (50 mL) three times and the combined organic phases were dried over anhydrous sodium sulfate and filtered. The filtrate was concentrated under vacuum and the residue was purified by column chromatography to afford ethyl 2-[3-(4-chlorophenyl)-6-oxo-4,5-dihydropyridazin-1-yl]acetate (4.5 g, 76%). MS obsd. (ESI$^+$) [(M+H)$^+$]: 295.

Step 2: Preparation of 2-[3-(4-chlorophenyl)-6-oxo-4, 5-dihydropyridazin-1-yl]acetic acid

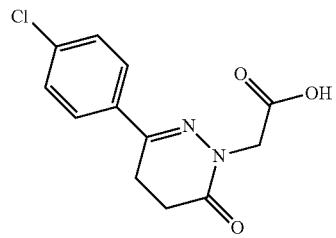 [SMILES: O=C(O)CN1N=C(c2ccc(Cl)cc2)CCC1=O]

To a solution of ethyl 2-[3-(4-dichlorophenyl)-6-oxo-4,5-dihydropyridazin-1-yl]acetate (2.95 g, 10 mmol) in tetrahydrofuran (50 mL) was added lithium hydroxide monohydrate (920 mg, 20 mmol) and water (50 mL). The resulting mixture was heated with stirring at 60° C. for 10 minutes. The resulting mixture was then concentrated under vacuum to remove the organic solvent. The resulting aqueous residue was acidified to pH=2 with aqueous hydrochloric acid (1 M), and extracted with ethyl acetate. The organic phase was dried over anhydrous sodium sulfate, filtered and concentrated under vacuum to afford 2-[3-(4-chlorophenyl)-6-oxo-4, 5-dihydropyridazin-1-yl]acetic acid (2.0 g, 76%). MS obsd. (ESI$^+$) [(M+H)$^+$]: 267.

Step 3: Preparation of N-(4-chlorophenyl)-2-[3-(4-chlorophenyl)-6-oxo-4,5-dihydropyridazin-1-yl]-N-methyl-acetamide

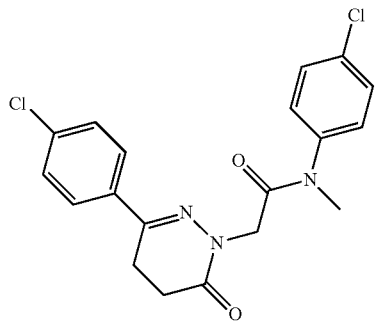

To a solution of 2-[3-(4-dichlorophenyl)-6-oxo-4,5-dihydropyridazin-1-yl]acetic acid (94 mg, 0.35 mmol), 4-chloro-N-methylaniline (49 mg, 0.35 mmol, Aldrich, Catalog number: 210358) and triethylamine (106 mg, 1.1 mmol) in dichloromethane (3 mL) was added 1-propylphosphonic acid cyclic anhydride (50 wt. % soln. in ethyl acetate, 445 mg, 0.7 mmol, Alfa Aesar: Catalog number: L11911) at 0° C. The mixture was stirred at room temperature for 1 hour, and then quenched with water. The mixture was extracted with ethyl acetate and the organic phase was dried over anhydrous sodium sulfate, then filtered and concentrated under vacuum. The residue was purified by prep-HPLC to afford N-(4-chlorophenyl)-2-[3-(4-chlorophenyl)-6-oxo-4,5-dihydropyridazin-1-yl]-N-methyl-acetamide (70 mg, 51%). $^1$H NMR (400 MHz, CDCl$_3$): δ 7.65 (m, 2H). 7.45 (d, J=8.3 Hz, 2H), 7.28-7.36 (m, 5H), 4.36 (br. s., 2H), 3.29 (s, 3H), 2.98 (t, J=8.2 Hz, 2H), 2.64 (t, J=8.2 Hz, 2H). MS obsd. (ESI$^+$) [(M+H)$^+$]: 390

Example 1-2: 2-[3-(4-Chlorophenyl)-6-oxo-4,5-dihydropyridazin-1-yl]-N-[4-fluoro-3-(trifluoromethyl)phenyl]-N-methyl-acetamide

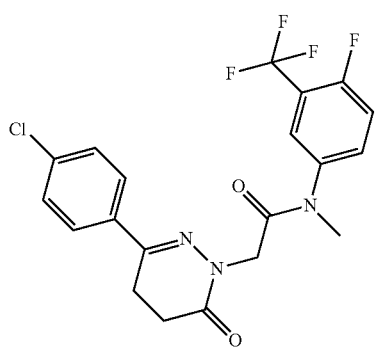 [SMILES: CN(C(=O)CN1N=C(c2ccc(Cl)cc2)CCC1=O)c1ccc(F)c(C(F)(F)F)c1]

The title compound was prepared in analogy to Example 1-1 by using 2-[3-(4-chlorophenyl)-6-oxo-4,5-dihydropyridazin-1-yl]acetic acid (100 mg, 0.38 mmol) and 4-fluoro-3-(trifluoromethyl)-N-methylaniline (130 mg, 0.59 mmol) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-[4-fluoro-3-(trifluoromethyl)phenyl]-N-methyl-acetamide was obtained as a colorless solid (70 mg). $^1$H NMR (400 MHz, CDCl$_3$): δ 7.62-7.66 (m, 4H), 7.36-7.40 (m, 3H), 4.35 (s, 2H), 3.32 (s, 3H), 3.0 (t, J=8.0 Hz, 2H), 2.32 (t, J=8.0 Hz, 2H). MS obsd. (ESI$^+$) [(M+H)$^+$]: 442.

Example 1-3: 2-[3-(4-Chlorophenyl)-6-oxo-4,5-dihydropyridazin-1-yl]-N-[3-fluoro-4-(trifluoromethyl)phenyl]-N-methyl-acetamide

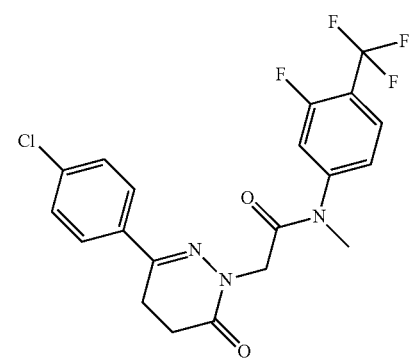 [SMILES: CN(C(=O)CN1N=C(c2ccc(Cl)cc2)CCC1=O)c1ccc(C(F)(F)F)c(F)c1]

The title compound was prepared in analogy to Example 1-1 by using 2-[3-(4-chlorophenyl)-6-oxo-4,5-dihydropyridazin-1-yl]acetic acid (80 mg, 0.3 mmol) and 3-fluoro-N-methyl-4-(trifluoromethyl)aniline (87 mg, 0.45 mmol) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-[3-fluoro-4-(trifluoromethyl)phenyl]-N-methyl-acetamide was obtained as solid (24 mg). $^1$H NMR (400 MHz, CDCl$_3$): δ 7.72 (t, J=8.0 Hz, 1H), 7.66 (m, 2H), 7.39 (d, J=12.0 Hz, 2H), 7.27-7.29 (m, 2H), 4.50 (br. s., 2H), 3.37 (s, 3H), 3.0 (t, J=8.2 Hz, 2H), 2.67 (t, J=8.2 Hz, 2H). MS obsd. (ESI$^+$) [(M+H)$^+$]: 442.

Example 1-4: N-(4-Chloro-3-fluoro-phenyl)-2-[3-(4-chlorophenyl)-6-oxo-4,5-dihydropyridazin-1-yl]-N-methyl-acetamide

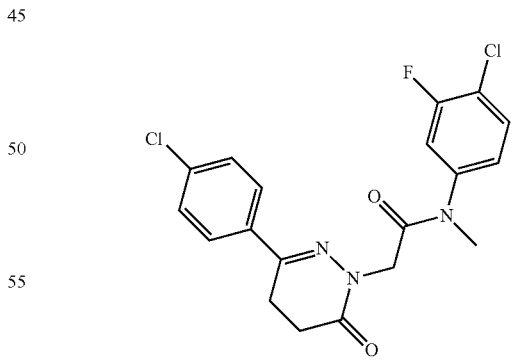

The title compound was prepared in analogy to Example 1-1 by using 2-[3-(4-chlorophenyl)-6-oxo-4,5-dihydropyridazin-1-yl]acetic acid (90 mg, 0.34 mmol) and 4-chloro-3-fluoro-N-methylaniline (80 mg, 0.50 mmol) instead of 2-[3-(4-chlorophenyl)-6-oxo-4,5-dihydropyridazin-1-yl] acetic acid and 4-chloro-N-methylaniline. N-(4-Chloro-3-fluorophenyl)-2-[3-(4-chlorophenyl)-6-oxo-4,5-dihydropyridazin-1-yl]-N-methyl-acetamide was obtained as a yellow solid (40 mg). $^1$H NMR (400 MHz, CDCl$_3$): δ 7.66 (m, 2H), 7.51 (t, J=8.2 Hz, 1H), 7.38 (m, 2H), 7.21 (m, 1H), 7.14 (m, 1H), 4.42 (s, 2H), 3.31 (s, 3H), 3.00 (t, J=8.0 Hz, 2H), 2.66 (t, J=8.0 Hz, 2H). MS obsd. (ESI$^+$) [(M+H)$^+$]: 408.

Example 1-5: 2-[3-(4-Chlorophenyl)-6-oxo-4,5-dihydropyridazin-1-yl]-N-(3-methoxyphenyl)-N-methyl-acetamide

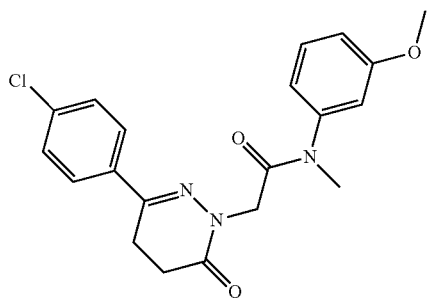 [SMILES: COc1cccc(N(C)C(=O)CN2N=C(c3ccc(Cl)cc3)CCC2=O)c1]

The title compound was prepared in analogy to Example 1-1 by using 2-[3-(4-chlorophenyl)-6-oxo-4,5-dihydropyridazin-1-yl]acetic acid (50 mg) and 3-methoxy-N-methylaniline (36 mg, Aldrich, Catalog number: 630934) instead of 2-[3-(4-chlorophenyl)-6-oxo-4,5-dihydropyridazin-1-yl] acetic acid and 4-chloro-N-methylaniline. 2-[3-(4-Chlorophenyl)-6-oxo-4,5-dihydropyridazin-1-yl]-N-(3-methoxyphenyl)-N-methyl-acetamide was obtained as a colorless solid (40 mg). $^1$H NMR (400 MHz, CDCl$_3$): δ 7.64 (d, J=8.0 Hz, 2H), 7.33-7.37 (m, 3H), 6.91 (dd, J=2.0, 8.0 Hz, 2H), 6.86 (t, J=2.0 Hz, 1H), 4.41 (s, 2H), 3.83 (s, 3H), 3.29 (s, 3H), 2.96 (t, J=8.0 Hz, 2H), 2.62 (t, J=8.0 Hz, 2H). MS obsd. (ESI$^+$) [(M+H)$^+$]: 386.

Example 1-6: 2-[3-(4-Chlorophenyl)-6-oxo-4,5-dihydropyridazin-1-yl]-N-(4-fluorophenyl)-N-methyl-acetamide

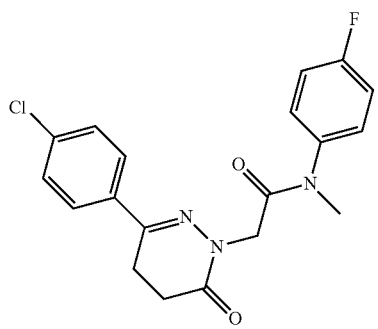 [SMILES: CN(C(=O)CN1N=C(c2ccc(Cl)cc2)CCC1=O)c1ccc(F)cc1]

The title compound was prepared in analogy to Example 1-1 by using 2-[3-(4-chlorophenyl)-6-oxo-4,5-dihydropyridazin-1-yl]acetic acid (100 mg) and 4-fluoro-N-methylaniline (46 mg, Aldrich, Catalog number: 223069) instead of 2-[3-(4-chlorophenyl)-6-oxo-4,5-dihydropyridazin-1-yl] acetic acid and 4-chloro-N-methylaniline. 2-[3-(4-Chlorophenyl)-6-oxo-4,5-dihydropyridazin-1-yl]-N-(4-fluorophenyl)-N-methyl-acetamide was obtained as a colorless solid (87 mg). $^1$H NMR (400 MHz, CDCl$_3$): δ 7.63 (d, J=8.0 Hz, 2H), 7.30-7.36 (m, 4H), 7.14 (t, J=8.0 Hz, 2H), 4.32 (s, 2H), 3.27 (s, 3H), 2.96 (t, J=8.0 Hz, 2H), 2.63 (t, J=8.0 Hz, 2H). MS obsd. (ESI$^+$) [(M+H)+]: 374.

Example 1-7: 2-[3-(4-Chlorophenyl)-6-oxo-4,5-dihydropyridazin-1-yl]-N-methyl-N-(p-tolyl)acetamide

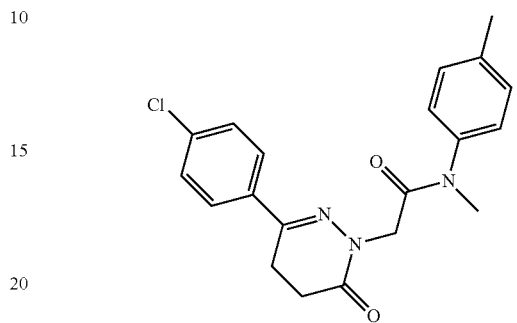

The title compound was prepared in analogy to Example 1-1 by using 2-[3-(4-chlorophenyl)-6-oxo-4,5-dihydropyridazin-1-yl]acetic acid (100 mg) and 4-methyl-N-methylaniline (45 mg, Aldrich, Catalog number: 494208-25) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-methyl-N-(p-tolyl)acetamide was obtained as a colorless solid (61 mg). $^1$H NMR (400 MHz, CDCl$_3$): δ 7.63 (d, J=8.0 Hz, 2H), 7.34 (d, J=8.0 Hz, 2H), 7.19-7.24 (m, 4H), 3.27 (s, 3H), 4.35 (s, 2H), 2.96 (t, J=8.0 Hz, 2H), 2.62 (t, J=8.0 Hz, 2H), 2.38 (s, 3H). MS obsd. (ESI$^+$) [(M+H)$^+$]: 370.

Example 1-8: 2-[3-(4-Chlorophenyl)-6-oxo-4,5-dihydropyridazin-1-yl]-N-(3,4-dichlorophenyl)-N-methyl-acetamide

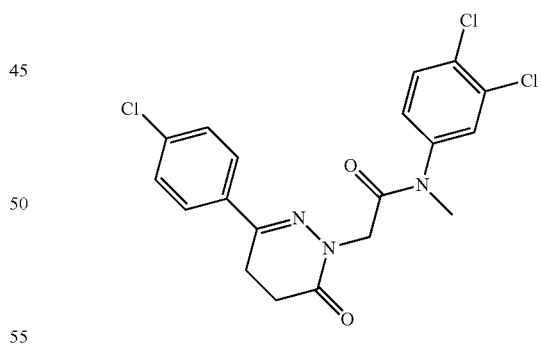

The title compound was prepared in analogy to Example 1-1 by using 2-[3-(4-chlorophenyl)-6-oxo-4,5-dihydropyridazin-1-yl]acetic acid (100 mg) and 3, 4-dichloro-N-methylaniline (65 mg, Aldrich, Catalog number: 569267) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-(3,4-dichlorophenyl)-N-methyl-acetamide was obtained as a colorless solid (83 mg). $^1$H NMR (400 MHz, CDCl$_3$): δ 7.63 (d, J=8.0 Hz, 2H), 7.53 (d, J=8.0 Hz, 1H), 7.47 (d, J=2.0 Hz, 1H), 7.36 (d, J=8.2 Hz, 2H), 7.22 (dd, J=4.0, 8.0

Hz, 1H), 3.28 (s, 3H), 4.38 (s, 2H), 2.97 (t, J=8.0 Hz, 2H), 2.63 (t, J=8.0 Hz, 2H). MS obsd. (ESI⁺) [(M+H)⁺]: 424.

Example 1-9: 2-[3-(4-Chlorophenyl)-6-oxo-4,5-dihydropyridazin-1-yl]-N-methyl-N-[4-(trifluoromethyl)phenyl]acetamide

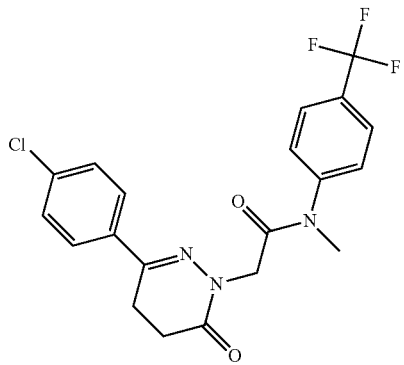 [SMILES: CN(C(=O)CN1N=C(c2ccc(Cl)cc2)CCC1=O)c1ccc(C(F)(F)F)cc1]

The title compound was prepared in analogy to Example 1-1 by using 2-[3-(4-chlorophenyl)-6-oxo-4,5-dihydropyridazin-1-yl]acetic acid (94 mg) and 4-trifluoromethyl-N-methylaniline (62 mg, Aldrich, Catalog number: 665843) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-methyl-N-[4-(trifluoromethyl)phenyl]acetamide was obtained as a solid (47 mg). ¹H NMR (400 MHz, CDCl₃): δ 7.73 (d, J=8.0 Hz, 2H), 7.63 (d, J=8.0 Hz, 2H), 7.48 (d, J=8.0 Hz, 2H), 7.35 (d, J=8.0 Hz, 2H), 4.40 (s, 2H), 3.33 (s, 3H), 2.96 (t, J=8.0 Hz, 2H), 2.63 (t, J=8.0 Hz, 2H). MS obsd. (ESI⁺) [(M+H)⁺]: 424.

Example 1-10: 2-[3-(4-Chlorophenyl)-6-oxo-4,5-dihydropyridazin-1-yl]-N-(4-cyanophenyl)-N-methyl-acetamide

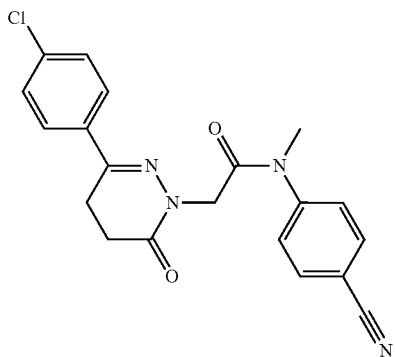 [SMILES: CN(C(=O)CN1N=C(c2ccc(Cl)cc2)CCC1=O)c1ccc(C#N)cc1]

The title compound was prepared in analogy to Example 1-1 by using 2-[3-(4-chlorophenyl)-6-oxo-4,5-dihydropyridazin-1-yl]acetic acid (80 mg) and 4-cyano-N-methylaniline (40 mg, Aldrich, catalog number: 665843-5G) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-(4-cyanophenyl)-N-methyl-acetamide was obtained as a colorless solid (62 mg). ¹H NMR (400 MHz, CDCl₃): δ 7.75 (d, J=8.2 Hz, 2H), 7.63 (d, J=8.2 Hz, 2H), 7.48 (d, J=8.1 Hz, 2H), 7.35 (d, J=8.2 Hz, 2H), 4.44 (s, 2H), 3.34 (s, 3H), 2.97 (t, J=8.2 Hz, 2H), 2.63 (t, J=8.1 Hz, 2H). MS obsd. (ESI⁺) [(M+H)⁺]: 381.

Example 1-11: Methyl 4-[[2-[3-(4-chlorophenyl)-6-oxo-4,5-dihydropyridazin-1-yl]acetyl]-methyl-amino]benzoate

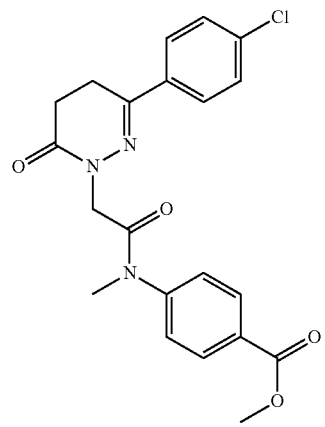 [SMILES: COC(=O)c1ccc(N(C)C(=O)CN2N=C(c3ccc(Cl)cc3)CCC2=O)cc1]

The title compound was prepared in analogy to Example 1-1 by using 2-[3-(4-chlorophenyl)-6-oxo-4,5-dihydropyridazin-1-yl]acetic acid (100 mg) and methyl 4-(methylamino)benzoate (Alfa Aesar, Catalog number: A13460) instead of 2-[3-(4-chlorophenyl)-6-oxo-4,5-dihydropyridazin-1-yl]acetic acid and 4-chloro-N-methylaniline. Methyl 4-[[2-[3-(4-chlorophenyl)-6-oxo-4,5-dihydropyridazin-1-yl]acetyl]-methyl-amino]benzoate was obtained as a colorless solid (10 mg). ¹H NMR (400 MHz, DMSO-d6): δ 8.02 (d, J=8.5 Hz, 2H), 7.75 (d, J=8.5 Hz, 2H), 7.57 (d, J=8.4 Hz, 2H), 7.51 (d, J=8.4 Hz. 2H), 4.46 (s, 2H), 3.86 (s, 3H), 3.28 (s, 3H), 2.95 (t, J=8.4 Hz, 2H), 2.51 (t, J=8.4 Hz, 2H). MS obsd. (ESI⁺) [(M+H)⁺]: 414.

Example 1-12: 4-[[2-[3-(4-Chlorophenyl)-6-oxo-4,5-dihydropyridazin-1-yl]acetyl]-methyl-amino]-N,N-diisopropyl-benzamide

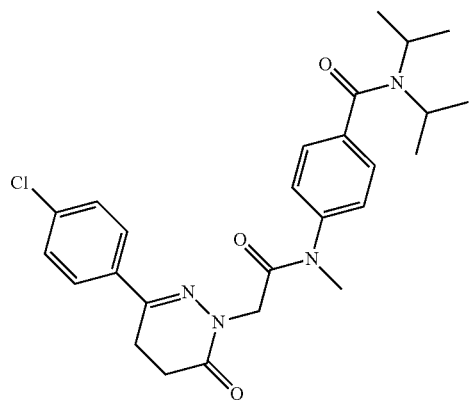 [SMILES: CC(C)N(C(=O)c1ccc(N(C)C(=O)CN2N=C(c3ccc(Cl)cc3)CCC2=O)cc1)C(C)C]

Step 1: Preparation of 4-[[2-[3-(4-chlorophenyl)-6-oxo-4,5-dihydropyridazin-1-yl]acetyl]-methyl-amino]benzoic acid

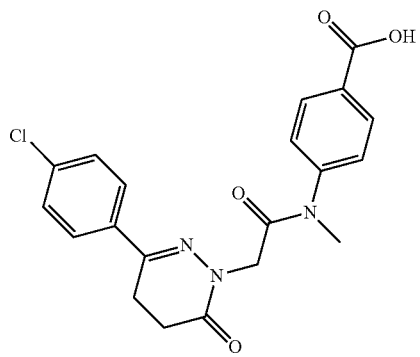 [SMILES: CN(C(=O)CN1N=C(c2ccc(Cl)cc2)CCC1=O)c1ccc(C(=O)O)cc1]

A mixture of methyl 4-[[2-[3-(4-chlorophenyl)-6-oxo-4,5-dihydropyridazin-1-yl]acetyl]-methyl-amino]benzoate (1.1 g, 2.4 mmol) (Example 1-11) and lithium hydroxide monohydrate (350 mg, 7.2 mmol) in tetrahydrofuran/water (10 mL, V/V=1/1) was heated with stirring at 60° C. for 10 minutes. The resulting mixture was concentrated under vacuum to remove the organic solvent and the aqueous residue was acidified to pH=2 with aqueous hydrochloric acid (1 M) and extracted with ethyl acetate. The organic phase was dried over anhydrous sodium sulfate, filtered and concentrated under vacuum to afford 4-[[2-[3-(4-chlorophenyl)-6-oxo-4,5-dihydropyridazin-1-yl]acetyl]-methyl-amino]benzoic acid (1.0 g, 99%).

Step 2: Preparation of 4-[[2-[3-(4-chlorophenyl)-6-oxo-4,5-dihydropyridazin-1-yl]acetyl]-methyl-amino]-N,N-diisopropyl-benzamide The title compound was prepared in analogy to Example 1-1 by using 4-[[2-[3-(4-chlorophenyl)-6-oxo-4,5-dihydropyridazin-1-yl]acetyl]-methyl-amino]benzoic acid (80 mg) and N,N-diisopropylamine (40 μL) in the presence of HATU instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. 4-[[2-[3-(4-Chlorophenyl)-6-oxo-4,5-dihydropyridazin-1-yl]acetyl]-methyl-amino]-N,N-diisopropyl-benzamide was obtained as a colorless solid (30 mg). $^1$H NMR (400 MHz, CDCl$_3$): δ 7.66 (m, 2H), 7.36-7.44 (m, 6H), 4.42 (s, 2H), 3.5-3.94 (m, 2H), 3.33 (s, 3H), 2.99 (d, J=8.1 Hz, 2H), 2.64 (t, J=16.1 Hz, 2H), 1.23-1.81 (m, 12H). MS obsd. (ESI$^+$) [(M+H)$^+$]: 482.

Example 1-13: 2-[3-(4-Chlorophenyl)-6-oxo-4,5-dihydropyridazin-1-yl]-N-(2,4-difluorophenyl)-N-methyl-acetamide

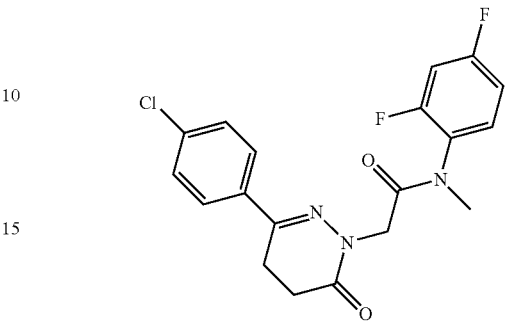

The title compound was prepared in analogy to Example 1-1 by using 2-[3-(4-chlorophenyl)-6-oxo-4,5-dihydropyridazin-1-yl]acetic acid (80 mg) and 2,4-difluoro-N-methyl-aniline (50 mg, Alfa Aesar, Catalog number: A15778) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-(2,4-difluorophenyl)-N-methyl-acetamide was obtained as a colorless solid (20 mg). $^1$H NMR (400 MHz, CDCl$_3$): δ 7.78 (d, J=8.0 Hz, 2H), 7.37-7.42 (m, 3H), 7.02 (m, 2H), 4.23-4.48 (m, 2H), 3.28 (s, 3H), 2.98 (m, 2H), 2.65 (m, 2H). MS obsd. (ESI$^+$) [(M+H)$^+$]: 392.

Example 1-14: 4-[[2-[3-(4-Chlorophenyl)-6-oxo-4,5-dihydropyridazin-1-yl]acetyl]-methyl-amino]-N-methyl-N-pentyl-benzamide

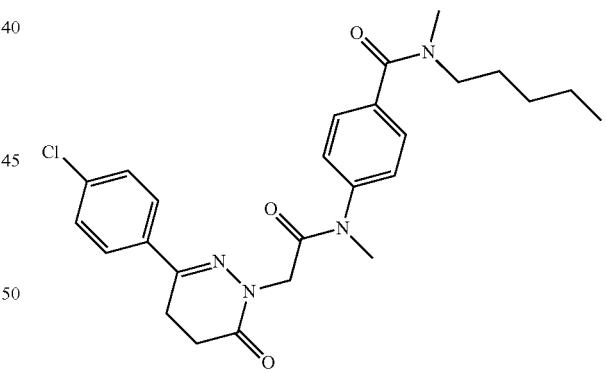

The title compound was prepared in analogy to Example 1-1 by using 4-[[2-[3-(4-chlorophenyl)-6-oxo-4,5-dihydropyridazin-1-yl]acetyl]-methyl-amino]benzoic acid (50 mg, Example 12, Step 1) and N-methylpentan-1-amine (20 μL) in the presence of HATU instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. 4-[[2-[3-(4-Chlorophenyl)-6-oxo-4,5-dihydropyridazin-1-yl]acetyl]-methyl-amino]-N-methyl-N-pentyl-benzamide was obtained as a colorless solid (40 mg). $^1$H NMR (400 MHz, CDCl$_3$): δ 7.66 (d, J=4.0 Hz, 2H), 7.51 (m, 2H), 7.37-7.41 (m, 4H), 4.41 (s, 2H), 3.72 (s, 1H), 3.34 (m, 4H), 3.11 (s, 2H), 2.99 (t, J=8.0 Hz, 2H), 2.65 (t, J=8.0

Hz, 2H), 2.05 (m, 2H), 1.68-1.81 (m, 3H), 1.45-1.48 (m, 2H), 0.86-1.68 (m, 7H). MS obsd. (ESI⁺) [(M+H)⁺]: 483.

Example 1-15: 4-[[2-[3-(4-Chlorophenyl)-6-oxo-4, 5-dihydropyridazin-1-yl]acetyl]-methyl-amino]-N-cyclohexyl-benzamide

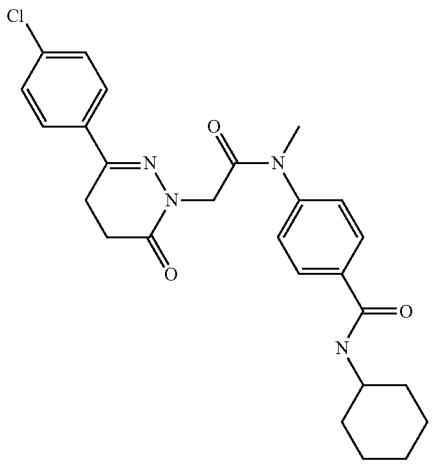 [SMILES: CN(C(=O)CN1N=C(c2ccc(Cl)cc2)CCC1=O)c1ccc(C(=O)NC2CCCCC2)cc1]

The title compound was prepared in analogy to Example 1-1 by using 4-[[2-[3-(4-chlorophenyl)-6-oxo-4,5-dihydro-pyridazin-1-yl]acetyl]-methyl-amino]benzoic acid (50 mg, Example 12, Step 1) and cyclohexylamine (70 µL) in the presence of HATU instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. 4-[[2-[3-(4-Chlorophenyl)-6-oxo-4,5-dihydro-pyridazin-1-yl]acetyl]-methyl-amino]-N-cyclohexyl-benzamide was obtained as colorless solid (40 mg). ¹H NMR (400 MHz, CDCl₃): δ 7.86 (d, J=8.1 Hz, 2H), 7.63 (d, J=8.1 Hz, 2H), 7.37-7.43 (m, 4H), 5.93 (d, J=4.0 Hz, 1H), 4.41 (s, 2H), 3.98 (m, 1H), 3.33 (s, 3H), 2.98 (d, J=8.1 Hz, 2H), 2.64 (t, J=8.2 Hz, 2H), 2.05 (m, 2H), 1.68-1.81 (m, 3H), 1.45-1.48 (m, 2H), 1.26-1.29 (m, 3H). MS obsd. (ESI⁺) [(M+H)⁺]: 481.

Example 1-16: 2-[3-(4-Chlorophenyl)-6-oxo-4,5-dihydropyridazin-1-yl]-N-methyl-N-[4-(trifluoromethoxy)phenyl]acetamide

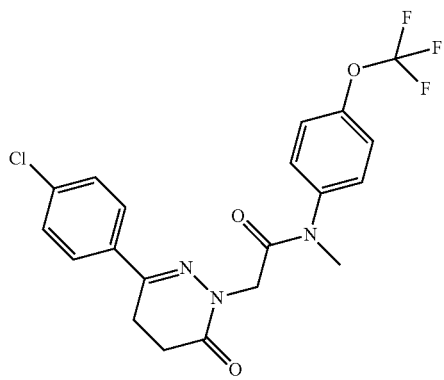 [SMILES: CN(C(=O)CN1N=C(c2ccc(Cl)cc2)CCC1=O)c1ccc(OC(F)(F)F)cc1]

The title compound was prepared in analogy to Example 1-1 by using 2-[3-(4-chlorophenyl)-6-oxo-4,5-dihydro-pyridazin-1-yl]acetic acid (80 mg) and 4-trifluoromethoxyl-N-methylaniline (80 mg, Fluorochem limited, Catalog number: i20_006837) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-methyl-N-[4-(trifluoromethoxy)phenyl]acetamide was obtained as a colorless solid. ¹H NMR (400 MHz, CDCl₃): δ 7.66 (m, 2H), 7.35 (m, 6H), 4.37 (s, 2H), 3.32 (s, 3H), 2.99 (t, J=8.0 Hz, 2H), 2.65 (t, J=8.0 Hz, 2H). MS obsd. (ESI⁺) [(M+H)⁺]: 440.

Example 1-17: 2-[3-(4-Chlorophenyl)-6-oxo-4,5-dihydropyridazin-1-yl]-N-(3-fluorophenyl)-N-methyl-acetamide

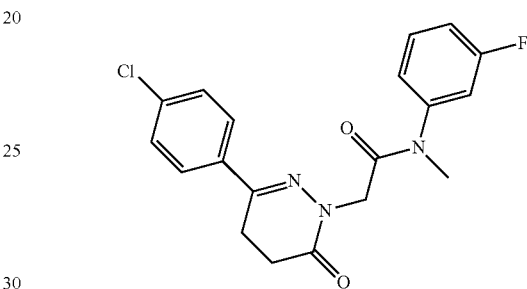

The title compound was prepared in analogy to Example 1-1 by using 2-[3-(4-chlorophenyl)-6-oxo-4,5-dihydro-pyridazin-1-yl]acetic acid (50 mg) and 3-fluoro-N-methyl-aniline (24 mg, Aldrich, Catalog number: 630969) instead of 2-[3-(4-chlorophenyl)-6-oxo-4,5-dihydropyridazin-1-yl] acetic acid and 4-chloro-N-methylaniline. 2-[3-(4-Chlorophenyl)-6-oxo-4,5-dihydropyridazin-1-yl]-N-(3-fluorophenyl)-N-methyl-acetamide was obtained as a colorless solid (50 mg). ¹H NMR (400 MHz, CDCl₃): δ 7.66 (d, J=8.0 Hz, 2H), 7.42-7.47 (m, 1H), 7.37 (d, J=8 Hz, 2H), 7.16-7.18 (m, 1H), 7.08-7.13 (m, 2H), 4.41 (s, 2H), 3.32 (s, 3H), 2.99 (t, J=8.0 Hz, 2H), 2.65 (t, J=8.0 Hz, 2H). MS obsd. (ESI⁺) [(M+H)⁺]: 374.

Example 1-18: N-(3-Chlorophenyl)-2-[3-(4-chlorophenyl)-6-oxo-4,5-dihydropyridazin-1-yl]-N-methyl-acetamide

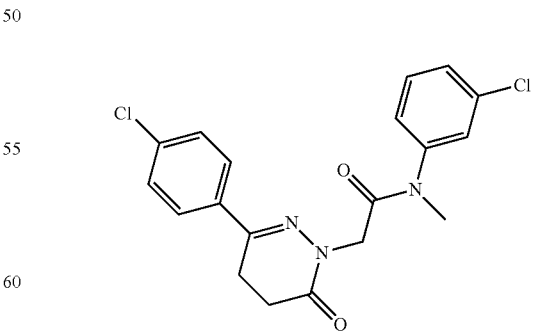

The title compound was prepared in analogy to Example 1-1 by using 2-[3-(4-chlorophenyl)-6-oxo-4,5-dihydro-pyridazin-1-yl]acetic acid (50 mg) and 3-chloro-N-methyl-aniline (27 mg, Aldrich, Catalog number: 532215) instead of 2-[3-(4-chlorophenyl)-6-oxo-4,5-dihydropyridazin-1-yl] acetic acid and 4-chloro-N-methylaniline. N-(3-Chlorophenyl)-2-[3-(4-chlorophenyl)-6-oxo-4,5-dihydropyridazin-1-yl]-N-methyl-acetamide was obtained as a colorless solid (52 mg). $^1$H NMR (400 MHz, CDCl$_3$): δ 7.66 (d, J=7.4 Hz, 2H), 7.36-7.44 (m, 5H), 7.27 (dt, J=4.0; 8.0 Hz, 1H), 4.41 (s, 2H), 3.31 (s, 3H), 2.96 (t, J=8.1 Hz, 2H), 2.62 (t, J=8.0 Hz, 2H). MS obsd. (ESI$^+$) [(M+H)$^+$]: 390.

Example 1-19: 2-[3-(4-Chlorophenyl)-6-oxo-4,5-dihydropyridazin-1-yl]-N-methyl-N-[3-(trifluoromethyl)phenyl]acetamide

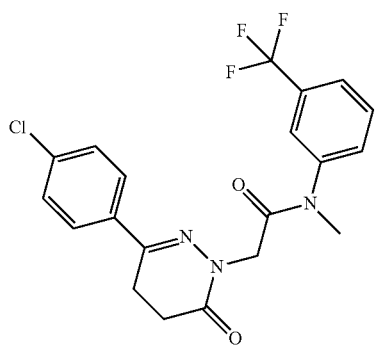 [SMILES: CN(C(=O)CN1N=C(c2ccc(Cl)cc2)CCC1=O)c1cccc(C(F)(F)F)c1]

The title compound was prepared in analogy to Example 1-1 by using 2-[3-(4-chlorophenyl)-6-oxo-4,5-dihydropyridazin-1-yl]acetic acid (100 mg) and 3-trifluoromethyl-N-methylaniline (110 mg, Fluorochem Limited, Catalog number, i20_045905) instead of 2-[3-(4-chlorophenyl)-6-oxo-4,5-dihydropyridazin-1-yl]acetic acid and 4-chloro-N-methylaniline. 2-[3-(4-Chlorophenyl)-6-oxo-4,5-dihydropyridazin-1-yl]-N-methyl-N-[3-(trifluoromethyl)phenyl]acetamide was obtained as a colorless solid (95 mg). $^1$H NMR (400 MHz, CDCl$_3$): δ 7.57-7.67 (m, 6H), 7.36-7.40 (m, 2H), 4.39 (s, 2H), 3.35 (s, 3H), 2.98 (t, J=8.0 Hz, 2H), 2.65 (t, J=8.0 Hz, 2H). MS obsd. (ESI$^+$) [(M+H)$^+$]: 424.

Example 1-20: 2-[3-(4-Chlorophenyl)-6-oxo-4,5-dihydropyridazin-1-yl]-N-(4-methoxyphenyl)-N-methyl-acetamide

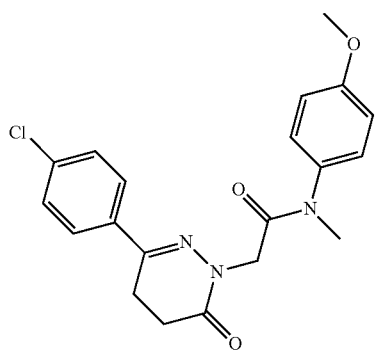 [SMILES: COc1ccc(N(C)C(=O)CN2N=C(c3ccc(Cl)cc3)CCC2=O)cc1]

The title compound was prepared in analogy to Example 1-1 by using 2-[3-(4-chlorophenyl)-6-oxo-4,5-dihydropyridazin-1-yl]acetic acid (50 mg) and 4-methoxy-N-methylaniline (26 mg, Aldrich, catalog number: 180033) instead of 2-[3-(4-chlorophenyl)-6-oxo-4,5-dihydropyridazin-1-yl] acetic acid and 4-chloro-N-methylaniline.

2-[3-(4-Chlorophenyl)-6-oxo-4,5-dihydropyridazin-1-yl]-N-(4-methoxyphenyl)-N-methyl-acetamide was obtained as a colorless solid (67 mg).

$^1$H NMR (400 MHz, CDCl$_3$): δ 7.63 (d, J=8.8 Hz, 2H), 7.33 (d, J=8.8 Hz, 2H), 7.23 (d, J=8.0 Hz, 2H), 6.94 (d, J=8.0 Hz, 2H), 4.33 (s, 2H), 3.82 (s, 3H), 3.25 (s, 3H), 2.95 (t, J=8.5 Hz, 2H), 2.62 (t, J=8.5 Hz, 2H). MS obsd. (ESI$^+$) [(M+H)$^+$]: 386.

Example 1-21: 2-[3-(4-Chlorophenyl)-6-oxo-4,5-dihydropyridazin-1-yl]-N-methyl-N-(m-tolyl)acetamide

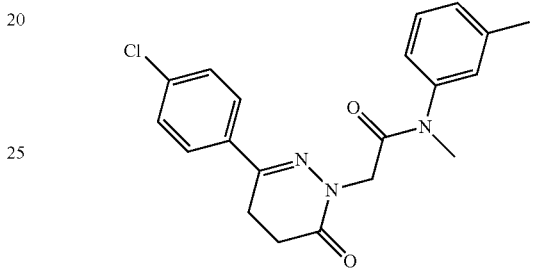

The title compound was prepared in analogy to Example 1-1 by using 2-[3-(4-chlorophenyl)-6-oxo-4,5-dihydropyridazin-1-yl]acetic acid (50 mg) and 3-methyl-N-methylaniline (23 mg, Aldrich, Catalog number: 593729) instead of 2-[3-(4-chlorophenyl)-6-oxo-4,5-dihydropyridazin-1-yl] acetic acid and 4-chloro-N-methylaniline. 2-[3-(4-Chlorophenyl)-6-oxo-4,5-dihydropyridazin-1-yl]-N-methyl-N-(m-tolyl)acetamide was obtained as a colorless solid (9 mg). $^1$H NMR (400 MHz, CDCl$_3$): δ 7.64 (d, J=8.1 Hz, 2H), 7.31-7.36 (m, 3H), 7.11-7.19 (m, 3H), 4.37 (s, 2H), 3.28 (s, 3H), 2.95 (t, J=8.2 Hz, 2H), 2.62 (t, J=8.2 Hz, 2H), 2.39 (s, 3H). MS obsd. (ESI$^+$) [(M+H)$^+$]: 370.

Example 1-22: 2-[3-(4-Chloro-3-fluoro-phenyl)-6-oxo-4,5-dihydropyridazin-1-yl]-N-(4-fluorophenyl)-N-methyl-acetamide

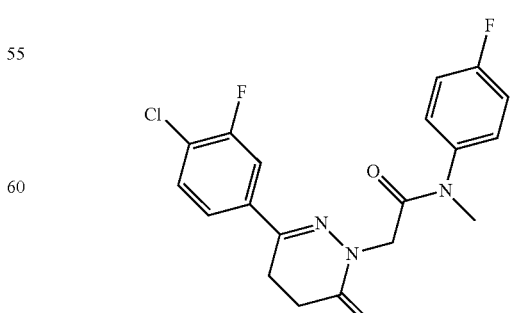

Step 1: Preparation of ethyl 2-[3-(4-chloro-3-fluoro-phenyl)-6-oxo-4,5-dihydropyridazin-1-yl]acetate

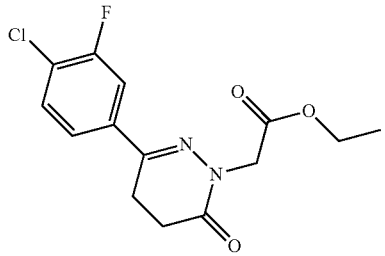 [SMILES: CCOC(=O)CN1N=C(c2ccc(Cl)c(F)c2)CCC1=O]

To a mixture of 4-(4-chloro-3-fluoro-phenyl)-4-oxo-butanoic acid (730 mg, 3.17 mmol) and ethyl hydrazinoacetate hydrochloride (500 mg, 3.2 mmol) in ethanol (28 mL) was added triethylamine (0.45 mL, 3.2 mmol). The mixture was heated with stirring under reflux for 6 hours. The resulting mixture was concentrated under vacuum. To the residue, water (20 mL) was added. The resulting mixture was extracted with ethyl acetate (20 mL) three times and the combined organic phases were dried over anhydrous sodium sulfate, filtered and concentrated under vacuum. The residue was purified by column chromatography to afford ethyl 2-[3-(4-chloro-3-fluoro-phenyl)-6-oxo-4,5-dihydro-pyridazin-1-yl]acetate (550 mg, 55.0%).

Step 2: Preparation of 2-[3-(4-chloro-3-fluoro-phenyl)-6-oxo-4,5-dihydropyridazin-1-yl]acetic acid

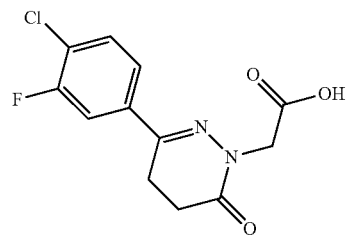 [SMILES: O=C(O)CN1N=C(c2ccc(Cl)c(F)c2)CCC1=O]

A mixture of ethyl 2-[3-(4-chloro-3-fluoro-phenyl)-6-oxo-4,5-dihydropyridazin-1-yl]acetate (550 mg, 1.76 mmol) and lithium hydroxide monohydrate (220 mg, 4.8 mmol) in tetrahydrofuran/water (50 mL, V/V=1/1) was heated with stirring at 60° C. for 10 minutes. The mixture was concentrated under vacuum to remove the organic solvent and the aqueous residue was acidized to pH=2 with hydrochloric acid (1 M), and then extracted with ethyl acetate. The organic phase was dried over anhydrous sodium sulfate, filtered and concentrated under vacuum to afford 2-[3-(4-chloro-3-fluoro-phenyl)-6-oxo-4,5-dihydropyridazin-1-yl] acetic acid (360 mg, 76%).

Step 3: Preparation of 2-[3-(4-chloro-3-fluoro-phenyl)-6-oxo-4,5-dihydropyridazin-1-yl]-N-(4-fluorophenyl)-N-methyl-acetamide

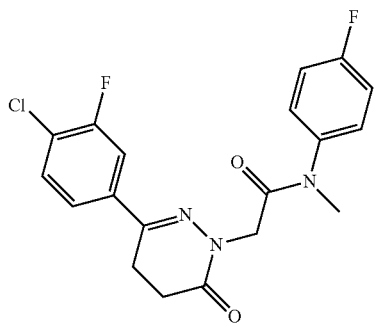 [SMILES: CN(C(=O)CN1N=C(c2ccc(Cl)c(F)c2)CCC1=O)c1ccc(F)cc1]

The title compound was prepared in analogy to Example 1-1 by using 2-[3-(4-chloro-3-fluorophenyl)-6-oxo-4,5-dihydropyridazin-1-yl]acetic acid (50 mg) and 4-fluoro-N-methylaniline (25 μL) instead of 2-[3-(4-chlorophenyl)-6-oxo-4,5-dihydropyridazin-1-yl]acetic acid and 4-chloro-N-methylaniline. 2-[3-(4-Chloro-3-fluoro-phenyl)-6-oxo-4,5-dihydropyridazin-1-yl]-N-(4-fluorophenyl)-N-methyl-acetamide was obtained as a colorless solid (12 mg). $^1$H NMR (400 MHz, DMSO-d6): δ 7.76 (d, J=4.0 Hz, 1H), 7.67 (m, 1H), 7.58 (m, 1H), 7.51 (s, 2H), 7.33 (m, 2H), 4.24 (s, 2H), 3.17 (s, 3H), 2.97 (t, J=8.0 Hz, 3H), 2.52 (m, 1H). MS obsd. (ESI$^+$) [(M+H)$^+$]: 392.

Example 1-23: 2-[3-(4-Chloro-3-fluoro-phenyl)-6-oxo-4,5-dihydropyridazin-1-yl]-N-(3-fluorophenyl)-N-methyl-acetamide

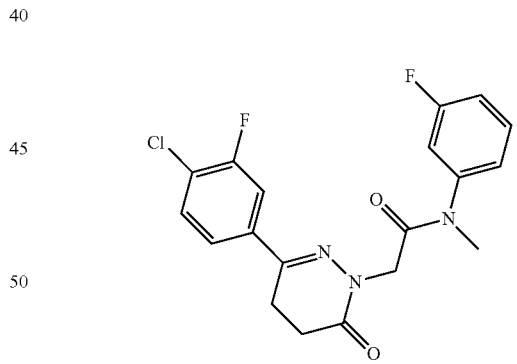

The title compound was prepared in analogy to Example 1-1 by using 2-[3-(4-chloro-3-fluorophenyl)-6-oxo-4,5-dihydropyridazin-1-yl]acetic acid (50 mg) and 3-fluoro-N-methylaniline (25 μL) instead of 2-[3-(4-chlorophenyl)-6-oxo-4,5-dihydropyridazin-1-yl]acetic acid and 4-chloro-N-methylaniline. 2-[3-(4-Chloro-3-fluoro-phenyl)-6-oxo-4,5-dihydropyridazin-1-yl]-N-(3-fluorophenyl)-N-methyl-acetamide was obtained as a colorless solid (3 mg). $^1$H NMR (400 MHz, MeOD): δ 7.69 (d, J=8.3 Hz, 1H), 7.52-7.60 (m, 3H), 7.21-7.30 (m, 3H), 4.43 (s, 2H), 3.35 (s, 3H), 3.05 (t, J=8.0 Hz, 2H), 2.64 (t, J=8.0 Hz, 2H). MS obsd. (ESI$^+$) [(M+H)$^+$]: 392.

Example 1-24: 2-[3-(4-Chloro-3-fluoro-phenyl)-6-oxo-4,5-dihydropyridazin-1-yl]-N-(3-chlorophenyl)-N-methyl-acetamide

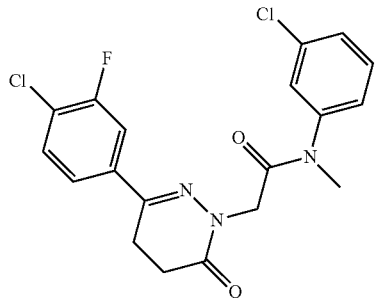 [SMILES: CN(C(=O)CN1N=C(c2ccc(Cl)c(F)c2)CCC1=O)c1cccc(Cl)c1]

The title compound was prepared in analogy to Example 1-1 by using 2-[3-(4-chloro-3-fluorophenyl)-6-oxo-4,5-dihydropyridazin-1-yl]acetic acid (50 mg) and 3-chloro-N-methylaniline (25 µL) instead of 2-[3-(4-chlorophenyl)-6-oxo-4,5-dihydropyridazin-1-yl]acetic acid and 4-chloro-N-methylaniline. 2-[3-(4-Chloro-3-fluoro-phenyl)-6-oxo-4,5-dihydropyridazin-1-yl]-N-(3-chlorophenyl)-N-methyl-acetamide was obtained as a colorless solid (2 mg). $^1$H NMR (400 MHz, DMSO-d6): δ 7.70 (d, J=8.3 Hz, 2H), 7.37-7.61 (m, 5H), 4.30 (s, 2H), 3.19 (s, 3H), 2.97 (t, J=8.0 Hz, 2H), 2.52 (t, J=8.0 Hz, 2H). MS obsd. (ESI$^+$) [(M+H)$^+$]: 408.

Example 1-25: 2-[3-(4-Chloro-3-fluoro-phenyl)-6-oxo-4,5-dihydropyridazin-1-yl]-N-methyl-N-[4-(trifluoromethyl)phenyl]acetamide

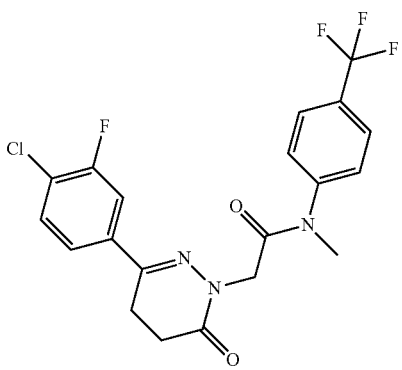 [SMILES: CN(C(=O)CN1N=C(c2ccc(Cl)c(F)c2)CCC1=O)c1ccc(C(F)(F)F)cc1]

The title compound was prepared in analogy to Example 1-1 by using 2-[3-(4-chloro-3-fluorophenyl)-6-oxo-4,5-dihydropyridazin-1-yl]acetic acid (50 mg) and 4-trifluoromethyl-N-methylaniline (31 mg) instead of 2-[3-(4-chlorophenyl)-6-oxo-4,5-dihydropyridazin-1-yl]acetic acid and 4-chloro-N-methylaniline. 2-[3-(4-Chloro-3-fluoro-phenyl)-6-oxo-4,5-dihydropyridazin-1-yl]-N-methyl-N-[4-(trifluoromethyl)phenyl]acetamide was obtained as a colorless solid (46 mg). $^1$H NMR (400 MHz, CDCl$_3$): δ 7.75 (m, 2H), 7.56 (d, J=1.2 Hz, 1H), 7.51 (d, J=8.0 Hz, 2H), 7.38 (m, 2H), 4.41 (s, 2H), 7.43 (m, 2H), 3.36 (s, 3H), 2.98 (t, J=8.0 Hz, 2H), 2.67 (t, J=8.0 Hz, 2H). MS obsd. (ESI$^+$) [(M+H)$^+$]: 442.

Example 1-26: 2-[3-(4-Chloro-2-methylphenyl)-6-oxo-4,5-dihydropyridazin-1-yl]-N-(4-chlorophenyl)-N-methyl-acetamide

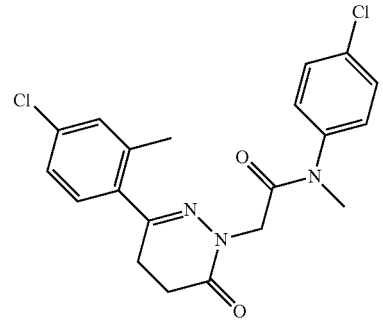 [SMILES: Cc1cc(Cl)ccc1C1=NN(CC(=O)N(C)c2ccc(Cl)cc2)C(=O)CC1]

Step 1: Preparation of ethyl 2-[3-(4-chloro-2-methyl-phenyl)-6-oxo-4,5-dihydropyridazin-1-yl]acetate

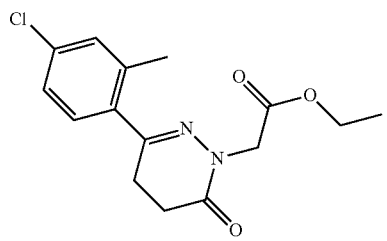 [SMILES: CCOC(=O)CN1N=C(c2ccc(Cl)cc2C)CCC1=O]

To a mixture of 4-(4-chloro-2-methylphenyl)-4-oxo-butanoic acid (3.3 g, 14.5 mmol, intermediate 10) and ethyl hydrazinoacetate hydrochloride (2.25 g, 14.5 mmol) in ethanol (20 mL) was added triethylamine (2.1 mL, 14.5 mmol). The mixture was heated with stirring under reflux for 6 hours. The resulting mixture was concentrated under vacuum. To the residue, water (50 mL) was added. The resulting mixture was extracted with ethyl acetate (50 mL) three times. The combined organic phases were dried over anhydrous sodium sulfate and concentrated under vacuum. The residue was purified by column chromatography to afford ethyl 2-[3-(4-chloro-2-methyl-phenyl)-6-oxo-4,5-dihydropyridazin-1-yl]acetate (1.5 g, 33.5%).

Step 2: Preparation of 2-[3-(4-chloro-2-methyl-phenyl)-6-oxo-4,5-dihydropyridazin-1-yl]acetic acid

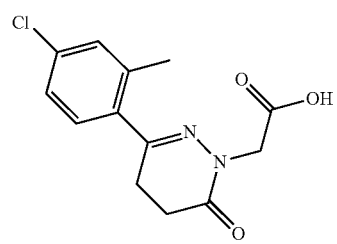 [SMILES: Cc1cc(Cl)ccc1C1=NN(CC(=O)O)C(=O)CC1]

A mixture of ethyl 2-[3-(4-chloro-2-methyl-phenyl)-6-oxo-4,5-dihydropyridazin-1-yl]acetate (1.5 g, 4.8 mmol)

and lithium hydroxide monohydrate (600 mg, 15.0 mmol) in tetrahydrofuran/water (15 mL, V/V=2/1) was heated with stirring at 60° C. for 1 hour. The mixture was concentrated under vacuum to remove the organic solvent and the aqueous residue was acidized to pH=2 with hydrochloric acid (1 M), then the mixture was extracted with ethyl acetate. The organic phase was dried over anhydrous sodium sulfate, filtered and concentrated under vacuum to afford 2-[3-(4-chloro-2-methyl-phenyl)-6-oxo-4,5-dihydropyridazin-1-yl] acetic acid (1.15 g, 85%).

Step 3: Preparation of 2-[3-(4-chloro-2-methyl-phenyl)-6-oxo-4,5-dihydropyridazin-1-yl]-N-(4-chlorophenyl)-N-methyl-acetamide

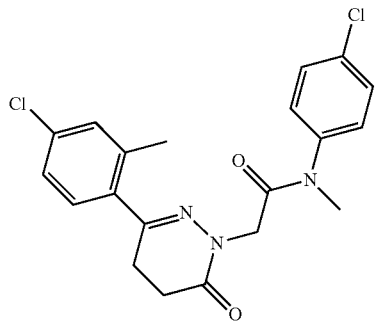 [SMILES: Cc1cc(Cl)ccc1C1=NN(CC(=O)N(C)c2ccc(Cl)cc2)C(=O)CC1]

The title compound was prepared in analogy to Example 1-1 by using 2-[3-(4-chloro-2-methylphenyl)-6-oxo-4,5-dihydropyridazin-1-yl]acetic acid (100 mg) and 4-chloro-N-methylaniline (50 μL) instead of 2-[3-(4-chlorophenyl)-6-oxo-4,5-dihydropyridazin-1-yl]acetic acid and 4-chloro-N-methylaniline. 2-[3-(4-Chloro-2-methyl-phenyl)-6-oxo-4,5-dihydropyridazin-1-yl]-N-(4-chlorophenyl)-N-methyl-acetamide was obtained as a colorless solid (14 mg). $^1$H NMR (400 MHz, DMSO-d6): δ 7.44-7.54 (m, 4H), 7.31-7.38 (m, 3H), 4.24 (s, 2H), 3.18 (s, 3H), 2.84 (t, J=8.2 Hz, 2H), 2.53 (t, J=8.2 Hz, 2H), 2.36 (s, 3H). MS obsd. (ESI$^+$) [(M+H)$^+$]: 404.

Example 1-27: 2-[3-(4-Chloro-2-methyl-phenyl)-6-oxo-4,5-dihydropyridazin-1-yl]-N-(3-chlorophenyl)-N-methyl-acetamide

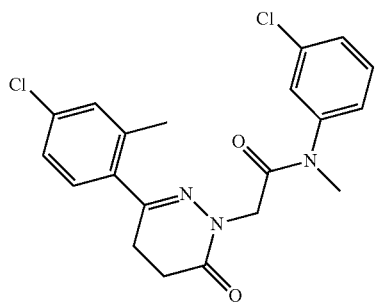 [SMILES: Cc1cc(Cl)ccc1C1=NN(CC(=O)N(C)c2cccc(F)c2)C(=O)CC1]

The title compound was prepared in analogy to Example 1-1 by using 2-[3-(4-chloro-2-methylphenyl)-6-oxo-4,5-dihydropyridazin-1-yl]acetic acid (100 mg) and 3-chloro-N-methylaniline (50 μL) in the presence of HATU instead of 2-[3-(4-chlorophenyl)-6-oxo-4,5-dihydropyridazin-1-yl] acetic acid and 4-chloro-N-methylaniline in the presence of 1-propylphosphonic acid cyclic anhydride. 2-[3-(4-Chloro-2-methylphenyl)-6-oxo-4,5-dihydropyridazin-1-yl]-N-(3-chlorophenyl)-N-methyl-acetamide was obtained as a colorless solid (14 mg). $^1$H NMR (400 MHz, DMSO-d6): δ 7.51 (s, 1H), 7.31-7.49 (m, 6H), 4.31 (s, 2H), 3.21 (s, 3H), 2.83 (t, J=8.2 Hz, 2H), 2.52 (t, J=8.2 Hz, 2H), 2.36 (s, 3H). MS obsd. (ESI$^+$) [(M+H)$^+$]: 404.

Example 1-28: 2-[3-(4-Chloro-2-methyl-phenyl)-6-oxo-4,5-dihydropyridazin-1-yl]-N-(3-fluorophenyl)-N-methyl-acetamide

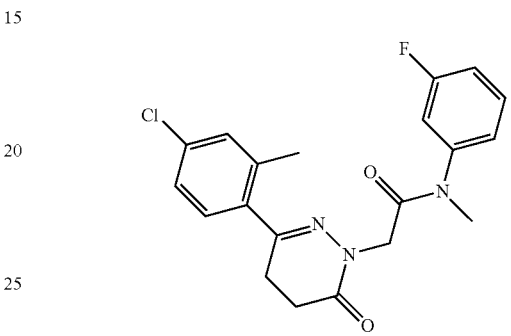

The title compound was prepared in analogy to Example 1-1 by using 2-[3-(4-chloro-2-methylphenyl)-6-oxo-4,5-dihydropyridazin-1-yl]acetic acid (100 mg) and 3-fluoro-N-methylaniline (50 μL) instead of 2-[3-(4-chlorophenyl)-6-oxo-4,5-dihydropyridazin-1-yl]acetic acid and 4-chloro-N-methylaniline. 2-[3-(4-Chloro-2-methyl-phenyl)-6-oxo-4,5-dihydropyridazin-1-yl]-N-(3-fluorophenyl)-N-methyl-acetamide was obtained as a colorless solid (10 mg). $^1$H NMR (400 MHz, DMSO-d6): δ 7.50 (m, 1H), 7.17-7.43 (m, 6H), 4.33 (s, 2H), 3.21 (s, 3H), 2.83 (t, J=8.0 Hz, 2H), 2.52 (t, J=8.0 Hz, 2H), 2.36 (s, 3H). MS obsd. (ESI$^+$) [(M+H)$^+$]: 388.

Example 1-29: 2-[3-(4-Chloro-2-methylphenyl)-6-oxo-4,5-dihydropyridazin-1-yl]-N-methyl-N-[3-(trifluoromethyl)phenyl]acetamide

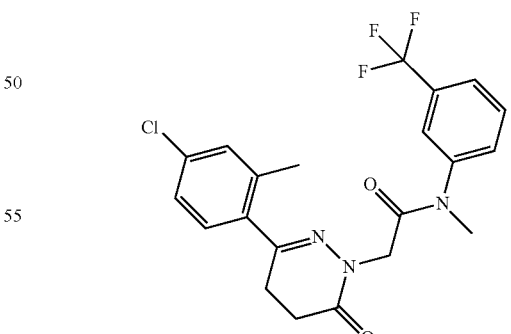

The title compound was prepared in analogy to Example 1-1 by using 2-[3-(4-chloro-2-methylphenyl)-6-oxo-4,5-dihydropyridazin-1-yl]acetic acid (100 mg) and 3-trifluoromethyl-N-methylaniline (110 mg) instead of 2-[3-(4-chlorophenyl)-6-oxo-4,5-dihydropyridazin-1-yl]acetic acid and 4-chloro-N-methylaniline. 2-[3-(4-Chloro-2-methyl-phenyl)-6-oxo-4,5-dihydropyridazin-1-yl]-N-methyl-N-[3-(trifluoromethyl)phenyl]acetamide was obtained as a colorless solid (30 mg). $^1$H NMR (400 MHz, CDCl$_3$): δ 7.54-7.65 (m, 4H), 7.20-7.28 (m, 3H), 4.34 (s, 2H), 3.34 (s, 3H), 2.88 (t, J=8.0 Hz, 2H), 2.65 (t, J=8.0 Hz, 2H), 2.41 (s, 3H). MS obsd. (ESI$^+$) [(M+H)$^+$]: 438.

Example 1-30: 2-[3-(2,4-Difluorophenyl)-6-oxo-4,5-dihydropyridazin-1-yl]-N-methyl-N-[4-(trifluoromethyl)phenyl]acetamide Step 1: Preparation of ethyl 2-[3-(2,4-difluorophenyl)-6-oxo-4,5-dihydropyridazin-1-yl]acetate

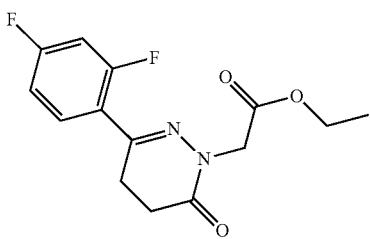 [SMILES: CCOC(=O)CN1N=C(c2ccc(F)cc2F)CCC1=O]

To a mixture of 4-(2,4-difluorophenyl)-4-oxo-butanoic acid (2.8 g, 13.1 mmol, Intermediate 9) and ethyl hydrazinoacetate hydrochloride (2.03 g, 13.1 mmol) in ethanol (20 mL) was added triethylamine (1.86 mL, 13.1 mmol). The mixture was heated with stirring under reflux for 6 hours. The resulting mixture was concentrated under vacuum. To the residue was added water (50 mL). The resulting mixture was extracted with ethyl acetate (50 mL) three times. The combined organic phases were dried over anhydrous sodium sulfate and concentrated under vacuum. The residue was purified by column chromatography to afford ethyl 2-[3-(2,4-difluorophenyl)-6-oxo-4,5-dihydropyridazin-1-yl]acetate (2.2 g, 55%).

Step 2: Preparation of 2-[3-(2,4-difluorophenyl)-6-oxo-4,5-dihydropyridazin-1-yl]acetic acid

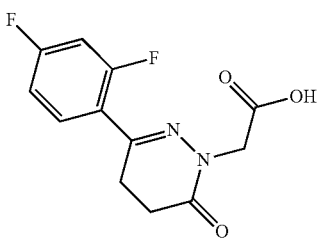 [SMILES: O=C(O)CN1N=C(c2ccc(F)cc2F)CCC1=O]

A mixture of ethyl 2-[3-(2,4-difluorophenyl)-6-oxo-4,5-dihydropyridazin-1-yl]acetate (2.03 g, 6.8 mmol) and lithium hydroxide monohydrate (1.44 mg 34 mmol) in tetrahydrofuran/water (50 mL, V/V=1/1) was heated with stirring at 60° C. for 1 hour. The mixture was concentrated under vacuum to remove the organic solvent and the aqueous residue was acidified to pH=2 with hydrochloric acid (1 M). The resulting mixture was then extracted with ethyl acetate. The organic phase was dried over anhydrous sodium sulfate, filtered and concentrated under vacuum to afford 2-[3-(2,4-difluorophenyl)-6-oxo-4,5-dihydropyridazin-1-yl] acetic acid (1.0 g, 99%).

Step 3: Preparation of 2-[3-(2,4-difluorophenyl)-6-oxo-4,5-dihydropyridazin-1-yl]-N-methyl-N-[4-(trifluoromethyl)phenyl]acetamide

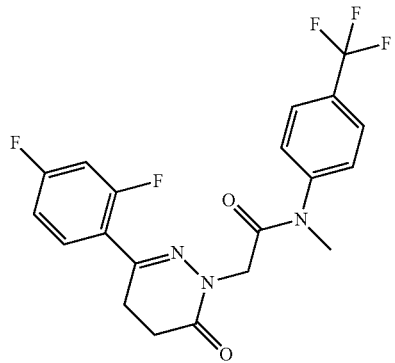 [SMILES: CN(C(=O)CN1N=C(c2ccc(F)cc2F)CCC1=O)c1ccc(C(F)(F)F)cc1]

The title compound was prepared in analogy to Example 1-1 by using 2-[3-(2,4-difluorophenyl)-6-oxo-4,5-dihydropyridazin-1-yl]acetic acid (100 mg) and 4-trifluoromethyl-N-methylaniline (110 mg) instead of 2-[3-(4-chlorophenyl)-6-oxo-4,5-dihydropyridazin-1-yl]acetic acid and 4-chloro-N-methylaniline. 2-[3-(2,4-Difluorophenyl)-6-oxo-4,5-dihydropyridazin-1-yl]-N-methyl-N-[4-(trifluoromethyl)phenyl]acetamide was obtained as a colorless solid (78 mg). $^1$H NMR (400 MHz, CDCl$_3$): δ 7.74 (d, J=8.0 Hz, 2H), 7.66 (m, 1H), 7.49 (d, J=8.3 Hz, 2H), 6.86-6.93 (m, 2H), 4.41 (s, 2H), 3.35 (s, 3H), 3.01 (t, J=8.0 Hz, 2H), 2.63 (t, J=8.0 Hz, 2H). MS obsd. (ESI$^+$) [(M+H)$^+$]: 426.

Example 1-31: 2-[3-(2, 4-Difluorophenyl)-6-oxo-4, 5-dihydropyridazin-1-yl]-N-methyl-N-[3-(trifluoromethyl)phenyl]acetamide

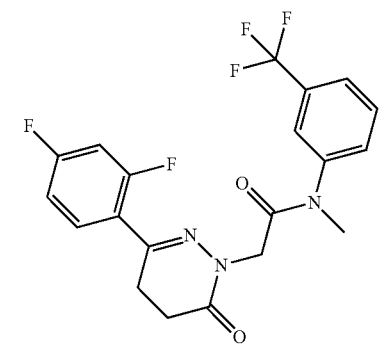 [SMILES: CN(C(=O)CN1N=C(c2ccc(F)cc2F)CCC1=O)c1cccc(C(F)(F)F)c1]

The title compound was prepared in analogy to Example 1-1 by using 2-[3-(2,4-difluorophenyl)-6-oxo-4,5-dihydropyridazin-1-yl]acetic acid (100 mg) and 3-trifluoromethyl-N-methylaniline (110 mg) instead of 2-[3-(4-chlorophenyl)-6-oxo-4,5-dihydropyridazin-1-yl]acetic acid and 4-chloro-N-methylaniline. 2-[3-(2, 4-Difluorophenyl)-6-oxo-4, 5-dihydropyridazin-1-yl]-N-methyl-N-[3-(trifluoromethyl) phenyl] acetamide was obtained as a colorless solid (50 mg). $^1$H NMR (400 MHz, CDCl$_3$): δ 7.56-7.65 (m, 5H), 6.83-6.95 (m, 2H), 4.37 (s, 2H), 3.35 (s, 3H), 3.01 (t, J=8.1 Hz, 2H), 2.63 (t, J=8.2 Hz, 2H). MS obsd. (ESI$^+$) [(M+H)$^+$]: 426.

Example 1-32: 2-[3-(2,4-Difluorophenyl)-6-oxo-4,5-dihydropyridazin-1-yl]-N-[4-fluoro-3-(trifluoromethyl)phenyl]-N-methyl-acetamide

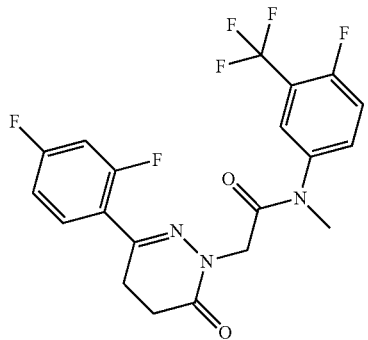 [SMILES: CN(C(=O)CN1N=C(c2ccc(F)cc2F)CCC1=O)c1ccc(F)c(C(F)(F)F)c1]

The title compound was prepared in analogy to Example 1-1 by using 2-[3-(2,4-difluorophenyl)-6-oxo-4,5-dihydropyridazin-1-yl] acetic acid (100 mg) and 4-fluoro-3-triflurormethyl-N-methylaniline (130 mg) instead of 2-[3-(4-chlorophenyl)-6-oxo-4,5-dihydropyridazin-1-yl]acetic acid and 4-chloro-N-methylaniline. 2-[3-(2,4-Difluorophenyl)-6-oxo-4,5-dihydropyridazin-1-yl]-N-[4-fluoro-3-(trifluoromethyl)phenyl]-N-methyl-acetamide was obtained as a colorless solid (30 mg). $^1$H NMR (400 MHz, CDCl$_3$): δ 7.57-7.65 (m, 3H), 7.33 (m, 1H), 6.84-6.95 (m, 2H), 4.33 (s, 2H), 3.32 (s, 3H), 3.02 (t, J=8.1 Hz, 2H), 2.64 (t, J=8.1 Hz, 2H). MS obsd. (ESI$^+$) [(M+H)$^+$]: 444.

Example 1-33: N-(4-Chlorophenyl)-2-[3-(2,4-difluorophenyl)-6-oxo-4,5-dihydropyridazin-1-yl]-N-methyl-acetamide

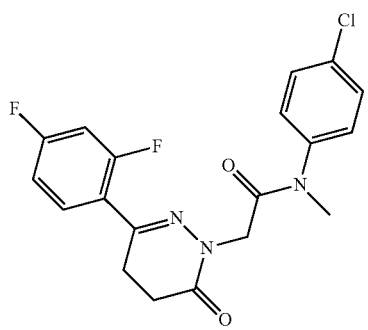 [SMILES: CN(C(=O)CN1N=C(c2ccc(F)cc2F)CCC1=O)c1ccc(Cl)cc1]

The title compound was prepared in analogy to Example 1-1 by using 2-[3-(2,4-diflurorphenyl)-6-oxo-4,5-dihydropyridazin-1-yl]acetic acid (100 mg) and 4-chloro-N-methylaniline (35 μL) instead of 2-[3-(4-chlorophenyl)-6-oxo-4,5-dihydropyridazin-1-yl]acetic acid and 4-chloro-N-methylaniline. N-(4-Chlorophenyl)-2-[3-(2,4-difluorophenyl)-6-oxo-4,5-dihydropyridazin-1-yl]-N-methyl-acetamide was obtained as a colorless solid (53 mg). $^1$H NMR (400 MHz, CDCl$_3$): δ 7.61-7.67 (m, 1H), 7.45 (d, J=8.5 Hz, 2H), 7.26 (d, J=8.2 Hz, 2H), 6.80-6.92 (m, 2H), 4.36 (s, 2H), 3.30 (s, 3H), 3.01 (t, J=8.2 Hz, 2H), 2.63 (t, J=8.2 Hz, 2H). MS obsd. (ESI$^+$) [(M+H)$^+$]: 393.

Example 1-34: 2-[3-(2,4-Difluorophenyl)-6-oxo-4,5-dihydropyridazin-1-yl]-N-(3-fluorophenyl)-N-methyl-acetamide

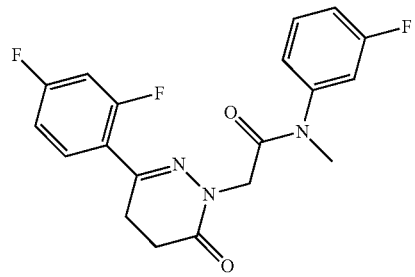 [SMILES: CN(C(=O)CN1N=C(c2ccc(F)cc2F)CCC1=O)c1cccc(F)c1]

The title compound was prepared in analogy to Example 1-1 by using 2-[3-(2, 4-difluorophenyl)-6-oxo-4,5-dihydropyridazin-1-yl]acetic acid (100 mg) and 3-fluoro-N-methylaniline (46 mg) instead of 2-[3-(4-chlorophenyl)-6-oxo-4,5-dihydropyridazin-1-yl]acetic acid and 4-chloro-N-methylaniline. 2-[3-(2,4-Difluorophenyl)-6-oxo-4,5-dihydropyridazin-1-yl]-N-(3-fluorophenyl)-N-methyl-acetamide was obtained as a colorless solid (81 mg). $^1$H NMR (400 MHz, CDCl$_3$): δ 7.66 (m, 1H), 7.43 (m, 1H), 7.10 (m, 3H), 6.80-6.92 (m, 2H), 4.39 (s, 2H), 3.27 (s, 3H), 2.97 (t, J=8.1 Hz, 2H), 2.60 (t, J=8.1 Hz, 2H). MS obsd. (ESI$^+$) [(M+H)$^+$]: 376.

Example 1-35: 2-[3-(4-Fluoro-3-methyl-phenyl)-6-oxo-4,5-dihydropyridazin-1-yl]-N-methyl-N-[3-(trifluoromethyl)phenyl]acetamide

Step 1: Preparation of ethyl 2-[3-(4-fluoro-3-methyl-phenyl)-6-oxo-4,5-dihydropyridazin-1-yl]acetate

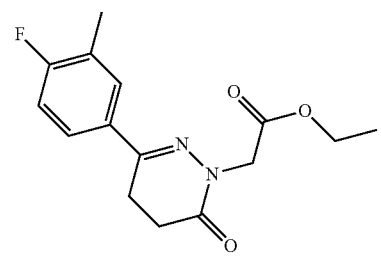 [SMILES: CCOC(=O)CN1N=C(c2ccc(F)c(C)c2)CCC1=O]

To a mixture of 4-(4-fluoro-3-methyl-phenyl)-4-oxo-butanoic acid (3.3 g, 15.7 mmol, Intermediate 12) and ethyl hydrazinoacetate hydrochloride (2.43 g, 15.7 mmol) in ethanol (20 mL) was added triethylamine (2.24 mL, 15.7 mmol). The mixture was heated with stirring under reflux for 6 hours. The resulting mixture was concentrated under vacuum and to the residue was added water (50 mL). The mixture was extracted with ethyl acetate (50 mL) three times. The combined organic phases were dried over anhydrous sodium sulfate and concentrated under vacuum. The residue was purified by column chromatography to afford ethyl 2-[3-(4-fluoro-3-methyl-phenyl)-6-oxo-4,5-dihydropyridazin-1-yl]acetate (1.5 g, 33%).

Step 2: Preparation of 2-[3-(4-fluoro-3-methyl-phenyl)-6-oxo-4,5-dihydropyridazin-1-yl]acetic acid

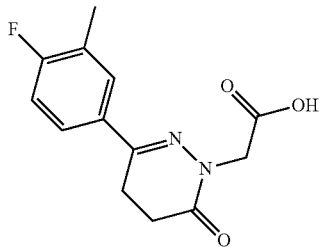 [SMILES: Cc1cc(C2=NN(CC(=O)O)C(=O)CC2)ccc1F]

A mixture of ethyl 2-[3-(4-fluoro-3-methyl-phenyl)-6-oxo-4,5-dihydropyridazin-1-yl]acetate (1.5 g, 5.1 mmol) and lithium hydroxide monohydrate (600 mg, 15 mmol) in tetrahydrofuran/water (50 mL, V/V=1/1) was heated with stirring at 60° C. for 1 hour. The mixture was concentrated under vacuum to remove the organic solvent, then the aqueous residue was acidified to pH=2 with hydrochloric acid (1 M) and extracted with ethyl acetate. The organic phase was dried over anhydrous sodium sulfate, filtered and concentrated under vacuum to afford 2-[3-(4-fluoro-3-methyl-phenyl)-6-oxo-4,5-dihydropyridazin-1-yl]acetic acid (1.15 g, 80%).

Step 3: Preparation of 2-[3-(4-fluoro-3-methyl-phenyl)-6-oxo-4,5-dihydropyridazin-1-yl]-N-methyl-N-[3-(trifluoromethyl)phenyl]acetamide

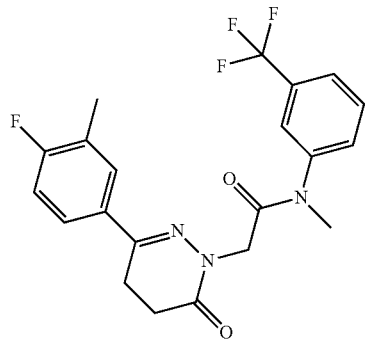 [SMILES: Cc1cc(C2=NN(CC(=O)N(C)c3cccc(C(F)(F)F)c3)C(=O)CC2)ccc1F]

The title compound was prepared in analogy to Example 1-1 by using 2-[3-(4-fluoro3-methylphenyl)-6-oxo-4,5-dihydropyridazin-1-yl]acetic acid (80 mg) and 3-trifluoromethyl-N-methylaniline (70 mg) instead of 2-[3-(4-chlorophenyl)-6-oxo-4,5-dihydropyridazin-1-yl]acetic acid and 4-chloro-N-methylaniline. 2-[3-(4-Fluoro-3-methyl-phenyl)-6-oxo-4,5-dihydropyridazin-1-yl]-N-methyl-N-[3-(trifluoromethyl)phenyl]acetamide was obtained as a colorless solid (30 mg). $^1$H NMR (400 MHz, CDCl$_3$): δ 7.57-7.65 (m, 5H), 7.48-7.52 (m, 1H), 7.03 (t, J=8.9 Hz, 1H), 4.39 (s, 2H), 3.36 (s, 3H), 2.98 (t, J=8.0 Hz, 2H), 2.63 (t, J=8.0 Hz, 2H), 2.31 (s, 3H). MS obsd. (ESI$^+$) [(M+H)$^+$]: 422.

Example 1-36: 2-[3-(4-Fluoro-3-methyl-phenyl)-6-oxo-4,5-dihydropyridazin-1-yl]-N-methyl-N-[4-(trifluoromethyl)phenyl]acetamide

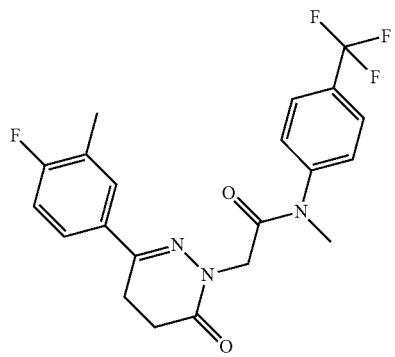 [SMILES: Cc1cc(C2=NN(CC(=O)N(C)c3ccc(C(F)(F)F)cc3)C(=O)CC2)ccc1F]

The title compound was prepared in analogy to Example 1-1 by using 2-[3-(4-fluoro-3-methyl-chlorophenyl)-6-oxo-4,5-dihydropyridazin-1-yl]acetic acid (80 mg) and 4-trifluoromethyl-N-methylaniline (70 mg) instead of 2-[3-(4-chlorophenyl)-6-oxo-4,5-dihydropyridazin-1-yl]acetic acid and 4-chloro-N-methylaniline. 2-[3-(4-Fluoro-3-methyl-phenyl)-6-oxo-4,5-dihydropyridazin-1-yl]-N-methyl-N-[4-(trifluoromethyl)phenyl]acetamide was obtained (35 mg). $^1$H NMR (400 MHz, CDCl$_3$): δ 7.75 (d, J=8.0 Hz, 2H), 7.48-7.59 (m, 4H), 7.03 (t, J=8.0 Hz, 1H), 4.42 (s, 2H), 3.36 (s, 3H), 2.98 (t, J=8.0 Hz, 2H), 2.63 (t, J=8.0 Hz, 2H), 2.32 (s, 3H). MS obsd. (ESI$^+$) [(M+H)$^+$]: 422.

Example 1-37: 2-[3-(4-Fluoro-3-methyl-phenyl)-6-oxo-4,5-dihydropyridazin-1-yl]-N-[4-fluoro-3-(trifluoromethyl)phenyl]-N-methyl-acetamide

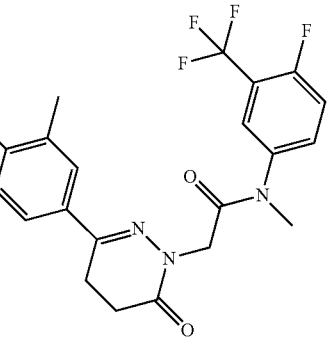

The title compound was prepared in analogy to Example 1-1 by using 2-[3-(4-fluoro-3-methylphenyl)-6-oxo-4,5-dihydropyridazin-1-yl]acetic acid (80 mg) and 4-fluoro-3-trifluoromethyl-N-methylaniline (100 mg) instead of 2-[3-(4-chlorophenyl)-6-oxo-4,5-dihydropyridazin-1-yl]acetic acid and 4-chloro-N-methylaniline. 2-[3-(4-Fluoro-3-methyl-phenyl)-6-oxo-4,5-dihydropyridazin-1-yl]-N-[4-fluoro-3-(trifluoromethyl)phenyl]-N-methyl-acetamide was obtained (32 mg). $^1$H NMR (400 MHz, CDCl$_3$): δ 7.58 (m, 3H), 7.48-7.57 (m, 1H), 7.33 (t, J=8.0 Hz, 1H), 7.03 (t, J=8.0 Hz, 1H), 4.35 (s, 2H), 3.32 (s, 3H), 2.99 (t, J=8.0 Hz, 2H), 2.64 (t, J=8.0 Hz, 2H), 2.30 (s, 3H). MS obsd. (ESI$^+$) [(M+H)$^+$]: 440.

Example 1-38: 2-[3-(4-Fluoro-3-methyl-phenyl)-6-oxo-4,5-dihydropyridazin-1-yl]-N-[3-fluoro-4-(trifluoromethyl)phenyl]-N-methyl-acetamide

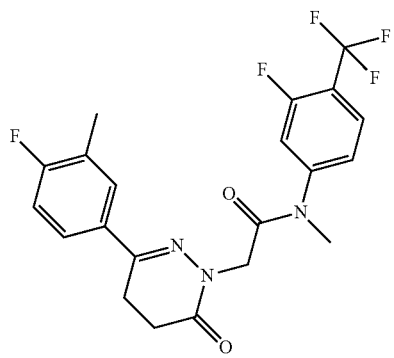 [SMILES: Cc1cc(C2=NN(CC(=O)N(C)c3ccc(C(F)(F)F)c(F)c3)C(=O)CC2)ccc1F]

The title compound was prepared in analogy to Example 1-1 by using 2-[3-(4-fluoro-3-methyl-phenyl)-6-oxo-4,5-dihydropyridazin-1-yl]acetic acid (80 mg) and 3-fluoro-4-(trifluoromethyl)phenyl-N-methylaniline (100 mg) instead of 2-[3-(4-chlorophenyl)-6-oxo-4,5-dihydropyridazin-1-yl] acetic acid and 4-chloro-N-methylaniline. 2-[3-(4-Fluoro-3-methyl-phenyl)-6-oxo-4,5-dihydropyridazin-1-yl]-N-[3-fluoro-4-(trifluoromethyl)phenyl]-N-methyl-acetamide was obtained as a colorless solid (80 mg). $^1$H NMR (400 MHz, CDCl$_3$): δ 7.71 (t, J=8.0 Hz, 1H), 7.58 (d, J=8.0 Hz, 1H), 7.48 (m, 1H), 7.3 (m, 2H), 7.04 (t, J=8.0 Hz, 1H), 4.50 (s, 2H), 3.38 (s, 3H), 3.00 (t, J=8.0 Hz, 2H), 2.67 (t, J=8.0 Hz, 2H), 2.32 (s, 3H). MS obsd. (ESI$^+$) [(M+H)$^+$]: 440.

Example 1-39: N-(3-Chlorophenyl)-N-methyl-2-[6-oxo-3-[4-(trifluoromethyl)phenyl]-4,5-dihydropyridazin-1-yl]acetamide Step 1: Preparation of ethyl 2-[6-oxo-3-[4-(trifluoromethyl)phenyl]-4,5-dihydropyridazin-1-yl]acetate

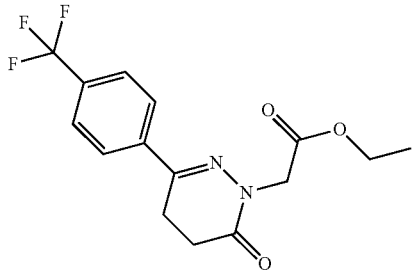 [SMILES: CCOC(=O)CN1N=C(c2ccc(C(F)(F)F)cc2)CCC1=O]

To a mixture of 4-oxo-4-[4-(trifluoromethyl)phenyl]butanoic acid (1.1 g, 4.5 mmol) and ethyl hydrazinoacetate hydrochloride (693 mg, 4.5 mmol) in ethanol (20 mL) was added triethylamine (0.64 mL, 4.5 mmol). The mixture was heated with stirring under reflux for 6 hours. The resulting mixture was concentrated under vacuum and to the residue was added water (50 mL). The mixture was extracted with ethyl acetate (50 mL) three times. The combined organic phases were dried over anhydrous sodium sulfate and filtered. The filtrate was then concentrated under vacuum and the residue was purified by column chromatography to afford ethyl 2-[6-oxo-3-[4-(trifluoromethyl)phenyl]-4,5-dihydropyridazin-1-yl]acetate (275 mg, 18.5%).

Step 2: Preparation of 2-[6-oxo-3-[4-(trifluoromethyl)phenyl]-4,5-dihydropyridazin-1-yl]acetic acid

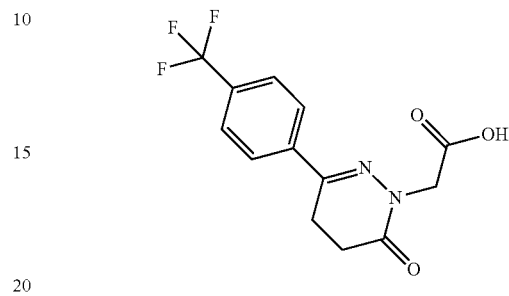

A mixture of ethyl 2-[6-oxo-3-[4-(trifluoromethyl)phenyl]-4,5-dihydropyridazin-1-yl]acetate (275 mg, 0.84 mmol) and lithium hydroxide monohydrate (105 mg, 2.5 mmol) in tetrahydrofuran/water (9 mL, V/V=2/1) was heated with stirring at 60° C. for 1 hour. The mixture was concentrated under vacuum to remove the organic solvent, then the aqueous residue was acidified to pH=2 with and hydrochloric acid (1 M) and extracted with ethyl acetate. The organic phase was dried over anhydrous sodium sulfate, filtered and concentrated under vacuum to afford 2-[6-oxo-3-[4-(trifluoromethyl)phenyl]-4,5-dihydropyridazin-1-yl] acetic acid (230 mg, 80%).

Step 3: Preparation of N-(3-chlorophenyl)-N-methyl-2-[6-oxo-3-[4-(trifluoromethyl)phenyl]-4,5-dihydropyridazin-1-yl]acetamide

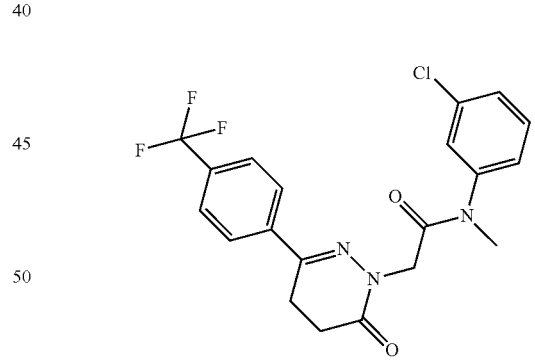

The title compound was prepared in analogy to Example 1-1 by using 2-[3-(4-(trifluoromethyl)phenyl)-6-oxo-4,5-dihydropyridazin-1-yl]acetic acid (50 mg) and 3-chloro-N-methylaniline (30 μL) instead of 2-[3-(4-chlorophenyl)-6-oxo-4,5-dihydropyridazin-1-yl]acetic acid and 4-chloro-N-methylaniline. N-(3-Chlorophenyl)-N-methyl-2-[6-oxo-3-[4-(trifluoromethyl)phenyl]-4,5-dihydropyridazin-1-yl] acetamide was obtained as a colorless solid (28 mg). $^1$H NMR (400 MHz, CDCl$_3$): δ 7.84 (d, J=8.0 Hz, 2H), 7.66 (d, J=8.0 Hz, 2H), 7.42 (m, 3H), 7.27 (m, 1H), 4.42 (s, 2H), 3.3 (s, 3H), 3.04 (t, J=8.0 Hz, 2H), 2.68 (t, J=8.0 Hz, 2H). MS obsd. (ESI$^+$) [(M+H)$^+$]: 424.

Example 1-40: N-Methyl-2-[6-oxo-3-[4-(trifluoromethyl)phenyl]-4,5-dihydropyridazin-1-yl]-N-[4-(trifluoromethyl)phenyl]acetamide

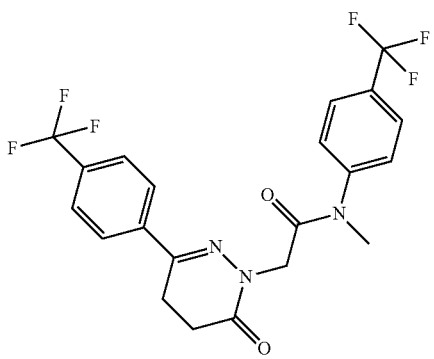 [SMILES: CN(C(=O)CN1N=C(c2ccc(C(F)(F)F)cc2)CCC1=O)c1ccc(C(F)(F)F)cc1]

The title compound was prepared in analogy to Example 1-1 by using 2-[3-(4-(trifluoromethyl)phenyl)-6-oxo-4,5-dihydropyridazin-1-yl]acetic acid (50 mg) and 4-trifluoromethyl-N-methylaniline (40 mg) in the presence of PyBrOP instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. N-Methyl-2-[6-oxo-3-[4-(trifluoromethyl)phenyl]-4,5-dihydropyridazin-1-yl]-N-[4-(trifluoromethyl)phenyl]acetamide was obtained (5 mg). $^1$H NMR (400 MHz, CDCl$_3$): δ 7.81 (d, J=8.0 Hz, 2H), 7.76 (d, J=8.0 Hz, 2H), 7.66 (d, J=8.0 Hz, 2H), 7.51 (d, J=8.0 Hz, 2H), 4.44 (s, 2H), 3.36 (s, 3H), 3.04 (t, J=8.0 Hz, 2H), 2.69 (t, J=8.0 Hz, 2H). MS obsd. (ESI$^+$) [(M+H)$^+$]: 458.

Example 1-41: N-Methyl-2-[6-oxo-3-[4-(trifluoromethyl)phenyl]-4,5-dihydropyridazin-1-yl]-N-[3-(trifluoromethyl)phenyl]acetamide

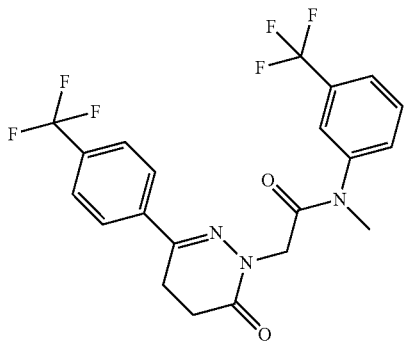 [SMILES: CN(C(=O)CN1N=C(c2ccc(C(F)(F)F)cc2)CCC1=O)c1cccc(C(F)(F)F)c1]

The title compound was prepared in analogy to Example 1-1 by using 2-[3-(4-(trifluoromethyl)phenyl)-6-oxo-4,5-dihydropyridazin-1-yl]acetic acid (50 mg) and 3-(trifluoromethyl-N-methylaniline in the presence of PyBrOP instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. N-Methyl-2-[6-oxo-3-[4-(trifluoromethyl)phenyl]-4,5-dihydropyridazin-1-yl]-N-[3-(trifluoromethyl)phenyl]acetamide was obtained (6 mg). $^1$H NMR (400 MHz, CDCl$_3$): δ 7.84 (d, J=8.0 Hz, 2H), 7.58-7.68 (m, 5H), 7.28 (s, 1H), 4.40 (s, 2H), 3.36 (s, 3H), 3.04 (t, J=8.0 Hz, 2H), 2.68 (t, J=8.0 Hz, 2H). MS obsd. (ESI$^+$) [(M+H)$^+$]: 458.

Example 1-42: N-(3-Fluorophenyl)-N-methyl-2-[6-oxo-3-[4-(trifluoromethyl)phenyl]-4,5-dihydropyridazin-1-yl]acetamide

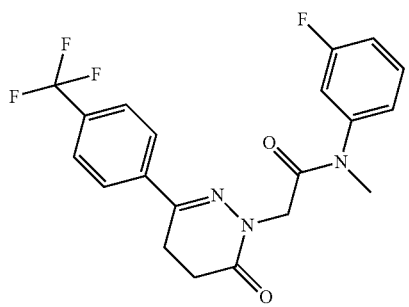 [SMILES: CN(C(=O)CN1N=C(c2ccc(C(F)(F)F)cc2)CCC1=O)c1cccc(F)c1]

The title compound was prepared in analogy to Example 1-1 by using 2-[3-(4-triflurormethylphenyl)-6-oxo-4,5-dihydropyridazin-1-yl]acetic acid (50 mg) and 3-fluoro-N-methylaniline (25 μL) in the presence of PyBrOP instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. N-(3-Fluorophenyl)-N-methyl-2-[6-oxo-3-[4-(trifluoromethyl)phenyl]-4,5-dihydropyridazin-1-yl]acetamide was obtained as a colorless solid (7 mg). $^1$H NMR (400 MHz, CDCl$_3$): δ 7.84 (d, J=8.0 Hz, 2H), 7.66 (d, J=8.0 Hz, 2H), 7.46 (m, 1H), 7.09-7.12 (m, 3H), 4.43 (s, 2H), 3.33 (s, 3H), 3.04 (t, J=8.0 Hz, 2H), 2.69 (t, J=8.0 Hz, 2H). MS obsd. (ESI$^+$) [(M+H)$^+$]: 408.

Example 1-43: N-(4-Fluorophenyl)-N-methyl-2-[6-oxo-3-[4-(trifluoromethyl)phenyl]-4,5-dihydropyridazin-1-yl]acetamide

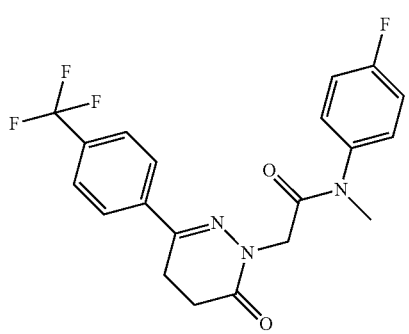 [SMILES: CN(C(=O)CN1N=C(c2ccc(C(F)(F)F)cc2)CCC1=O)c1ccc(F)cc1]

The title compound was prepared in analogy to Example 1-1 by using 2-[3-(4-(trifluoromethyl)phenyl)-6-oxo-4,5-dihydropyridazin-1-yl]acetic acid (60 mg) and 4-fluorophenyl-N-methylaniline (25 μL) in the presence of PyBrOP instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. N-(4-fluorophenyl)-N-methyl-2-[6-oxo-3-[4-(trifluoromethyl)phenyl]-4,5-dihydropyridazin-1-yl]acetamide was obtained (17 mg). $^1$H NMR (400 MHz, DMSO-d6): δ 7.94

(d, J=8.0 Hz, 2H), 7.81 (d, J=8.0 Hz, 2H), 7.51 (m, 2H), 7.33 (m, 2H), 4.25 (s, 2H), 3.17 (s, 3H), 3.02 (t, J=8.0 Hz, 2H), 2.51 (t, J=8.0 Hz, 2H). MS obsd. (ESI+) [(M+H)+]: 408.

Example 1-44: N-(4-Chlorophenyl)-N-methyl-2-[6-oxo-3-[4-(trifluoromethyl)phenyl]-4,5-dihydro-pyridazin-1-yl]acetamide

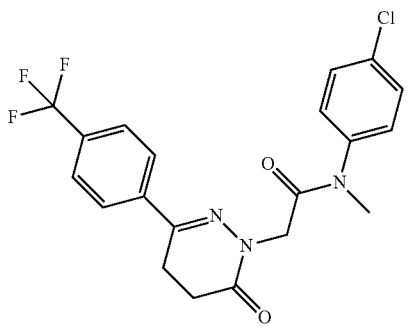 [SMILES: CN(C(=O)CN1N=C(c2ccc(C(F)(F)F)cc2)CCC1=O)c1ccc(Cl)cc1]

The title compound was prepared in analogy to Example 1-1 by using 2-[3-(4-(trifluoromethyl)phenyl)-6-oxo-4,5-dihydropyridazin-1-yl]acetic acid (70 mg) and 4-chloro-N-methylaniline (45 µL) in the presence of HATU instead of 2-[3-(4-chlorophenyl)-6-oxo-4,5-dihydropyridazin-1-yl] acetic acid and 4-chloro-N-methylaniline in the presence of 1-propylphosphonic acid cyclic anhydride. N-(4-Chlorophenyl)-N-methyl-2-[6-oxo-3-[4-(trifluoromethyl)phenyl]-4,5-dihydropyridazin-1-yl]acetamide was obtained (5 mg). 1H NMR (400 MHz, DMSO-d6): δ 7.94 (d, J=8.0 Hz, 2H), 7.81 (d, J=8.0 Hz, 2H), 7.53 (m, 2H), 7.48 (m, 2H), 4.30 (s, 2H), 3.19 (s, 3H), 3.02 (t, J=8.0 Hz, 2H), 2.51 (t, J=8.0 Hz, 2H). MS obsd. (ESI+) [(M+H)+]: 424.

Example 1-45: 2-[3-(3,4-Dichlorophenyl)-6-oxo-4,5-dihydropyridazin-1-yl]-N-methyl-N-[4-(trifluoromethyl)phenyl]acetamide Step 1: Preparation of ethyl 2-[3-(3,4-dichlorophenyl)-6-oxo-4,5-dihydropyridazin-1-yl]acetate

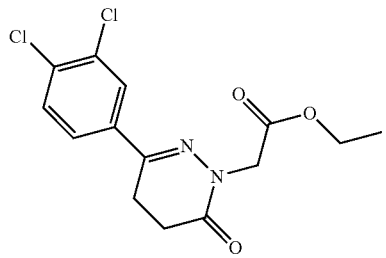 [SMILES: CCOC(=O)CN1N=C(c2ccc(Cl)c(Cl)c2)CCC1=O]

To a mixture of 4-(3,4-dichlorophenyl)-4-oxo-butanoic acid (4.94 g, 20.0 mmol) and ethyl hydrazinoacetate hydrochloride (3.1 g, 20.0 mmol) in ethanol (20 mL) was added triethylamine (2.8 mL, 20 mmol). The mixture was heated with stirring under reflux for 6 hours. The solvent was removed under vacuum and to the residue was added water. The mixture was extracted with ethyl acetate (50 mL) three times. The combined organic phases were dried over anhydrous sodium sulfate and concentrated under vacuum. The residue was purified by column chromatography to afford ethyl 2-[3-(3,4-dichlorophenyl)-6-oxo-4,5-dihydropyridazin-1-yl]acetate (2.69 g, 41%).

Step 2: Preparation of 2-[3-(3,4-dichlorophenyl)-6-oxo-4,5-dihydropyridazin-1-yl]acetic acid

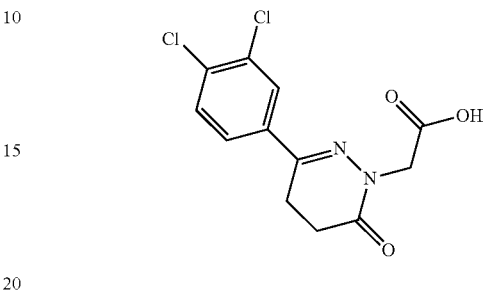

A mixture of ethyl 2-[3-(3,4-dichlorophenyl)-6-oxo-4,5-dihydropyridazin-1-yl]acetate (2.69 g, 8.2 mmol) and lithium hydroxide monohydrate (1.7 g, 41.0 mmol) in methanol/water (20 mL, V/V=1/1) was stirred at room temperature for 2 hours. The mixture was concentrated under vacuum to remove the organic solvent, then the aqueous residue was acidified to pH=2 with hydrochloric acid (1 M). The resulting mixture was extracted with ethyl acetate and then the organic phase was dried over anhydrous sodium sulfate, filtered and concentrated under vacuum to afford 2-[3-(3,4-dichlorophenyl)-6-oxo-4,5-dihydropyridazin-1-yl]acetic acid (2.2 g, 88%).

Step 3: Preparation of 2-[3-(3,4-dichlorophenyl)-6-oxo-4,5-dihydropyridazin-1-yl]-N-methyl-N-[4-(trifluoromethyl)phenyl]acetamide

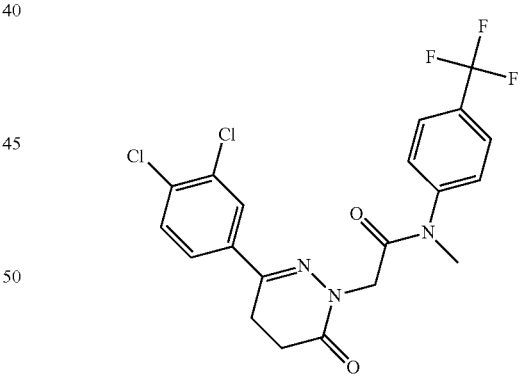

The title compound was prepared in analogy to Example 1-1 by using 2-[3-(3,4-chlorophenyl)-6-oxo-4,5-dihydropyridazin-1-yl]acetic acid (50 mg) and 4-trifluoromethyl-N-methylaniline (29 mg) instead of 2-[3-(4-chlorophenyl)-6-oxo-4,5-dihydropyridazin-1-yl]acetic acid and 4-chloro-N-methylaniline. 2-[3-(3,4-dichlorophenyl)-6-oxo-4,5-dihydropyridazin-1-yl]-N-methyl-N-[4-(trifluoromethyl)phenyl]acetamide was obtained (69 mg). 1H NMR (400 MHz, CDCl3): δ 7.81 (d, J=2.1 Hz, 1H), 7.73 (d, J=8.1 Hz, 2H), 7.48-7.51 (m, 3H), 7.44 (d, J=8.0 Hz, 1H), 4.39 (s, 2H), 3.33 (s, 3H), 2.94 (t, J=8.0 Hz, 2H), 2.63 (t, J=8.0 Hz, 2H). MS obsd. (ESI+) [(M+H)+]: 458.

Example 1-46: N-(4-Chlorophenyl)-2-[3-(3,4-di-chlorophenyl)-6-oxo-4,5-dihydropyridazin-1-yl]-N-methyl-acetamide

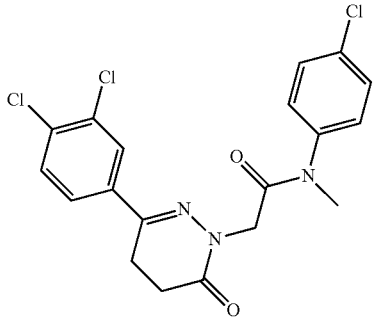 [SMILES: CN(C(=O)CN1N=C(c2ccc(Cl)c(Cl)c2)CCC1=O)c1ccc(Cl)cc1]

The title compound was prepared in analogy to Example 1-1 by using 2-[3-(3,4-dichlorophenyl)-6-oxo-4,5-dihydropyridazin-1-yl]acetic acid (100 mg) and 4-chloro-N-methylaniline (47 mg) instead of 2-[3-(4-chlorophenyl)-6-oxo-4,5-dihydropyridazin-1-yl]acetic acid and 4-chloro-N-methylaniline. N-(4-Chlorophenyl)-2-[3-(3,4-dichlorophenyl)-6-oxo-4,5-dihydropyridazin-1-yl]-N-methyl-acetamide was obtained as a colorless solid (91 mg). $^1$H NMR (400 MHz, CDCl$_3$): δ 7.81 (d, J=2.0 Hz, 1H), 7.50 (dd, J=2.0, 8.0 Hz, 1H), 7.43-7.46 (m, 3H), 7.29 (d, J=8.0 Hz, 2H), 4.34 (s, 2H), 3.28 (s, 3H), 2.95 (t, J=8.0 Hz, 2H), 2.64 (t, J=8.0 Hz, 2H). MS obsd. (ESI$^+$) [(M+H)$^+$]: 424.

Example 1-47: 2-[3-(4-Fluorophenyl)-6-oxo-4,5-dihydropyridazin-1-yl]-N-methyl-N-phenyl-acetamide

Step 1: Preparation of ethyl 2-[3-(4-fluorophenyl)-6-oxo-4,5-dihydropyridazin-1-yl]acetate

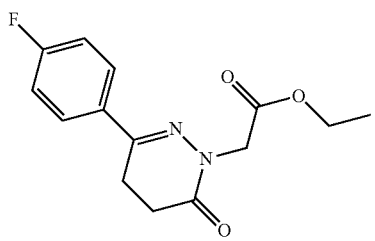 [SMILES: CCOC(=O)CN1N=C(c2ccc(F)cc2)CCC1=O]

To a mixture of 4-(4-fluoro-phenyl)-4-oxo-butanoic acid (1.96 g, 10 mmol, CAS RN 366-77-8) and ethyl hydrazino-acetate hydrochloride (1.55 g, 10 mmol) in ethanol (25 mL) was added triethylamine (1.01 g, 10 mmol). The mixture was heated with stirring under reflux for 3.5 hours. The resulting mixture was cooled to room temperature, the solid was collected by vacuum filtration to give ethyl 2-[3-(4-chloro-2-methyl-phenyl)-6-oxo-4,5-dihydropyridazin-1-yl] acetate (2.0 g, 72%).

Step 2: Preparation of 2-[3-(4 fluoro-phenyl)-6-oxo-4,5-dihydropyridazin-1-yl]acetic acid

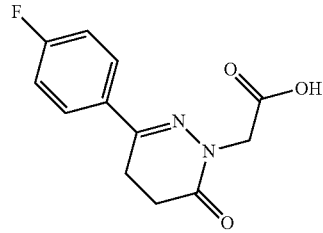 [SMILES: O=C(O)CN1N=C(c2ccc(F)cc2)CCC1=O]

A mixture of ethyl 2-[3-(4-dichlorophenyl)-6-oxo-4, 5-dihydropyridazin-1-yl]acetate (2.0 g, 7.2 mmol) and lithium hydroxide monohydrate (840 mg, 20 mmol) in tetrahydrofuran/water (50 mL, V/V=1/1) was heated with stirring at 60° C. for 1 hour. The resulting mixture was concentrated under vacuum to remove the organic solvent, then the aqueous residue was acidified to pH=2 with hydrochloric acid (1 M) and extracted with ethyl acetate. The organic phase was dried over anhydrous sodium sulfate, filtered and concentrated under vacuum to afford 2-[3-(4-fluorophenyl)-6-oxo-4,5-dihydropyridazin-1-yl]acetic acid (1.25 g, 70%).

Step 3: Preparation of 2-[3-(4-fluorophenyl)-6-oxo-4,5-dihydropyridazin-1-yl]-N-methyl-N-phenyl-acetamide

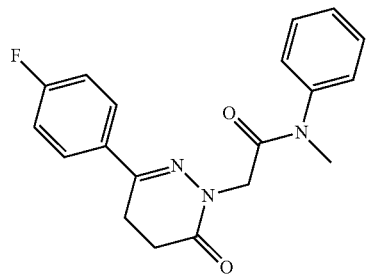 [SMILES: CN(C(=O)CN1N=C(c2ccc(F)cc2)CCC1=O)c1ccccc1]

The title compound was prepared in analogy to Example 1-1 by using 2-[3-(4-fluorophenyl)-6-oxo-4, 5-dihydropyridazin-1-yl]acetic acid (100 mg) and N-methylaniline (107 mg) instead of 2-[3-(4-chlorophenyl)-6-oxo-4,5-dihydropyridazin-1-yl]acetic acid and 4-chloro-N-methylaniline. 2-[3-(4-Fluorophenyl)-6-oxo-4,5-dihydropyridazin-1-yl]-N-methyl-N-phenyl-acetamide was obtained as a colorless solid (35 mg). $^1$H NMR (400 MHz, DMSO-d6): δ 7.77-7.81 (m, 2H), 7.37-7.54 (m, 4H), 7.25-7.31 (m, 3H), 4.24 (s, 2H), 3.20 (s, 3H), 2.96 (t, J=8.4 Hz, 2H), 2.52 (t, J=8.4 Hz, 2H). MS obsd. (ESI$^+$) [(M+H)$^+$]: 340.

Example 1-48: N-(4-Chlorophenyl)-2-[3-(4-fluorophenyl)-6-oxo-4,5-dihydropyridazin-1-yl]-N-methyl-acetamide

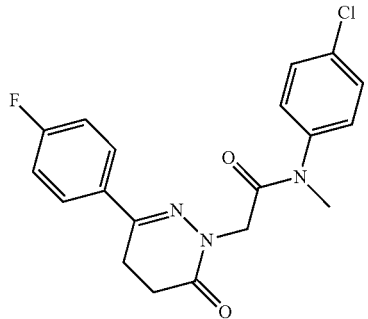 [SMILES: CN(C(=O)CN1N=C(c2ccc(F)cc2)CCC1=O)c1ccc(Cl)cc1]

The title compound was prepared in analogy to Example 1-1 by using 2-[3-(4-flurorphenyl)-6-oxo-4,5-dihydropyridazin-1-yl]acetic acid (100 mg) and 4-chloro-N-methylaniline (140 mg) instead of 2-[3-(4-chlorophenyl)-6-oxo-4,5-dihydropyridazin-1-yl]acetic acid and 4-chloro-N-methylaniline. N-(4-Chlorophenyl)-2-[3-(4-fluorophenyl)-6-oxo-4,5-dihydropyridazin-1-yl]-N-methyl-acetamide was obtained as a colorless solid (25 mg). $^1$H NMR (400 MHz, DMSO-d6): δ 7.76-7.83 (m, 2H), 7.41-7.58 (m, 4H), 7.25-7.31 (m, 2H), 4.28 (s, 2H), 3.19 (s, 3H), 2.96 (t, J=8.4 Hz, 2H), 2.53 (t, J=8.4 Hz, 2H). MS obsd. (ESI$^+$) [(M+H)$^+$]: 374.

Example 1-49: 2-[3-(4-Bromophenyl)-6-oxo-4,5-dihydropyridazin-1-yl]-N-methyl-N-phenyl-acetamide

Step 1: Preparation of ethyl 2-[3-(4-bromophenyl)-6-oxo-4,5-dihydropyridazin-1-yl]acetate

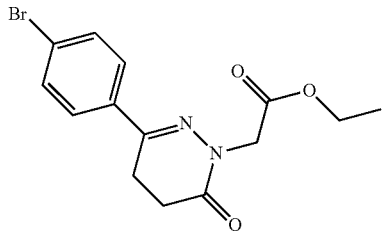 [SMILES: CCOC(=O)CN1N=C(c2ccc(Br)cc2)CCC1=O]

To a mixture of 4-(4-bromophenyl)-4-oxo-butanoic acid (2.58 g, 10 mmol, CAS RN 6340-79-0) and ethyl hydrazinoacetate hydrochloride (1.55 g, 10 mmol) in ethanol (25 mL) was added triethylamine (1.01 g, 10 mmol). The mixture was heated with stirring under reflux for 3.5 hours. The resulting mixture was cooled to room temperature. The solid was collected by vacuum filtration to give ethyl 2-[3-(4-bromophenyl)-6-oxo-4,5-dihydropyridazin-1-yl]acetate (2.55 g, 74%).

Step 2: Preparation of 2-[3-(4-bromophenyl)-6-oxo-4,5-dihydropyridazin-1-yl]acetic acid

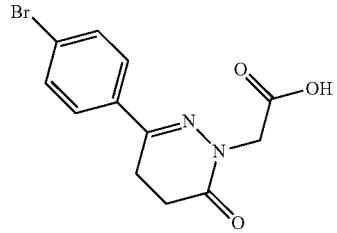

A mixture of ethyl 2-[3-(4-bromophenyl)-6-oxo-4,5-dihydropyridazin-1-yl]acetate (1.3 g, 3.8 mmol) and lithium hydroxide monohydrate (860 mg, 20 mmol) in tetrahydrofuran/water (50 mL, V/V=1/1) was heated with stirring at 60° C. for 1 hour. The mixture was concentrated under vacuum to remove the organic solvent, then the aqueous residue was acidified to pH=2 with hydrochloric acid (1 M) and extracted with ethyl acetate. The organic phase was dried over anhydrous sodium sulfate, filtered and concentrated to afford 2-[3-(4-bromophenyl)-6-oxo-4,5-dihydropyridazin-1-yl]acetic acid (1.0 g, 83%).

Step 3: Preparation of 2-[3-(4-bromophenyl)-6-oxo-4,5-dihydropyridazin-1-yl]-N-methyl-N-phenyl-acetamide

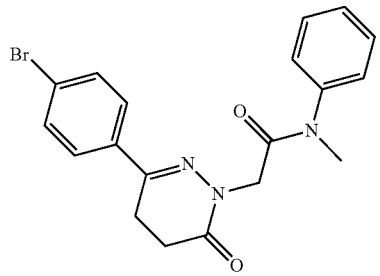 [SMILES: CN(C(=O)CN1N=C(c2ccc(Br)cc2)CCC1=O)c1ccccc1]

The title compound was prepared in analogy to Example 1-1 by using 2-[3-(4-bromophenyl)-6-oxo-4,5-dihydropyridazin-1-yl]acetic acid (120 mg) and N-methylaniline (107 mg) in the presence of HATU instead of 2-[3-(4-chlorophenyl)-6-oxo-4,5-dihydropyridazin-1-yl]acetic acid and 4-chloro-N-methylaniline in the presence of 1-propylphosphonic acid cyclic anhydride. 2-[3-(4-Bromophenyl)-6-oxo-4,5-dihydropyridazin-1-yl]-N-methyl-N-phenyl-acetamide was obtained (25 mg). $^1$H NMR (400 MHz, DMSO-d6): δ 7.62-7.72 (m, 4H), 7.34-7.55 (m, 5H), 4.24 (s, 2H), 3.20 (s, 3H), 2.96 (t, J=8.4 Hz, 2H), 2.55 (t, J=8.4 Hz, 2H). MS obsd. (ESI$^+$) [(M+H)$^+$]: 400.

Example 1-50: 2-[3-(4-Bromophenyl)-6-oxo-4,5-dihydropyridazin-1-yl]-N-(4-chlorophenyl)-N-methyl-acetamide

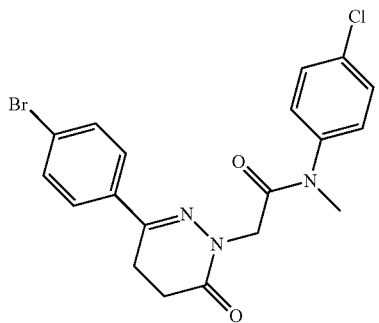

The title compound was prepared in analogy to Example 1-1 by using 2-[3-(4-bromophenyl)-6-oxo-4,5-dihydropyridazin-1-yl]acetic acid (120 mg) and 4-chloro-N-methylaniline (140 mg) in the presence of HATU instead of 2-[3-(4-chlorophenyl)-6-oxo-4,5-dihydropyridazin-1-yl] acetic acid and 4-chloro-N-methylaniline in the presence of 1-propylphosphonic acid cyclic anhydride. 2-[3-(4-Bromophenyl)-6-oxo-4,5-dihydropyridazin-1-yl]-N-(4-chlorophenyl)-N-methylacetamide was obtained as a colorless solid (55 mg). $^1$H NMR (400 MHz, DMSO-d6): δ 7.62-7.82 (m, 4H), 7.40-7.54 (m, 4H), 4.28 (s, 2H), 3.19 (s, 3H), 2.96 (t, J=8.4 Hz, 2H), 2.55 (t, J=8.4 Hz, 2H). MS obsd. (ESI$^+$) [(M+H)$^+$]: 434.

Example 1-51: 2-[3-(4-Bromophenyl)-6-oxo-4,5-dihydropyridazin-1-yl]-N-methyl-N-[4-(trifluoromethyl)phenyl]acetamide

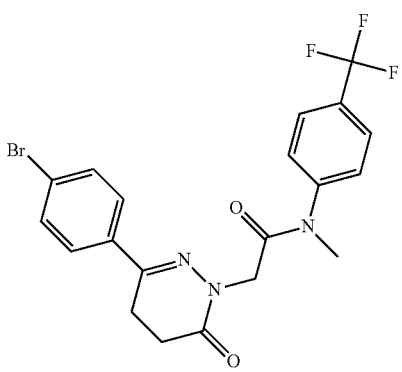

The title compound was prepared in analogy to Example 1-1 by using 2-[3-(4-bromophenyl)-6-oxo-4,5-dihydropyridazin-1-yl]acetic acid (50 mg) and 3-trifluoromethyl-N-methylaniline (28 mg) instead of 2-[3-(4-chlorophenyl)-6-oxo-4,5-dihydropyridazin-1-yl]acetic acid and 4-chloro-N-methylaniline. 2-[3-(4-Bromophenyl)-6-oxo-4,5-dihydropyridazin-1-yl]-N-methyl-N-[4-(trifluoromethyl)phenyl]acetamide was obtained as a colorless solid (69 mg). $^1$H NMR (400 MHz, CDCl$_3$): δ 7.75 (d, J=8 Hz, 2H), 7.59 (d, J=8.0 Hz, 2H), 7.49-7.54 (m, 4H), 4.39 (s, 2H), 3.33 (s, 3H), 2.98 (t, J=8.0 Hz, 2H), 2.64 (t, J=8.0 Hz, 2H). MS obsd. (ESI$^+$) [(M+H)$^+$]: 468.

Example 1-52: 2-[3-(3,4-Difluorophenyl)-6-oxo-4,5-dihydropyridazin-1-yl]-N-methyl-N-[3-(trifluoromethyl)phenyl]acetamide Step 1: Preparation of ethyl 2-[3-(3,4-difluoro-phenyl)-6-oxo-4,5-dihydropyridazin-1-yl]acetate

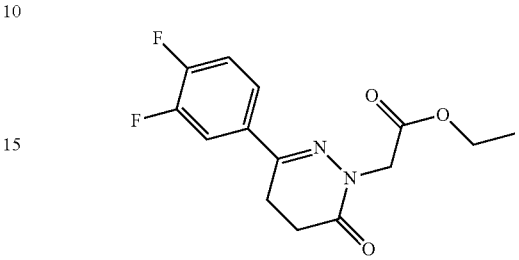

To a mixture of 4-(3,4-difluorophenyl)-4-oxo-butanoic acid (3.0 g, 14.0 mmol) and ethyl hydrazinoacetate hydrochloride (2.16 g, 14.0 mmol) in ethanol (20 mL) was added triethylamine (2.0 mL, 14.0 mmol). The mixture was heated with stirring under reflux for 6 hours. The resulting mixture was concentrated under vacuum and to the residue was added water (50 mL). The mixture was extracted with ethyl acetate (50 mL) three times and the combined organic phases were dried over anhydrous sodium sulfate and filtered. Then the filtrate was concentrated under vacuum and the residue was purified by column chromatography to afford ethyl 2-[3-(3,4-difluorophenyl)-6-oxo-4,5-dihydropyridazin-1-yl]acetate (450 mg, 11%).

Step 2: Preparation of 2-[3-(3,4-difluorophenyl)-6-oxo-4,5-dihydropyridazin-1-yl]acetic acid

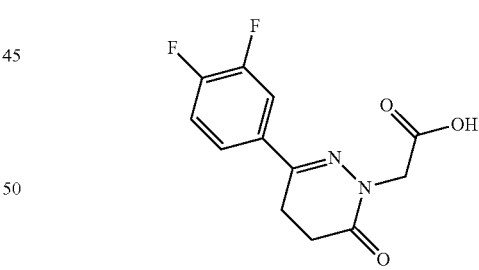

A mixture of ethyl 2-[3-(3,4-difluorophenyl)-6-oxo-4,5-dihydropyridazin-1-yl]acetate (450 mg, 1.52 mmol) and lithium hydroxide monohydrate (252 mg, 6.0 mmol) in tetrahydrofuran/water (9 mL, V/V=2/1) was heated with stirring at 60° C. for 1 hour. The mixture was concentrated under vacuum to remove the organic solvent, then the aqueous residue was acidified to pH=2 with hydrochloric acid (1 M), and extracted with ethyl acetate. The organic phase was dried over anhydrous sodium sulfate, filtered and concentrated under vacuum to afford 2-[3-(3,4-difluorophenyl)-6-oxo-4,5-dihydropyridazin-1-yl]acetic acid (300 mg, 74%).

Step 3: Preparation of 2-[3-(3,4-difluorophenyl)-6-oxo-4,5-dihydropyridazin-1-yl]-N-methyl-N-[3-(trifluoromethyl)phenyl]acetamide

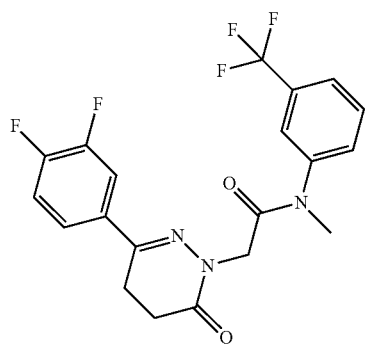

The title compound was prepared in analogy to Example 1-1 by using 2-[3-(3,4-difluorophenyl)-6-oxo-4,5-dihydropyridazin-1-yl]acetic acid (50 mg) and 3-trifluoromethyl-N-methylaniline (55 mg) instead of 2-[3-(4-chlorophenyl)-6-oxo-4,5-dihydropyridazin-1-yl]acetic acid and 4-chloro-N-methylaniline. 2-[3-(3,4-Difluorophenyl)-6-oxo-4,5-dihydropyridazin-1-yl]-N-methyl-N-[3-(trifluoromethyl)phenyl]acetamide was obtained as a colorless solid (16 mg). $^1$H NMR (400 MHz, CDCl$_3$): δ 7.58-7.61 (m, 5H), 7.42 (m, 1H), 7.18 (t, J=8.0 Hz, 1H), 4.38 (s, 2H), 3.36 (s, 3H), 2.97 (t, J=8.0 Hz, 2H), 2.66 (t, J=8.0 Hz, 2H). MS obsd. (ESI$^+$) [(M+H)$^+$]: 426.

Example 1-53: 2-[3-(3,4-Difluorophenyl)-6-oxo-4,5-dihydropyridazin-1-yl]-N-methyl-N-[4-(trifluoromethyl)phenyl]acetamide

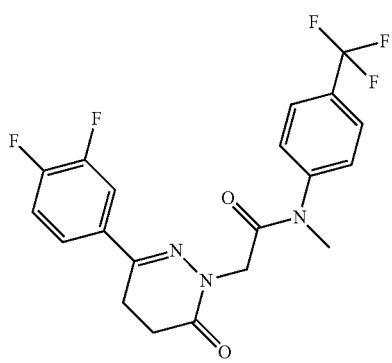

The title compound was prepared in analogy to Example 1-1 by using 2-[3-(3,4-difluorophenyl)-6-oxo-4,5-dihydropyridazin-1-yl]acetic acid (50 mg) and 4-trifluoromethyl-N-methylaniline (55 mg) instead of 2-[3-(4-chlorophenyl)-6-oxo-4,5-dihydropyridazin-1-yl]acetic acid and 4-chloro-N-methylaniline. 2-[3-(3,4-Difluorophenyl)-6-oxo-4,5-dihydropyridazin-1-yl]-N-methyl-N-[4-(trifluoromethyl)phenyl]acetamide was obtained as a colorless solid (16 mg). $^1$H NMR (400 MHz, CDCl$_3$): δ 7.75 (d, J=8.0 Hz, 2H), 7.57-7.65 (m, 1H), 7.5 (d, J=8.0 Hz, 2H), 7.42 (m, 1H), 7.19 (t, J=8.0 Hz, 1H), 4.41 (s, 2H), 3.36 (s, 3H), 2.66 (t, J=8.0 Hz, 2H). MS obsd. (ESI$^+$) [(M+H)$^+$]: 426.

Example 1-54: N-(4-Chlorophenyl)-2-[3-(2,4-dichlorophenyl)-6-oxo-4,5-dihydropyridazin-1-yl]-N-methyl-acetamide

Step 1: Preparation of ethyl 2-[3-(2,4-dichlorophenyl)-6-oxo-4,5-dihydropyridazin-1-yl]acetate

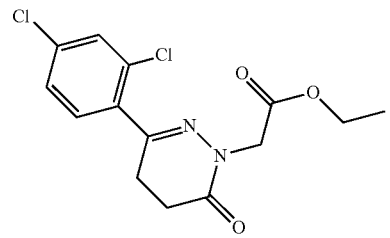

To a mixture of 4-(2,4-dichlorophenyl)-4-oxo-butanoic acid (1.0 g, 4.05 mmol) and ethyl hydrazinoacetate hydrochloride (0.63 g, 4.05 mmol) in ethanol (20 mL) was added triethylamine (0.57 mL, 4.05 mmol). The mixture was heated with stirring under reflux for 6 hours. The resulting mixture was concentrated under vacuum and to the residue was added water (20 mL). The mixture was extracted with ethyl acetate (20 mL) three times. The combined organic phases were dried over anhydrous sodium sulfate and concentrated under vacuum, the residue was purified by column chromatography to afford ethyl 2-[3-(2,4-dichlorophenyl)-6-oxo-4,5-dihydropyridazin-1-yl]acetate (800 mg, 61%).

Step 2: Preparation of 2-[3-(2,4-dichlorophenyl)-6-oxo-4,5-dihydropyridazin-1-yl]acetic acid

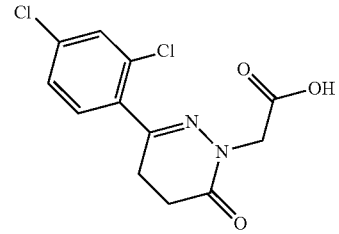

A mixture of ethyl 2-[3-(2,4-dichlorophenyl)-6-oxo-4,5-dihydropyridazin-1-yl]acetate (600 mg, 1.8 mmol) and lithium hydroxide monohydrate (382 mg, 9 mmol) in tetrahydrofuran/water (50 mL, V/V=1/1) was heated with stirring at 60° C. for 1 hour. The mixture was concentrated under vacuum to remove the organic solvent, then the aqueous residue was acidified to pH=2 with hydrochloric acid (1 M). The resulting mixture was extracted with ethyl acetate and the organic phase was dried over anhydrous sodium sulfate, filtered and concentrated under vacuum to afford 2-[3-(2,4-dichlorophenyl)-6-oxo-4,5-dihydropyridazin-1-yl]acetic acid (500 mg, 92%).

Step 3: Preparation of N-(4-chlorophenyl)-2-[3-(2,4-dichlorophenyl)-6-oxo-4,5-dihydropyridazin-1-yl]-N-methylacetamide

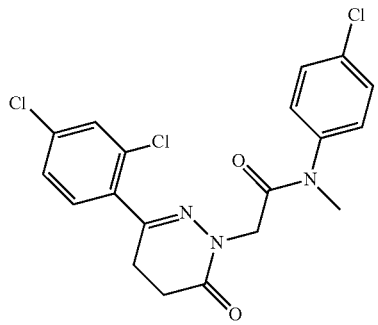

The title compound was prepared in analogy to Example 1-1 by using 2-[3-(2,4-dichlorophenyl)-6-oxo-4,5-dihydropyridazin-1-yl]acetic acid (104 mg) and 4-chloro-N-methylaniline (49 mg) instead of 2-[3-(4-chlorophenyl)-6-oxo-4,5-dihydropyridazin-1-yl]acetic acid and 4-chloro-N-methylaniline. N-(4-Chlorophenyl)-2-[3-(2,4-dichlorophenyl)-6-oxo-4,5-dihydropyridazin-1-yl]-N-methyl-acetamide was obtained as a colorless solid (36 mg). $^1$H NMR (400 MHz, CDCl$_3$): δ 7.38-7.42 (m, 4H), 7.24-7.28 (m, 3H), 4.31 (s, 2H), 3.27 (s, 3H), 2.95 (t, J=8.0 Hz, 2H), 2.63 (t, J=8.0 Hz, 2H). MS obsd. (ESI$^+$) [(M+H)$^+$]: 424.

Example 1-55: N-(4-Chlorophenyl)-2-[3-(4-cyanophenyl)-6-oxo-4,5-dihydropyridazin-1-yl]-N-methyl-acetamide

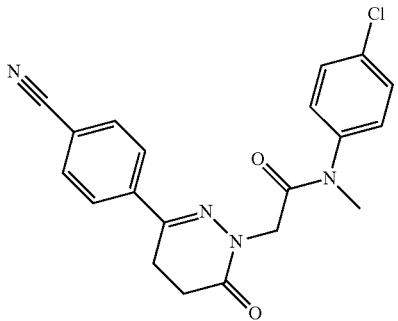 [SMILES: CN(C(=O)CN1N=C(c2ccc(C#N)cc2)CCC1=O)c1ccc(Cl)cc1]

To a mixture of 2-[3-(4-bromophenyl)-6-oxo-4,5-dihydropyridazin-1-yl]-N-(4-chlorophenyl)-N-methylacetamide (75 mg, Example 1-50) and Zn(CN)$_2$ (25 mg) in dimethylformamide was added Pd(PPh$_3$)$_4$ (20 mg). The resulting mixture was heated at 90° C. overnight. After the reaction was complete, the mixture was poured into water and extracted with ethyl acetate. The organic solvent was dried over sodium sulfate and concentrated under vacuum. N-(4-chlorophenyl)-2-[3-(4-cyanophenyl)-6-oxo-4,5-dihydropyridazin-1-yl]-N-methyl-acetamide was obtained (14 mg). $^1$H NMR (400 MHz, DMSO-d6): δ 7.91 (s, 4H), 7.48-7.53 (m, 4H), 4.3 (s, 2H), 3.19 (s, 3H), 3.01 (t, J=8.0 Hz, 2H), 2.55 (t, J=8.0 Hz, 2H). MS obsd. (ESI$^+$) [(M+H)$^+$]: 381.

Example 1-56: N-(4-Chlorophenyl)-N-methyl-2-[6-oxo-3-(p-tolyl)-4,5-dihydropyridazin-1-yl]acetamide

Step 1: Preparation of ethyl 2-[3-(4-methyl-phenyl)-6-oxo-4,5-dihydropyridazin-1-yl]acetate

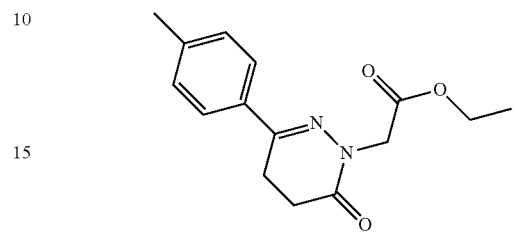

To a mixture of 4-oxo-4-(p-tolyl)butanoic acid (3.84 g, 20.0 mmol, CAS RN: 4619-20-9) and ethyl hydrazinoacetate hydrochloride (3.1 g, 20.0 mmol) in ethanol (20 mL) was added triethylamine (2.8 mL, 20.0 mmol). The mixture was heated with stirring under reflux for 6 hours. The resulting mixture was cooled to room temperature. The precipitate was filtered to give ethyl 2-[3-(4-methylphenyl)-6-oxo-4,5-dihydropyridazin-1-yl]acetate (1.5 g, 28%).

Step 2: Preparation of 2-[6-oxo-3-(p-tolyl)-4,5-dihydropyridazin-1-yl]acetic acid

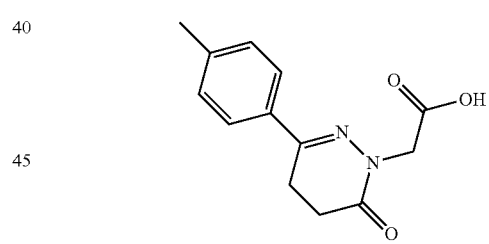

A mixture of ethyl 2-[3-(4-methylphenyl)-6-oxo-4,5-dihydropyridazin-1-yl]acetate (1.37 g, 5 mmol) and lithium hydroxide monohydrate (860 mg, 20 mmol) in tetrahydrofuran/water (50 mL, V/V=1/1) was heated with stirring at 60° C. for 1 hour. The mixture was concentrated under vacuum to remove the organic solvent, then the aqueous residue was acidified to pH=2 with hydrochloric acid (1 M) and extracted with ethyl acetate. The organic phase was dried over anhydrous sodium sulfate, filtered and concentrated under vacuum to afford 2-[6-oxo-3-(p-tolyl)-4,5-dihydropyridazin-1-yl]acetic acid (1.0 g, 93%).

Step 3: Preparation of N-(4-chlorophenyl)-N-methyl-2-[6-oxo-3-(p-tolyl)-4,5-dihydropyridazin-1-yl]acetamide

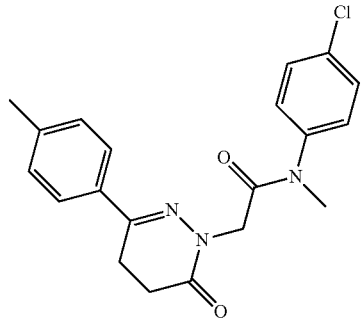 [SMILES: Cc1ccc(C2=NN(CC(=O)N(C)c3ccc(Cl)cc3)C(=O)CC2)cc1]

The title compound was prepared in analogy to Example 1-1 by using 2-[6-oxo-3-(p-tolyl)-4,5-dihydropyridazin-1-yl]acetic acid (100 mg) and 4-chloro-N-methylaniline (22 mg) instead of 2-[3-(4-chlorophenyl)-6-oxo-4,5-dihydropyridazin-1-yl]acetic acid and 4-chloro-N-methylaniline. N-(4-Chlorophenyl)-N-methyl-2-[6-oxo-3-(p-tolyl)-4,5-dihydropyridazin-1-yl]acetamide was obtained as a colorless solid (92 mg). $^1$H NMR (400 MHz, CDCl$_3$): δ 7.58 (d, J=8.0 Hz, 2H), 7.42 (d, J=8.0 Hz, 2H), 7.28 (d, J=8.0 Hz, 2H), 7.18 (d, J=8.0 Hz, 2H), 4.35 (s, 2H), 3.28 (s, 3H), 2.96 (t, J=8.0 Hz, 2H), 2.60 (t, J=8.0 Hz, 2H), 2.37 (s, 3H). MS obsd. (ESI$^+$) [(M+H)$^+$]: 370.

Example 1-57: N-(4-Chlorophenyl)-2-[3-(3-chlorophenyl)-6-oxo-4,5-dihydropyridazin-1-yl]-N-methyl-acetamide

Step 1: Preparation of ethyl 2-[3-(3-chlorophenyl)-6-oxo-4,5-dihydropyridazin-1-yl]acetate

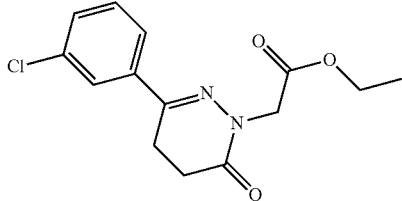 [SMILES: CCOC(=O)CN1N=C(c2cccc(Cl)c2)CCC1=O]

To a mixture of 4-(3-chlorophenyl)-4-oxo-butanoic acid (3.0 g, 14.0 mmol) and ethyl hydrazinoacetate hydrochloride (2.17 g, 14.0 mmol) in ethanol (25 mL) was added triethylamine (2.0 mL, 14.0 mmol). The mixture was heated with stirring under reflux for 6 hours. The resulting mixture was cooled to room temperature and the precipitate was filtered to afford ethyl 2-[3-(4-chloro-2-methyl-phenyl)-6-oxo-4,5-dihydropyridazin-1-yl]acetate (2.07 g, 50%).

Step 2: Preparation of 2-[3-(3-chlorophenyl)-6-oxo-4,5-dihydropyridazin-1-yl]acetic acid

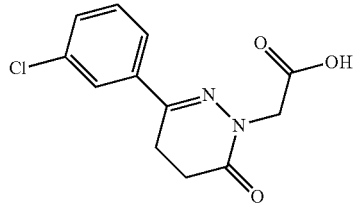 [SMILES: O=C(O)CN1N=C(c2cccc(Cl)c2)CCC1=O]

A mixture of ethyl 2-[3-(3-chlorophenyl)-6-oxo-4,5-dihydropyridazin-1-yl]acetate (2.07 g, 7 mmol) and lithium hydroxide monohydrate (600 mg, 14 mmol) in tetrahydrofuran/water (50 mL, V/V=1/1) was heated with stirring at 60° C. for 1 hour. The mixture was concentrated under vacuum to remove the organic solvent, then the aqueous residue was acidified to pH=2 with hydrochloric acid (1 M). The mixture was extracted with ethyl acetate and the organic phase was dried over anhydrous sodium sulfate, filtered and concentrated under vacuum to afford 2-[3-(3-chlorophenyl)-6-oxo-4,5-dihydropyridazin-1-yl]acetic acid (1.15 g, 80%).

Step 3: Preparation of N-(4-chlorophenyl)-2-[3-(3-chlorophenyl)-6-oxo-4,5-dihydropyridazin-1-yl]-N-methyl-acetamide

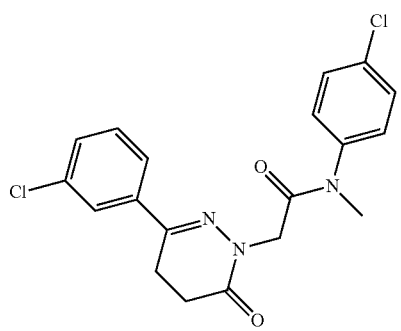 [SMILES: CN(C(=O)CN1N=C(c2cccc(Cl)c2)CCC1=O)c1ccc(Cl)cc1]

The title compound was prepared in analogy to Example 1-1 by using 2-[3-(3-chlorophenyl)-6-oxo-4,5-dihydropyridazin-1-yl]acetic acid (134.0 mg) and 4-chloro-N-methylaniline (142 mg) instead of 2-[3-(4-chlorophenyl)-6-oxo-4,5-dihydropyridazin-1-yl]acetic acid and 4-chloro-N-methylaniline. N-(4-Chlorophenyl)-2-[3-(3-chlorophenyl)-6-oxo-4,5-dihydropyridazin-1-yl]-N-methyl-acetamide was obtained (40 mg). $^1$H NMR (400 MHz, DMSO-d6): δ 7.78 (m, 1H), 7.66-7.72 (m. 1H), 7.42-7.58 (m, 6H), 4.29 (s, 2H), 3.19 (s, 2H), 2.98 (t, J=7.8 Hz, 2H), 2.48 (t, J=8.4 Hz, 2H). MS obsd. (ESI$^+$) [(M+H)$^+$]: 390.

Example 2-1: 2-[3-(4-Chlorophenyl)-6-oxo-pyridazin-1-yl]-N-methyl-N-[4-(trifluoromethyl)phenyl]acetamide

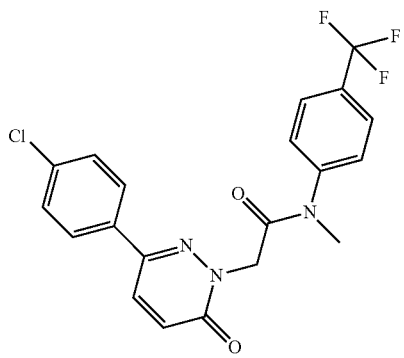 [SMILES: CN(C(=O)Cn1nc(-c2ccc(Cl)cc2)ccc1=O)c1ccc(C(F)(F)F)cc1]

Step 1: Preparation of ethyl 2-(3-chloro-6-oxo-pyridazin-1-yl) acetate

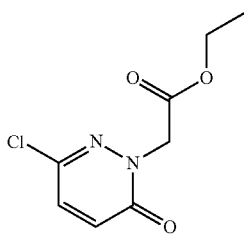

To a solution of 3-chloro-1H-pyridazin-6-one (5 g, 38.3 mmol, TCI, Catalog number: C2377) in dimethylformamide (30 mL) was added potassium carbonate (17.9 g, 130.0 mmol), followed by slow addition of ethyl 2-bromoacetate (4.7 mL, 42.0 mmol) at 0° C. After the addition was completed, the reaction mixture was warmed to room temperature and stirred at room temperature for 2 hours, then diluted by water (5 mL) and extracted with ethyl acetate (30 mL) three times. The combined organic phases were washed with brine, dried over anhydrous magnesium sulfate and concentrated under vacuum. The crude was purified by flash column chromatography (eluted with petroleum ether/ethyl acetate=3:1) to give 7.4 g of ethyl 2-(3-chloro-6-oxo-pyridazin-1-yl) acetate as a colorless solid.

Step 2: Preparation of 2-(3-chloro-6-oxo-pyridazin-1-yl) acetic acid

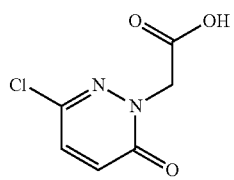 [SMILES: O=C(O)Cn1nc(Cl)ccc1=O]

Ethyl 2-(3-chloro-6-oxo-pyridazin-1-yl)acetate (3.0 g, 13.8 mmol) was hydrolyzed with lithium hydroxide monohydrate (500 mg, 11.9 mmol) in tetrahydrofuran/water (10 mL/5 mL) at room temperature for 6 hours. The resulting mixture was acidified to pH=2 with aqueous hydrochloric acid (1 M) and extracted with ethyl acetate (30 mL) three times. The combined organic extracts were washed with brine, dried over anhydrous magnesium sulfate, filtered and evaporated under vacuum to give 2-(3-chloro-6-oxo-pyridazin-1-yl)acetic acid (2.1 g) as a solid.

Step 3: Preparation of 2-(3-chloro-6-oxo-pyridazin-1-yl)-N-methyl-N-[4-(trifluoromethyl)phenyl]acetamide

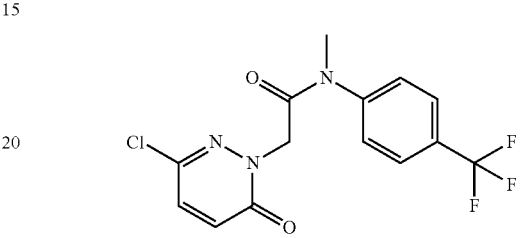

To a solution of 2-(3-chloro-6-oxo-pyridazin-1-yl)acetic acid (2.1 g, 11.1 mmol) in dichloromethane (20 mL) was added 1-propylphosphonic acid cyclic anhydride (10.5 g, wt. 50% solution in ethyl acetate), followed by addition of triethylamine (5 mL, 36 mmol) and methyl-(4-trifluoromethyl-phenyl)amine (2.3 g, 13.1 mmol). The reaction mixture was stirred at room temperature for 5 hours, the solvent was removed and the crude was purified by flash column chromatography (eluted with petroleum ether/ethyl acetate, V/V=3/1) to give 2-(3-chloro-6-oxo-pyridazin-1-yl)-N-methyl-N-[4-(trifluoromethyl)phenyl]acetamide as a white solid (2.2 g).

Step 4: Preparation of 2-[3-(4-chlorophenyl)-6-oxo-pyridazin-1-yl]-N-methyl-N-[4-(trifluoromethyl)phenyl]acetamide

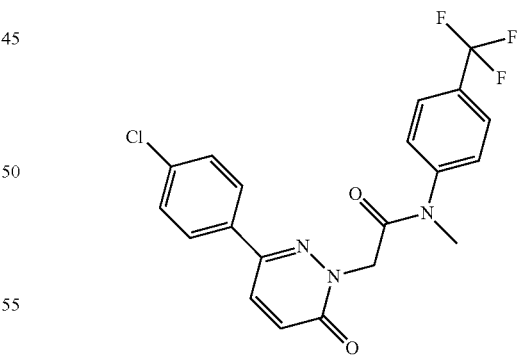

To a solution of 2-(3-chloro-6-oxo-pyridazin-1-yl)-N-methyl-N-[4-(trifluoromethyl) phenyl]acetamide (70 mg, 0.2 mmol) in dioxane (3 mL) was added (4-chlorophenyl) boronic acid (50 mg, 0.32 mmol, Aldrich, Catalog number: 417548), RuPhos (20 mg, 0.043 mmol), $Pd_2(dba)_3$ (30 mg, 0.05 mmol) and potassium phosphate (80 mg, 0.368 mmol). The suspension was heated at 100° C. for 5 hours, then filtrated and the filtrate was concentrated. The residue was purified by preparative HPLC to give 2-[3-(4-chlorophenyl)-

6-oxo-pyridazin-1-yl]-N-methyl-N-[4-(trifluoromethyl)phenyl]acetamide as a white solid (20 mg). ¹H NMR (400 MHz, CDCl₃): δ 7.78 (d, J=8.3 Hz, 2H), 7.69 (m, 3H), 7.58 (d, J=8.3 Hz, 2H), 7.44 (m, 2H), 7.03 (d, J=9.8 Hz, 1H), 4.77 (s, 2H), 3.39 (s, 3H). MS obsd. (ESI⁺) [(M+H)⁺]: 422.

Example 2-2: 2-[3-(4-Chloro-3-fluorophenyl)-6-oxo-pyridazin-1-yl]-N-methyl-N-[4-(trifluoromethyl)phenyl]acetamide

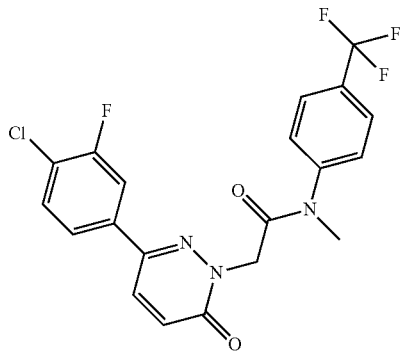 [SMILES: CN(C(=O)Cn1nc(-c2ccc(Cl)c(F)c2)ccc1=O)c1ccc(C(F)(F)F)cc1]

The title compound was prepared in analogy to Example 2-1 by using 2-(3-chloro-6-oxo-pyridazin-1-yl)-N-methyl-N-[4-(trifluoromethyl)phenyl]acetamide (70 mg) and 4-chloro-3-fluorophenylboronic (55 mg, Aldrich, Catalog number: 512230) instead of 2-(3-chloro-6-oxo-pyridazin-1-yl)-N-methyl-N-[4-(trifluoromethyl) phenyl]acetamide and (4-chlorophenyl)-dimethylborane.2-[3-(4-Chloro-3-fluorophenyl)-6-oxo-pyridazin-1-yl]-N-methyl-N-[4-(trifluoromethyl)phenyl]acetamide was obtained as a colorless solid (30 mg). ¹H NMR (400 MHz, CDCl₃): δ 7.79 (d, J=8.3 Hz, 2H), 7.66 (d, J=9.8 Hz, 2H), 7.60 (m, 2H), 7.48 (m, 2H), 7.05 (d, J=9.8 Hz, 1H), 4.77 (s, 2H), 3.39 (s, 3H). MS obsd. (ESI⁺) [(M+H)⁺]: 440.

Example 2-3: 2-[3-(4-Chloro-2-fluoro-phenyl)-6-oxo-pyridazin-1-yl]-N-methyl-N-[4-(trifluoromethyl)phenyl]acetamide

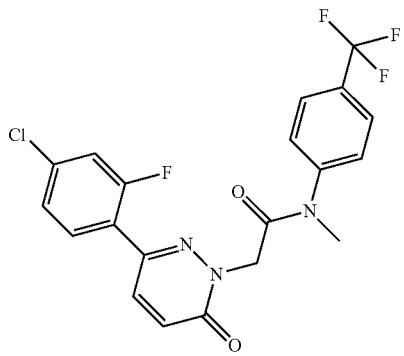 [SMILES: CN(C(=O)Cn1nc(-c2ccc(Cl)cc2F)ccc1=O)c1ccc(C(F)(F)F)cc1]

The title compound was prepared in analogy to Example 2-1 by using 2-(3-chloro-6-oxo-pyridazin-1-yl)-N-methyl-N-[4-(trifluoromethyl)phenyl]acetamide (70 mg) and 4-chloro-2-fluorophenylboronic acid (55 mg, Alfa Aesar, Catalog number: H28872) instead of 2-(3-chloro-6-oxo-pyridazin-1-yl)-N-methyl-N-[4-(trifluoromethyl) phenyl]acetamide and (4-chlorophenyl)-dimethylborane. 2-[3-(4-Chloro-2-fluoro-phenyl)-6-oxo-pyridazin-1-yl]-N-methyl-N-[4-(trifluoromethyl)phenyl]acetamide was obtained as a colorless solid (22 mg). ¹H NMR (400 MHz, CDCl₃): δ 7.79 (d, J=16 Hz, 2H), 7.67 (m, 2H), 7.57 (d, J=8 Hz, 2H), 7.23 (m, 2H), 7.0 (d, J=9.8 Hz, 1H), 4.77 (s, 2H), 3.38 (s, 3H). MS obsd. (ESI⁺) [(M+H)⁺]: 440.

Example 2-4: 2-[3-(2-Chloro-6-fluoro-phenyl)-6-oxo-pyridazin-1-yl]-N-methyl-N-[4-(trifluoromethyl)phenyl]acetamide

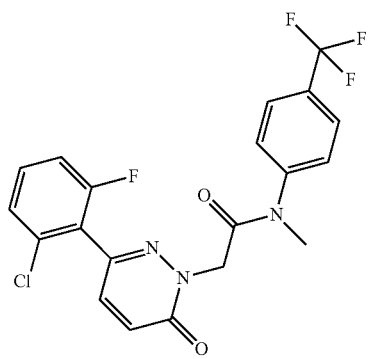 [SMILES: CN(C(=O)Cn1nc(-c2c(F)cccc2Cl)ccc1=O)c1ccc(C(F)(F)F)cc1]

The title compound was prepared in analogy to Example 2-1 by using 2-(3-chloro-6-oxo-pyridazin-1-yl)-N-methyl-N-[4-(trifluoromethyl)phenyl]acetamide (70 mg) and 6-chloro-2-fluorophenylboronic acid (50 mg, Aldrich, Catalog number: 566071) instead of 2-(3-chloro-6-oxo-pyridazin-1-yl)-N-methyl-N-[4-(trifluoromethyl) phenyl]acetamide and (4-chlorophenyl)-dimethylborane. 2-[3-(2-Chloro-6-fluoro-phenyl)-6-oxo-pyridazin-1-yl]-N-methyl-N-[4-(trifluoromethyl)phenyl]acetamide was obtained as a colorless solid (15 mg). ¹H NMR (400 MHz, CDCl₃): δ 7.75 (d, J=8.3 Hz, 2H), 7.55 (d, J=8.3 Hz, 2H), 7.34 (m, 3H), 7.12 (dd, J=8.0 Hz, 1H), 7.01 (d, J=8 Hz, 1H), 4.77 (s, 2H), 3.37 (s, 3H). MS obsd. (ESI⁺) [(M+H)⁺]: 440.

Example 2-5: N-(4-Chlorophenyl)-2-[3-(4-chlorophenyl)-6-oxo-pyridazin-1-yl]-N-methyl-acetamide

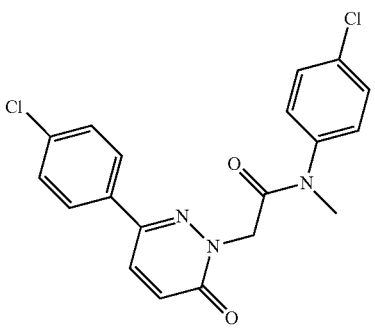 [SMILES: CN(C(=O)Cn1nc(-c2ccc(Cl)cc2)ccc1=O)c1ccc(Cl)cc1]

A mixture of N-(4-chlorophenyl)-2-[3-(4-chlorophenyl)-6-oxo-4,5-dihydropyridazin-1-yl]-N-methyl-acetamide (116 mg, 0.3 mmol) (Example 1-1) and CuCl₂ (80 mg, 0.6 mmol) in acetonitrile (5 mL) was heated with stirring at 100° C. for 30 minutes. Then to the mixture was added water and the mixture was extracted with ethyl acetate. The organic phase was dried over anhydrous sodium sulfate and concentrated under vacuum. The residue was purified by preparative TLC to afford N-(4-chlorophenyl)-2-[3-(4-chlorophenyl)-6-oxo-pyridazin-1-yl]-N-methyl-acetamide (44 mg, 38%). $^1$H NMR (400 MHz, CDCl$_3$): δ 7.67 (d, J=8 Hz, 2H). 7.64 (d, J=8 Hz, 1H), 7.42 (d, J=8 Hz, 2H), 7.38 (d, J=8 Hz, 2H), 7.35 (d, J=8 Hz, 2H), 6.99 (d, J=8 Hz, 1H), 4.71 (s, 2H), 3.30 (s, 3H). MS obsd. (ESI$^+$) [(M+H)$^+$]: 388.

Example 3-1: 2-[6-(4-Chlorophenyl)-3-oxo-4,5-dihydro-1,2,4-triazin-2-yl]-N-methyl-N-[4-(trifluoromethyl)phenyl]acetamide

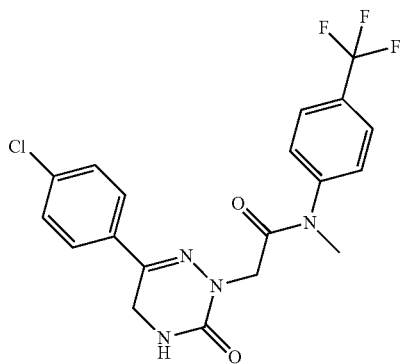 [SMILES: CN(C(=O)CN1N=C(c2ccc(Cl)cc2)CNC1=O)c1ccc(C(F)(F)F)cc1]

Step 1: Preparation of 3-[2-(4-chlorophenyl)-2-oxo-ethyl]thiazolidine-2,4-dione

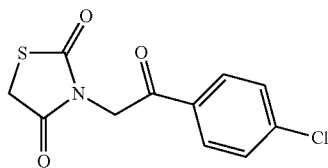 [SMILES: O=C(CN1C(=O)CSC1=O)c1ccc(Cl)cc1]

To a solution of thiazolidine-2,4-dione (2 g, 90%, 15.4 mmol) in anhydrous dimethylformamide was added sodium hydride in small portions (700 mg, 60% in oil, 17.5 mmol) at 0° C. After the addition, the resulting suspension was stirred at 0° C. for half an hour. Then to the resulting mixture was added 2-bromo-1-(4-chlorophenyl)ethanone (3.6 g, 15.4 mmol). The resulting suspension was stirred at room temperature overnight. After the reaction was complete, the resulting mixture was diluted with water (20 mL). The solid was collected by vacuum filtration and washed with water. 3-[2-(4-Chlorophenyl)-2-oxo-ethyl]thiazolidine-2,4-dione was obtained (4.1 g).

Step 2: Preparation of ethyl 2-[6-(4-chlorophenyl)-3-oxo-4,5-dihydro-1,2,4-triazin-2-yl]acetate

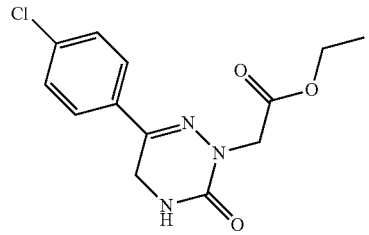 [SMILES: CCOC(=O)CN1N=C(c2ccc(Cl)cc2)CNC1=O]

To a solution of 3-[2-(4-chlorophenyl)-2-oxo-ethyl]thiazolidine-2,4-dione (1.0 g, 3.7 mmol) in ethanol (20 mL) was added ethyl hydrazinoacetate hydrochloride (600 mg, 3.88 mmol), followed by addition of triethylamine (1.5 mL, 10.8 mmol). The reaction mixture was heated under reflux for 5 hours, and then cooled to room temperature. The solvent was removed under vacuum and the crude was purified by flash column chromatography (eluted with petroleum ether/ethyl acetate=3:7) to give 250 mg of ethyl 2-[6-(4-chlorophenyl)-3-oxo-4,5-dihydro-1,2,4-triazin-2-yl]acetate.

Step 3: Preparation of 2-[6-(4-chlorophenyl)-3-oxo-4,5-dihydro-1,2,4-triazin-2-yl]acetic acid

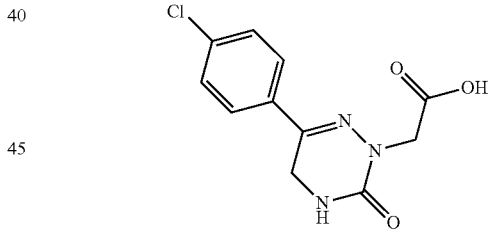

Ethyl 2-[6-(4-chlorophenyl)-3-oxo-4,5-dihydro-1,2,4-triazin-2-yl]acetate (100 mg, 0.38 mmol) was hydrolyzed by lithium hydroxide monohydrate (30 mg, 0.71 mmol) in tetrahydrofuran/water (10 mL/5 mL) by heating at 50° C. for 1 hour. Then the reaction mixture was cooled to room temperature, acidified to pH=2 with aqueous hydrochloric acid (1M) and extracted with ethyl acetate (30 mL) three times. The organic extracts were washed with brine, dried over anhydrous magnesium sulfate and concentrated under vacuum to give 2-[6-(4-chlorophenyl)-3-oxo-4,5-dihydro-1,2,4-triazin-2-yl]acetic acid as a colorless solid (85 mg).

Step 4: Preparation of 2-[6-(4-chlorophenyl)-3-oxo-4,5-dihydro-1,2,4-triazin-2-yl]-N-methyl-N-[4-(trifluoromethyl)phenyl]acetamide

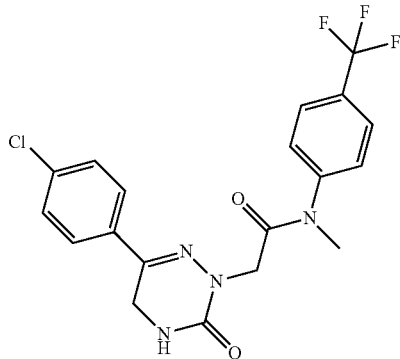 [SMILES: CN(C(=O)CN1N=C(c2ccc(Cl)cc2)CNC1=O)c1ccc(C(F)(F)F)cc1]

To a solution of 2-[6-(4-chlorophenyl)-3-oxo-4,5-dihydro-1,2,4-triazin-2-yl]acetic acid (60 mg, 0.224 mmol) in dichloromethane (5 mL) was added 1-propylphosphonic acid cyclic anhydride (300 mg, wt. 50% solution in ethyl acetate, Alfa Aesar: Catalog number: L11911) followed by addition of triethylamine (0.12 mL, 0.86 mmol) and methyl-(4-trifluoromethyl-phenyl)amine (50 mg, 0.285 mmol). The mixture was stirred at room temperature for 5 hours. After the reaction was complete, the solvent was removed under vacuum and the residue was purified by preparative HPLC to give 2-[6-(4-chlorophenyl)-3-oxo-4,5-dihydro-1,2,4-triazin-2-yl]-N-methyl-N-[4(trifluoromethyl)phenyl]acetamide as a white solid (20 mg). $^1$H NMR (400 MHz, CDCl$_3$): J=8.0 7.45 (d, J=8.0-7.29 (m, 2H), 7.35 (m, 2H), 5.23 (s, 1H), 4.46 (s, 2H), 4.31 (s, 2H), 3.38 (s, 3H).

Example 3-2: N-(4-Chlorophenyl)-2-[6-(4-chlorophenyl)-3-oxo-1,2,4-triazin-2-yl]-N-methyl-acetamide

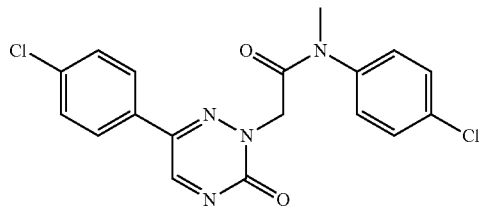 [SMILES: CN(C(=O)Cn1nc(-c2ccc(Cl)cc2)cnc1=O)c1ccc(Cl)cc1]

Step 1: Preparation of 6-(4-chlorophenyl)-4,5-dihydro-2H-1,2,4-triazin-3-one

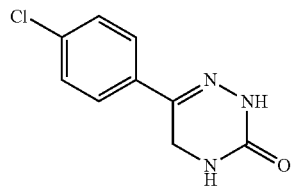 [SMILES: O=C1NCC(c2ccc(Cl)cc2)=NN1]

To a solution of 3-[2-(4-chlorophenyl)-2-oxo-ethyl]thiazolidine-2,4-dione (1.1 g, 4.1 mmol) in methanol (10 mL) was added hydrazine hydrate (412 mg, 8.24 mmol). The mixture was stirred at room temperature for 3 hours, and then heated under reflux for 6 hours. After the reaction was complete, the mixture was cooled to room temperature, the precipitate was filtrated to give 6-(4-chlorophenyl)-4,5-dihydro-2H-1,2,4-triazin-3-one as a yellow solid (180 mg).

Step 2: Preparation of 6-(4-chlorophenyl)-2H-1,2,4-triazin-3-one

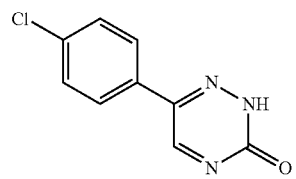 [SMILES: O=c1ncc(-c2ccc(Cl)cc2)n[nH]1]

To a suspension of 6-(4-chlorophenyl)-4,5-dihydro-2H-1,2,4-triazin-3-one (180 mg, 0.86 mmol) in water (10 mL) was added 3-nitrobenzenesulfonic acid sodium salt (200 mg, 0.89 mmol), followed by addition of 50%/(W/W) aqueous sodium hydroxide. The mixture was heated under reflux for 3 hours. After the reaction was complete, the resulting mixture was cooled to room temperature and acidified to pH=2 with hydrochloric acid (1 M). The precipitate was filtrated and dried to give 6-(4-chlorophenyl)-2H-1,2,4-triazin-3-one as a white solid (160 mg).

Step 3: Preparation of N-(4-chlorophenyl)-2-[6-(4-chlorophenyl)-3-oxo-1,2,4-triazin-2-yl]-N-methyl-acetamide

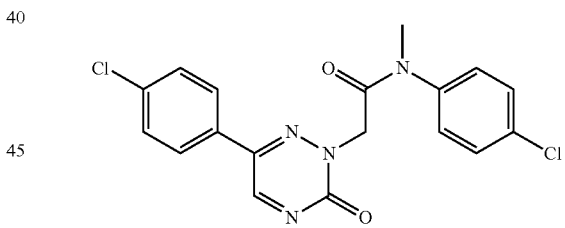

To a solution of 6-(4-chlorophenyl)-2H-1,2,4-triazin-3-one (50 mg, 0.24 mmol) in dimethylformamide (3 mL) was added sodium hydride (25 mg, 60% dispersion in oil, 0.625 mmol) in small portions. The resulting suspension was stirred at room temperature for 1 hour, then to the resulting mixture was added 2-bromo-N-(4-chlorophenyl)-N-methyl-acetamide (95 mg, 0.36 mmol). And the resulting mixture was stirred at room temperature for 1 hour. After reaction, the reaction mixture was diluted with aqueous ammonium chloride, and extracted with ethyl acetate (30 mL) three times. The combined extracts were washed with brine, dried over anhydrous magnesium sulfate and evaporated. The crude was purified by preparative HPLC to give N-(4-chlorophenyl)-2-[6-(4-chlorophenyl)-3-oxo-1,2,4-triazin-2-yl]-N-methyl-acetamide as a white solid (10 mg). $^1$H NMR (400 MHz, CDCl$_3$): δ 7.73 (d, J=7.0 Hz, 2H), 7.46 (d, J=7.0 Hz, 2H), 7.30 (m, 4H), 5.72 (s, 1H), 4.61 (m, 1H), 4.14 (m, 1H), 3.33 (s, 3H). MS obsd. (ESI$^+$) [(M+H)$^+$]: 389.

Biological Examples

Example 4 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

Results of HBsAg assay are given in Table 1.

TABLE 1

Activity data of particular compounds

| Example number | IC 50 (μM) |
|---|---|
| 1-1 | 1.58 |
| 1-2 | 0.74 |
| 1-3 | 0.301 |
| 1-4 | 0.994 |
| 1-5 | 9.63 |
| 1-6 | 3.63 |
| 1-7 | 2.49 |
| 1-8 | 0.246 |
| 1-9 | 0.389 |
| 1-10 | 5.63 |
| 1-11 | 8.74 |
| 1-12 | 0.885 |
| 1-13 | 6.61 |
| 1-14 | 3.02 |
| 1-15 | 5.24 |
| 1-16 | 3.86 |
| 1-17 | 1.17 |
| 1-18 | 0.90 |
| 1-19 | 1.0 |
| 1-20 | 5.69 |
| 1-21 | 2.08 |
| 1-22 | 0.94 |

TABLE 1-continued

Activity data of particular compounds

| Example number | IC 50 (μM) |
|---|---|
| 1-23 | 0.46 |
| 1-24 | 0.168 |
| 1-25 | 0.24 |
| 1-26 | 1.88 |
| 1-27 | 0.814 |
| 1-28 | 4.59 |
| 1-29 | 0.483 |
| 1-30 | 0.402 |
| 1-31 | 0.83 |
| 1-32 | 0.513 |
| 1-33 | 0.85 |
| 1-34 | 1.25 |
| 1-35 | 4.66 |
| 1-36 | 3.1 |
| 1-37 | 3.14 |
| 1-38 | 2.35 |
| 1-39 | 0.369 |
| 1-40 | 0.38 |
| 1-41 | 0.25 |
| 1-42 | 0.52 |
| 1-43 | 2.47 |
| 1-44 | 0.96 |
| 1-45 | 0.23 |
| 1-46 | 0.42 |
| 1-47 | 8.93 |
| 1-48 | 1.88 |
| 1-49 | 3.87 |
| 1-50 | 1.23 |
| 1-51 | 1.16 |
| 1-52 | 0.47 |
| 1-53 | 0.86 |
| 1-54 | 1.93 |
| 1-55 | 3.82 |
| 1-56 | 9.51 |
| 1-57 | 3.02 |
| 2-1 | 0.90 |
| 2-2 | 0.52 |
| 2-3 | 1.50 |
| 2-4 | 4.76 |
| 2-5 | 1.77 |
| 3-1 | 10.3 |
| 3-2 | 6.23 |

The invention claimed is:

1. A compound of formula (I)

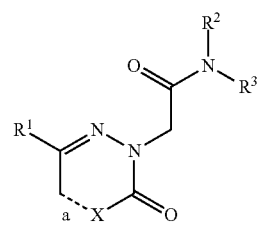

wherein
- $R_1$ is phenyl; or phenyl substituted once or twice by $C_{1-6}$alkyl, halogen, trifluoromethyl, or cyano;
- $R_2$ is $C_{1-6}$alkyl;
- $R_3$ is phenyl; or phenyl substituted once or twice by $C_{1-6}$alkyl, halogen, trifluoromethyl, cyano, $C_{1-6}$alkoxy, trifluoromethoxy, —C(O)—$C_{1-6}$alkoxy, or —C(O)—$NR^4R^5$, wherein one of $R^4$ and $R^5$ is hydrogen or $C_{1-6}$alkyl, and the other one is $C_{1-6}$alkyl or $C_{3-7}$cycloalkyl;
- a is a single bond; and
- X is $CH_2$ or NH;
- or a pharmaceutically acceptable salt thereof.

2. A compound of formula (I) according to claim 1, wherein
  $R^1$ is phenyl; or phenyl substituted once or twice by methyl, fluoro, chloro, bromo, trifluoromethyl, or cyano;
  $R^2$ is methyl; and
  $R^3$ is phenyl; or phenyl substituted once or twice by methyl, fluoro, chloro, trifluoromethyl, cyano, methoxy, trifluoromethoxy, methoxycarbonyl, or —C(O)—NR$^4$R$^5$, wherein one of $R^4$ and $R^5$ is hydrogen, methyl, or isopropyl, and the other one is isopropyl, pentyl, or cyclohexyl;
  or a pharmaceutically acceptable salt thereof.

3. A compound of formula (I) according to claim 1, or a pharmaceutically acceptable salt thereof, wherein $R^1$ is phenyl substituted once or twice by halogen, or trifluoromethyl.

4. A compound of formula (I) according to claim 1, or a pharmaceutically acceptable salt thereof, wherein $R^1$ is phenyl substituted once or twice by fluoro, chloro, or trifluoromethyl.

5. A compound of formula (I) according to claim 1, or a pharmaceutically acceptable salt thereof, wherein $R^3$ is phenyl; or phenyl substituted once or twice by halogen or trifluoromethyl.

6. A compound of formula (I) according to claim 1, or a pharmaceutically acceptable salt thereof, wherein $R^3$ is phenyl; or phenyl substituted once or twice by fluoro, chloro, or trifluoromethyl.

7. A compound of formula (I) according to claim 1, or a pharmaceutically acceptable salt thereof, wherein X is CH$_2$.

8. A compound according to claim 1, or a pharmaceutically acceptable salt thereof, wherein
  $R^1$ is phenyl substituted once or twice by halogen or trifluoromethyl;
  $R^2$ is C$_{1-6}$alkyl;
  $R^3$ is phenyl; or phenyl substituted once or twice by halogen or trifluoromethyl; and
  X is CH$_2$;
  or a pharmaceutically acceptable salt thereof.

9. A compound according to claim 1, or a pharmaceutically acceptable salt thereof, wherein
  $R^1$ is phenyl substituted once or twice by fluoro, chloro, or trifluoromethyl;
  $R^2$ is methyl;
  $R^3$ is phenyl; or phenyl substituted once or twice by fluoro, chloro, or trifluoromethyl; and
  X is CH$_2$;
  or a pharmaceutically acceptable salt thereof.

10. A compound of formula (I) according to claim 1, selected from the group consisting of
  N-(4-Chlorophenyl)-2-[3-(4-chlorophenyl)-6-oxo-4,5-dihydropyridazin-1-yl]-N-methyl-acetamide;
  2-[3-(4-Chlorophenyl)-6-oxo-4,5-dihydropyridazin-1-yl]-N-[4-fluoro-3-(trifluoromethyl)phenyl]-N-methyl-acetamide;
  2-[3-(4-Chlorophenyl)-6-oxo-4,5-dihydropyridazin-1-yl]-N-[3-fluoro-4-(trifluoromethyl)phenyl]-N-methyl-acetamide;
  N-(4-Chloro-3-fluoro-phenyl)-2-[3-(4-chlorophenyl)-6-oxo-4,5-dihydropyridazin-1-yl]-N-methyl-acetamide;
  2-[3-(4-Chlorophenyl)-6-oxo-4,5-dihydropyridazin-1-yl]-N-(3-methoxyphenyl)-N-methyl-acetamide;
  2-[3-(4-Chlorophenyl)-6-oxo-4,5-dihydropyridazin-1-yl]-N-(4-fluorophenyl)-N-methyl-acetamide;
  2-[3-(4-Chlorophenyl)-6-oxo-4,5-dihydropyridazin-1-yl]-N-methyl-N-(p-tolyl)acetamide;
  2-[3-(4-Chlorophenyl)-6-oxo-4,5-dihydropyridazin-1-yl]-N-(3,4-dichlorophenyl)-N-methyl-acetamide;
  2-[3-(4-Chlorophenyl)-6-oxo-4,5-dihydropyridazin-1-yl]-N-methyl-N-[4-(trifluoromethyl)phenyl]acetamide;
  2-[3-(4-Chlorophenyl)-6-oxo-4,5-dihydropyridazin-1-yl]-N-(4-cyanophenyl)-N-methyl-acetamide;
  Methyl 4-[[2-[3-(4-chlorophenyl)-6-oxo-4,5-dihydropyridazin-1-yl]acetyl]-methyl-amino]benzoate;
  4-[[2-[3-(4-Chlorophenyl)-6-oxo-4,5-dihydropyridazin-1-yl]acetyl]-methyl-amino]-N,N-diisopropyl-benzamide;
  2-[3-(4-Chlorophenyl)-6-oxo-4,5-dihydropyridazin-1-yl]-N-(2,4-difluorophenyl)-N-methyl-acetamide;
  4-[[2-[3-(4-Chlorophenyl)-6-oxo-4,5-dihydropyridazin-1-yl]acetyl]-methyl-amino]-N-methyl-N-pentyl-benzamide;
  4-[[2-[3-(4-Chlorophenyl)-6-oxo-4,5-dihydropyridazin-1-yl]acetyl]-methyl-amino]-N-cyclohexyl-benzamide;
  2-[3-(4-Chlorophenyl)-6-oxo-4,5-dihydropyridazin-1-yl]-N-methyl-N-[4-(trifluoromethoxy)phenyl]acetamide;
  2-[3-(4-Chlorophenyl)-6-oxo-4,5-dihydropyridazin-1-yl]-N-(3-fluorophenyl)-N-methyl-acetamide;
  N-(3-Chlorophenyl)-2-[3-(4-chlorophenyl)-6-oxo-4,5-dihydropyridazin-1-yl]-N-methyl-acetamide;
  2-[3-(4-Chlorophenyl)-6-oxo-4,5-dihydropyridazin-1-yl]-N-methyl-N-[3-(trifluoromethyl)phenyl]acetamide;
  2-[3-(4-Chlorophenyl)-6-oxo-4,5-dihydropyridazin-1-yl]-N-(4-methoxyphenyl)-N-methyl-acetamide;
  2-[3-(4-Chlorophenyl)-6-oxo-4,5-dihydropyridazin-1-yl]-N-methyl-N-(m-tolyl)acetamide;
  2-[3-(4-Chloro-3-fluoro-phenyl)-6-oxo-4,5-dihydropyridazin-1-yl]-N-(4-fluorophenyl)-N-methyl-acetamide;
  2-[3-(4-Chloro-3-fluoro-phenyl)-6-oxo-4,5-dihydropyridazin-1-yl]-N-(3-fluorophenyl)-N-methyl-acetamide;
  2-[3-(4-Chloro-3-fluoro-phenyl)-6-oxo-4,5-dihydropyridazin-1-yl]-N-(3-chlorophenyl)-N-methyl-acetamide;
  2-[3-(4-Chloro-3-fluoro-phenyl)-6-oxo-4,5-dihydropyridazin-1-yl]-N-methyl-N-[4-(trifluoromethyl)phenyl]acetamide;
  2-[3-(4-Chloro-2-methyl-phenyl)-6-oxo-4,5-dihydropyridazin-1-yl]-N-(4-chlorophenyl)-N-methyl-acetamide;
  2-[3-(4-Chloro-2-methyl-phenyl)-6-oxo-4,5-dihydropyridazin-1-yl]-N-(3-chlorophenyl)-N-methyl-acetamide;
  2-[3-(4-Chloro-2-methyl-phenyl)-6-oxo-4,5-dihydropyridazin-1-yl]-N-(3-fluorophenyl)-N-methyl-acetamide;
  2-[3-(4-Chloro-2-methyl-phenyl)-6-oxo-4,5-dihydropyridazin-1-yl]-N-methyl-N-[3-(trifluoromethyl)phenyl]acetamide;
  2-[3-(2,4-Difluorophenyl)-6-oxo-4,5-dihydropyridazin-1-yl]-N-methyl-N-[4-(trifluoromethyl)phenyl]acetamide;
  2-[3-(2, 4-Difluorophenyl)-6-oxo-4, 5-dihydropyridazin-1-yl]-N-methyl-N-[3-(trifluoromethyl)phenyl]acetamide;
  2-[3-(2,4-Difluorophenyl)-6-oxo-4,5-dihydropyridazin-1-yl]-N-[4-fluoro-3-(trifluoromethyl)phenyl]-N-methyl-acetamide;
  N-(4-Chlorophenyl)-2-[3-(2,4-difluorophenyl)-6-oxo-4, 5-dihydropyridazin-1-yl]-N-methyl-acetamide;

2-[3-(2,4-Difluorophenyl)-6-oxo-4,5-dihydropyridazin-1-yl]-N-(3-fluorophenyl)-N-methyl-acetamide;
2-[3-(4-Fluoro-3-methyl-phenyl)-6-oxo-4,5-dihydropyridazin-1-yl]-N-methyl-N-[3-(trifluoromethyl)phenyl]acetamide;
2-[3-(4-Fluoro-3-methyl-phenyl)-6-oxo-4,5-dihydropyridazin-1-yl]-N-methyl-N-[4-(trifluoromethyl)phenyl]acetamide;
2-[3-(4-Fluoro-3-methyl-phenyl)-6-oxo-4,5-dihydropyridazin-1-yl]-N-[4-fluoro-3-(trifluoromethyl)phenyl]-N-methyl-acetamide;
2-[3-(4-Fluoro-3-methyl-phenyl)-6-oxo-4,5-dihydropyridazin-1-yl]-N-[3-fluoro-4-(trifluoromethyl)phenyl]-N-methyl-acetamide;
N-(3-Chlorophenyl)-N-methyl-2-[6-oxo-3-[4-(trifluoromethyl)phenyl]-4,5-dihydropyridazin-1-yl]acetamide;
N-Methyl-2-[6-oxo-3-[4-(trifluoromethyl)phenyl]-4,5-dihydropyridazin-1-yl]-N-[4-(trifluoromethyl)phenyl]acetamide;
N-Methyl-2-[6-oxo-3-[4-(trifluoromethyl)phenyl]-4,5-dihydropyridazin-1-yl]-N-[3-(trifluoromethyl)phenyl]acetamide;
N-(3-Fluorophenyl)-N-methyl-2-[6-oxo-3-[4-(trifluoromethyl)phenyl]-4,5-dihydropyridazin-1-yl]acetamide;
N-(4-Fluorophenyl)-N-methyl-2-[6-oxo-3-[4-(trifluoromethyl)phenyl]-4,5-dihydropyridazin-1-yl]acetamide;
N-(4-Chlorophenyl)-N-methyl-2-[6-oxo-3-[4-(trifluoromethyl)phenyl]-4,5-dihydropyridazin-1-yl]acetamide;
2-[3-(3,4-Dichlorophenyl)-6-oxo-4,5-dihydropyridazin-1-yl]-N-methyl-N-[4-(trifluoromethyl)phenyl]acetamide;
N-(4-Chlorophenyl)-2-[3-(3,4-dichlorophenyl)-6-oxo-4,5-dihydropyridazin-1-yl]-N-methyl-acetamide;
2-[3-(4-Fluorophenyl)-6-oxo-4,5-dihydropyridazin-1-yl]-N-methyl-N-phenyl-acetamide;
N-(4-Chlorophenyl)-2-[3-(4-fluorophenyl)-6-oxo-4,5-dihydropyridazin-1-yl]-N-methyl-acetamide;
2-[3-(4-Bromophenyl)-6-oxo-4,5-dihydropyridazin-1-yl]-N-methyl-N-phenyl-acetamide;
2-[3-(4-Bromophenyl)-6-oxo-4,5-dihydropyridazin-1-yl]-N-(4-chlorophenyl)-N-methyl-acetamide;
2-[3-(4-Bromophenyl)-6-oxo-4,5-dihydropyridazin-1-yl]-N-methyl-N-[4-(trifluoromethyl)phenyl]acetamide;
2-[3-(3, 4-Difluorophenyl)-6-oxo-4,5-dihydropyridazin-1-yl]-N-methyl-N-[3-(trifluoromethyl)phenyl]acetamide;
2-[3-(3,4-Difluorophenyl)-6-oxo-4,5-dihydropyridazin-1-yl]-N-methyl-N-[4-(trifluoromethyl)phenyl]acetamide;
N-(4-Chlorophenyl)-2-[3-(2,4-dichlorophenyl)-6-oxo-4,5-dihydropyridazin-1-yl]-N-methyl-acetamide;
N-(4-Chlorophenyl)-2-[3-(4-cyanophenyl)-6-oxo-4,5-dihydropyridazin-1-yl]-N-methyl-acetamide;
N-(4-Chlorophenyl)-N-methyl-2-[6-oxo-3-(p-tolyl)-4,5-dihydropyridazin-1-yl]acetamide;
N-(4-Chlorophenyl)-2-[3-(3-chlorophenyl)-6-oxo-4,5-dihydropyridazin-1-yl]-N-methyl-acetamide; and
2-[6-(4-Chlorophenyl)-3-oxo-4,5-dihydro-1,2,4-triazin-2-yl]-N-methyl-N-[4-(trifluoromethyl)phenyl]acetamide;
or a pharmaceutically acceptable salt thereof.

11. A compound of formula (I) according to claim 1, selected from the group consisting of 2-[3-(4-Chlorophenyl)-6-oxo-4,5-dihydropyridazin-1-yl]-N-[3-fluoro-4-(trifluoromethyl)phenyl]-N-methyl-acetamide;
2-[3-(4-Chlorophenyl)-6-oxo-4,5-dihydropyridazin-1-yl]-N-(3,4-dichlorophenyl)-N-methyl-acetamide;
2-[3-(4-Chlorophenyl)-6-oxo-4,5-dihydropyridazin-1-yl]-N-methyl-N-[4-(trifluoromethyl)phenyl]acetamide;
2-[3-(4-Chloro-3-fluoro-phenyl)-6-oxo-4,5-dihydropyridazin-1-yl]-N-(3-fluorophenyl)-N-methyl-acetamide;
2-[3-(4-Chloro-3-fluoro-phenyl)-6-oxo-4,5-dihydropyridazin-1-yl]-N-(3-chlorophenyl)-N-methyl-acetamide;
2-[3-(4-Chloro-3-fluoro-phenyl)-6-oxo-4,5-dihydropyridazin-1-yl]-N-methyl-N-[4-(trifluoromethyl)phenyl]acetamide;
2-[3-(2,4-Difluorophenyl)-6-oxo-4,5-dihydropyridazin-1-yl]-N-methyl-N-[4-(trifluoromethyl)phenyl]acetamide;
N-(3-Chlorophenyl)-N-methyl-2-[6-oxo-3-[4-(trifluoromethyl)phenyl]-4,5-dihydropyridazin-1-yl]acetamide;
N-Methyl-2-[6-oxo-3-[4-(trifluoromethyl)phenyl]-4,5-dihydropyridazin-1-yl]-N-[3-(trifluoromethyl)phenyl]acetamide;
N-(3-Fluorophenyl)-N-methyl-2-[6-oxo-3-[4-(trifluoromethyl)phenyl]-4,5-dihydropyridazin-1-yl]acetamide;
2-[3-(3,4-Dichlorophenyl)-6-oxo-4,5-dihydropyridazin-1-yl]-N-methyl-N-[4-(trifluoromethyl)phenyl]acetamide;
N-(4-Chlorophenyl)-2-[3-(3,4-dichlorophenyl)-6-oxo-4,5-dihydropyridazin-1-yl]-N-methyl-acetamide; and
2-[3-(3,4-Difluorophenyl)-6-oxo-4,5-dihydropyridazin-1-yl]-N-methyl-N-[3-(trifluoromethyl)phenyl]acetamide;
or a pharmaceutically acceptable salt thereof.

12. A process for the preparation of a compound of formula (I) according to claim 1, or a pharmaceutically acceptable salt thereof, comprising one of the following steps:
(a) the reaction of a compound of formula (A)

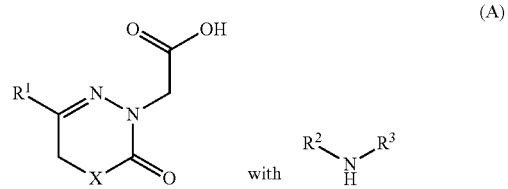

in the presence of a dehydrating reagent and a trialkylamine;
(b) the reaction of a compound of formula (B)

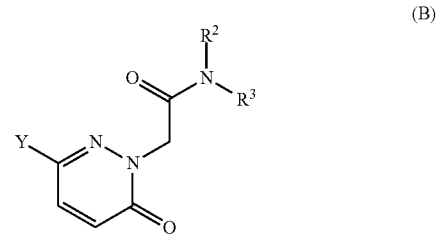

with R¹B(OH)₂ in the presence of a transition state metal catalyst, wherein Y is halogen;

(c) the reaction of a compound of formula (C)

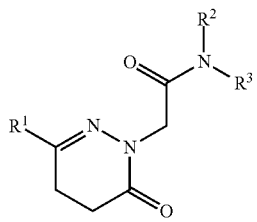

(C)

with an oxidizing reagent; or (d) the reaction of a compound of formula (D)

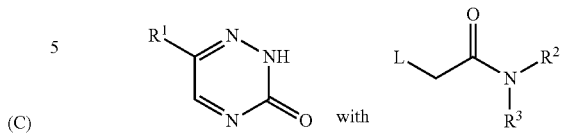

(D)

in the presence of a base in an inert solvent; wherein L is halogen.

13. A pharmaceutical composition comprising a compound according to claim 1, or a pharmaceutically acceptable salt thereof, and a therapeutically inert carrier.

14. A method for the treatment of HBV infection, which method comprises administering an effective amount of a compound according to claim 1, or a pharmaceutically acceptable salt thereof.

* * * * *